(12) United States Patent
Chang et al.

(10) Patent No.: US 9,006,458 B2
(45) Date of Patent: Apr. 14, 2015

(54) SURFACE ENHANCED RAMAN SPECTROSCOPY (SERS) COMPOUNDS AND METHODS OF THEIR PREPARATION

(75) Inventors: Young-Tae Chang, Singapore (SG); Kaustabh Kumar Maiti, Singapore (SG); Dinish Unnimadhava Kurup Soudamini Amma, Singapore (SG); Chit Yaw Fu, Singapore (SG); Malini Olivo, Singapore (SG); Kiat Seng Jason Soh, Singapore (SG); Seong-Wook Yun, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/272,187

(22) Filed: Oct. 12, 2011

(65) Prior Publication Data

US 2012/0128592 A1  May 24, 2012

Related U.S. Application Data

(60) Provisional application No. 61/392,044, filed on Oct. 12, 2010.

(51) Int. Cl.
| | | |
|---|---|---|
| C07D 339/04 | (2006.01) | |
| C07D 409/10 | (2006.01) | |
| C12Q 1/68 | (2006.01) | |
| A61K 49/00 | (2006.01) | |
| B82Y 15/00 | (2011.01) | |
| C07C 251/30 | (2006.01) | |
| C07D 295/135 | (2006.01) | |
| C07D 409/12 | (2006.01) | |
| G01N 33/533 | (2006.01) | |

(52) U.S. Cl.
CPC .......... *C12Q 1/6816* (2013.01); *A61K 49/0065* (2013.01); *B82Y 15/00* (2013.01); *C07C 251/30* (2013.01); *C07D 295/135* (2013.01); *C07D 339/04* (2013.01); *C07D 409/12* (2013.01); *G01N 33/533* (2013.01)

(58) Field of Classification Search
CPC ............................ C07D 339/04; C07D 409/10
USPC ............................................ 549/39; 548/527
See application file for complete search history.

(56) References Cited

U.S. PATENT DOCUMENTS

| 4,376,110 A | 3/1983 | David et al. | |
|---|---|---|---|
| 4,863,910 A * | 9/1989 | Takayanagi | 514/150 |
| 2008/0145947 A1 * | 6/2008 | Boga et al. | 436/130 |

OTHER PUBLICATIONS

Li, Gold Bulletin, 2010, vol. 43, No. 1, p. 29-41.*
Lin, Biosensors and Bioelectronics, 2008, vol. 24, p. 178-183.*
Murphy, 2008, Accounts of Chemical Research, vol. 41, p. 1721-1730.*
Substrate, http://www.merriam-webster.com/dictionary/substrate, access Jun. 3, 2013.*
Alivisatos, "The use of nanocrystals in biological detection," Nature Biotechnology, vol. 22, No. 1, pp. 47-52 (Jan. 2004).
Ahn et al., "Combinatorial Rosamine Library and Application to in Vivo Glutathione Probe," Journal of American Chemical Society, vol. 129, pp. 4510-4511 (2007).
Cho et al., "Combinatorial synthesis of a triphenylmethine library and their application in the development of Surface Enhanced Raman Scattering (SERS) probes," Chemical Communications, vol. 26, pp. 722-724 (2010).
Duncan, "Polymer conjugates as anticancer nanomedicines," Nature Reviews Cancer, vol. 6, pp. 688-701 (Sep. 2006).
Doering et al., "Spectroscopic Tags Using Dye-Embedded Nanoparticles and Surface-Enhanced Raman Scattering," Analytical Chemistry, vol. 75, No. 22, pp. 6171-6176 (Nov. 15, 2003).
Graham et al., "Control of enhanced Raman scattering using a DNA-based assembly process of dye-coded nanoparticles," Nature Nanotechnology, vol. 3, pp. 548-551 (Sep. 2008).
Hu et al., "Mammalian Cell Surface Imaging with Nitrile-Functionalized Nanoprobes: Biophysical Characterization of Aggregation and Polarization Anisotropy in SERS Imaging," American Chemical Society, vol. 129, pp. 14-15 (2007).

(Continued)

*Primary Examiner* — Rebecca Anderson
*Assistant Examiner* — Karen Cheng
(74) *Attorney, Agent, or Firm* — Blakely, Sokoloff, Taylor & Zafman LLP

(57) ABSTRACT

A compound for detecting an analyte using Surface Enhanced Raman Spectroscopy (SERS) and a method of forming the compound is provided. The compound has Formula I:

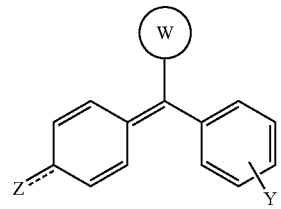

Formula I wherein W is selected from the group consisting of an optionally substituted aryl group and an optionally substituted heteroaryl group; each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms, ===== is used to denote a single or a double bond, and Z is NH, $NH_2$, NH—(C=O)—$(CH_2)_n$—SH, wherein n=1 to 10, or

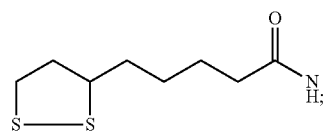

or a tautomer or stereoisomer thereof, or a salt thereof. A method and device for detecting an analyte using Surface Enhanced Raman Spectroscopy (SERS) is also provided.

22 Claims, 46 Drawing Sheets

(56) References Cited

OTHER PUBLICATIONS

Kneipp et al., "Novel optical nanosensors for probing and imaging live cells," Nanomedicine: NBM, vol. 6, pp. 214-226 (2010).
Keren et al., "Noninvasive molecular imaging of small living subjects using Raman spectroscopy," PNAS, vol. 105, No. 15, pp. 5844-5849 (Apr. 15, 2008).
Lin et al., "A new protein A assay based on Raman reporter labeled immunogold nanoparticles," Biosensors and Bioelectronics, vol. 24, pp. 178-183 (2008).
Lee et al., "Diversity-oriented fluorescence library approach for the discovery of sensors and probes," Molecular BioSystems, vol. 5, No. 5, pp. 411-421 (2009).
Lee et al., "Surface-enhanced Raman scattering imaging of HER2 cancer markers overexpressed in single MCF7 cells using antibody conjugated hollow gold nanospheres," Biosensors and Bioelectronics, vol. 24, pp. 2260-2263 (2009).
Liz-Marzan et al., "Synthesis of Nanosized Gold-Silica Core-Shell Particles," Langmuir, vol. 12, pp. 4329-4335 (1996).
McCarthy et al., "Targeted delivery of multifunctional magnetic nanoparticles," Nanomedicine, vol. 2, No. 2, pp. 153-167 (2007).
Medarova et al., "In vivo imaging of siRNA delivery and silencing in tumors," Nature Medicine, vol. 13, No. 3, pp. 372-377 (Mar. 2007).
Nie et al., "Nanotechnology Applications in Cancer," Annual Review of Biomedical Engineering, vol. 9, pp. 257-288 (2008).
Park et al., "SERS imaging of HER2-overexpressed MCF7 cells using antibody-conjugated gold nanorods," Physical Chemistry Chemical Physics, vol. 11, pp. 7444-7449 (2009).
Qian et al., "Surface-Enhanced Raman Nanoparticie Beacons Based on Bioconjugated Gold Nanocrystals and Long Range Plasmonic Coupling," Journal of American Chemical Society, vol. 130, pp. 14934-14935 (2008).
Qian et al., "Stimuli-Responsive SERS Nanoparticles: Conformational Control of Plasmonic Coupling and Surface Raman Enhancement," Journal of American Chemical Society, vol. 131, pp. 7540-7541 (2009).
Qian et al., "In vivo tumor targeting and spectroscopic detection with surface-enhanced Raman nanoparticle tags," Nature Biotechnology, vol. 26, No. 1, pp. 83-90 (Jan. 2008).
Rosi et al., "Nanostructures in Biodiagnostics," Chemical Reviews, vol. 105, pp. 1547-1562 (2005).
Schlucker, "SERS Microscopy: Nanoparticle Probes and Biomedical Applications," ChemPhysChem, vol. 10, pp. 1344-1354 (2009).
Sha et al., "Surface-Enhanced Haman Scattering Tags for Rapid and Homogeneous Detection of Circulating Tumor Cells in the Presence of Human Whole Blood," Journal of American Chemical Society, vol. 130, pp. 17214-17215 (2008).
Sanles-Sobrido et al., "Design of SERS-Encoded, Submicron, Hollow Particles Through Confined Growth of Encapsulated Metal Nanoparticles," Journal of American Chemical Society, vol. 131, pp. 2699-2705 (2009).
Torchilin. "Micellar Nanocarriers: Pharmaceutical Perspectives," Pharmaceutical Research, vol. 24, No. 1, pp. 1-16 (Jan. 2007).
Woodle, "Nanoparticles deliver RNAi therapy," NanoToday. vol. 8, pp. 34-41 (Aug. 2005).
Woo et al., "Multiplex Immunoassay Using Fluorescent-Surface Enhanced Raman Spectroscopic Dots for the Detection of Bronchioalveolar Stem Cells in Murine Lung," Analytical Chemistry, vol. 81, No. 3, pp. 1008-1015 (Feb. 1, 2009).
Yu et al., "Multiplex Targeting, Tracking, and Imaging of Apoptosis by Fluorescent Surface Enhanced 28 Raman Spectroscopic Dots," Bioconjugate Chemistry, vol. 18, pp. 1155-1162 (2007).
Yang et al., "Single Chain Epidermal Growth Factor Receptor Antibody Conjugated Nanoparticles for 29 in vivo Tumor Targeting and Imaging," Small, vol. 5, No. 2, pp. 235-243 (2009).
Zavaleta et al., "Multiplexed imaging of surface enhanced Raman scattering nanotags in living mice using noninvasive Raman spectroscopy," PNAS, vol. 126, No. 32, pp. 13511-13516 (Aug. 11, 2009).
Zhang et al., "ErbB receptors: from oncogenes to targeted cancer therapies," The Journal of Clinical Investigation, vol. 117, No. 8, pp. 2051-2058 (Aug. 2007).
Zhang et al., "Surface-Enhanced Raman Scattering inside Metal Nanoshells," Journal of American Chemical Society, vol. 131, pp. 3808-3809 (2009).
Kudelski, "Raman studies of rhodamine 6G and crystal violet submonolayers on electrochemically roughened silver substrates: Do dye molecules adsorb preferentially on highly SERS-active sites?" Chemical Physical Letters, vol. 414, pp. 271-275 (2005).
Pieczonka et al., "Single molecule analysis by surfaced-enhanced Raman scattering," Chemical Society Reviews, vol. 37, pp. 946-954 (2008).
Kneipp et al., "Single-Molecule Detection of a Cyanine Dye in Silver Colloidal Solution Using Near-Infrared Surface-Enhanced Raman Scattering," Applied Spectroscopy, vol. 52, No. 2, pp. 175-178 (1998).
Song et al., "Highly sensitive immunoassay based on Raman reporter-labeled immune-Au aggregates and SERS-active immune substrate." Biosensors and Bioelectronics, vol. 25, pp. 826-831 (2009).
Wu et al., "Label-free biosensing of a gene mutation using a silicon nanowire field-effect transistor," Biosensors and Bioelectronics, vol. 25, pp. 820-825 (2009).
Maiti et al., "Development of biocompatible SERS nantog with increased stability by chemisorption of reporter molecule for in vivo cancer detection", Biosensors and Bioelectronics 26 (2010) 398-403.

\* cited by examiner

Y Building block (S1)

W building block

(C) (iii)

(F) (ii)

(G) (ii)

(H) (iii)

(I) (ii)

(I) (iii)

(K) (ii)

(L)

(a)

(b)

(a)

(b)

SURFACE ENHANCED RAMAN SPECTROSCOPY (SERS) COMPOUNDS AND METHODS OF THEIR PREPARATION

CROSS-REFERENCE TO RELATED APPLICATION

This application makes reference to and claims the benefit of priority of an application for "SERS Reporters Based On Triphenylmethine Core Structure With Sensitivity And Stability And Process For The Preparation Thereof" filed on Oct. 12, 2010, with the United States Patent And Trademark Office, and there duly assigned Ser. No. 61/392,044. The content of said application filed on Oct. 12, 2010, is incorporated herein by reference in its entirety for all purposes.

TECHNICAL FIELD

The invention lies in the field of spectroscopy and molecular diagnostics. In particular, the invention refers to a compound, a method and device for detecting an analyte using Surface Enhanced Raman Spectroscopy (SERS), and a method for producing the compound.

BACKGROUND

Vibrational spectroscopic techniques, such as infra-red (IR), normal Raman Spectroscopy and Surface Enhanced Raman Spectroscopy (SERS), have been considered for analyte detection. Of these, SERS has evolved as one of the most sensitive techniques for analyte detection due to enhancement of the Raman spectral intensity by interaction of the adsorbed SERS active analyte molecules with the surface of a metal substrate.

In SERS, the intensity of the vibrational spectra of a molecule is enhanced by several orders of magnitude when the molecule is in close proximity to metallic nanoparticles such as gold and silver. SERS has been successfully applied for labeling biological systems even in cells and tissues to sense multiplexed biomarkers. Nanoparticle tags that use SERS, herein referred as SERS-nanotags, to generate detectable Raman signals have been shown to be a successful alternative to fluorescence labeling, which has the drawbacks of photobleaching, peaks overlapping in multiplexed experiments, and inability to function in some extreme environments in biological systems.

Current state of the art SERS nanotags include immobilizing a Raman active dye (Raman reporter) on a metal colloid followed by bioconjugation to target specific locations. Such a nanoparticle—Raman reporter assembly is called a Raman tag in analogy with quantum dots and can provide a platform for multiplexing, targeting and tracking in bioimaging and sensing applications.

The types of reporter molecules and metal nanoparticles are major determinants of the sensitivity of a Raman tag. Among the different reporter molecules, triphenylmethine (TM) compounds exhibit absorption at visible ranges that allows the compounds to be a useful Raman reporter in visible-near infrared (visible-NIR) excitation. Although a few TM compounds, such as malachite green isothiocyanate (MGITC) and crystal violet (CV), have been used as reporters, there remains a need for reporter molecules which generate higher SERS intensities and are easily identifiable within a multiplexed analysis platform.

In view of the above, there is a need for an improved compound that can be used for detecting an analyte using SERS, as well as improved methods for forming it.

SUMMARY OF THE INVENTION

In a first aspect, the invention refers to a compound having Formula I:

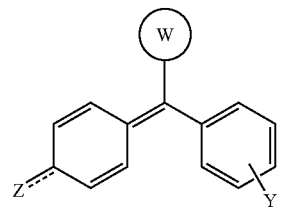

Formula I wherein
W is selected from the group consisting of an optionally substituted aryl group and an optionally substituted heteroaryl group;
each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms; ═══ is used to denote a single bond or a double bond; and Z is NH, $NH_2$, NH—(C═O)—$(CH_2)_n$—SH, wherein n=1 to 10, or or a tautomer or stereoisomer thereof, or a salt thereof.

In a second aspect, the invention refers to a method of producing a compound according to the first aspect, comprising reacting a compound represented by the general Formula II with an acid-labile resin, and subsequent reaction with a compound represented by the general Formula III Formula II Formula III wherein
each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms; W is selected from the group consisting of an optionally substituted aryl group and an optionally substituted heteroaryl group; and X is a magnesium halide.

In a third aspect, the invention refers to a SERS marker conjugate comprising a nanoparticle and a Raman-active marker compound according to the first aspect attached to the nanoparticle surface.

In a fourth aspect, the invention refers to a biosensor comprising a plurality of the SERS marker conjugates according to the third aspect.

In a fifth aspect, the invention refers to a method for the detection of any analyte using the SERS marker conjugate according to the third aspect or a biosensor according to the fourth aspect.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE INVENTION

Figure 1A:
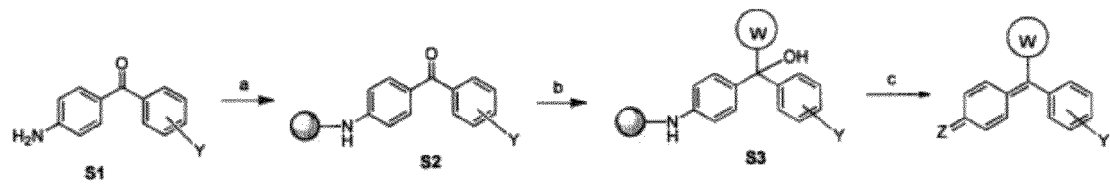
FIG. 1A is a general scheme showing the synthesis of triphenylmethine (TM) compounds according to embodiments of the invention. Embodiments of the chemical structure of the Y building blocks S1 (Intermediates A to D) and W building blocks represented by compounds 1 to 29 are also shown in FIG. 1A. Intermediate A was commercially available from Aldrich. Intermediates B to D were synthesized according to the procedures outlined in Examples 2 to 4. Each intermediate A to D was respectively loaded on an acid-labile resin such as 2-chlorotrityl chloride resin in Step a), and reacted with 29 different Grignard reagents (W building block) in Step b) (see Examples 5 and 6). Step c) comprises an acidic cleavage from the acid-labile resin using an acid such as 1% trifluoroacetic acid (TFA) (see Example 7). Step c) may further comprise addition of a compound such as lipoic acid, which allows for chemisorption of the compounds on nanoparticles to form SERS marker conjugates.
Figure 1A:
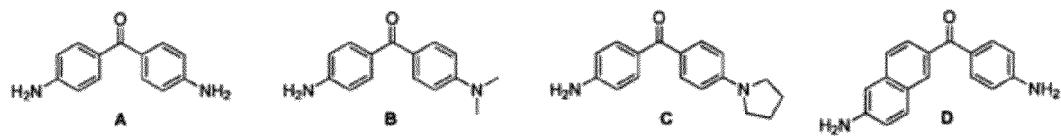
Figure 1A:
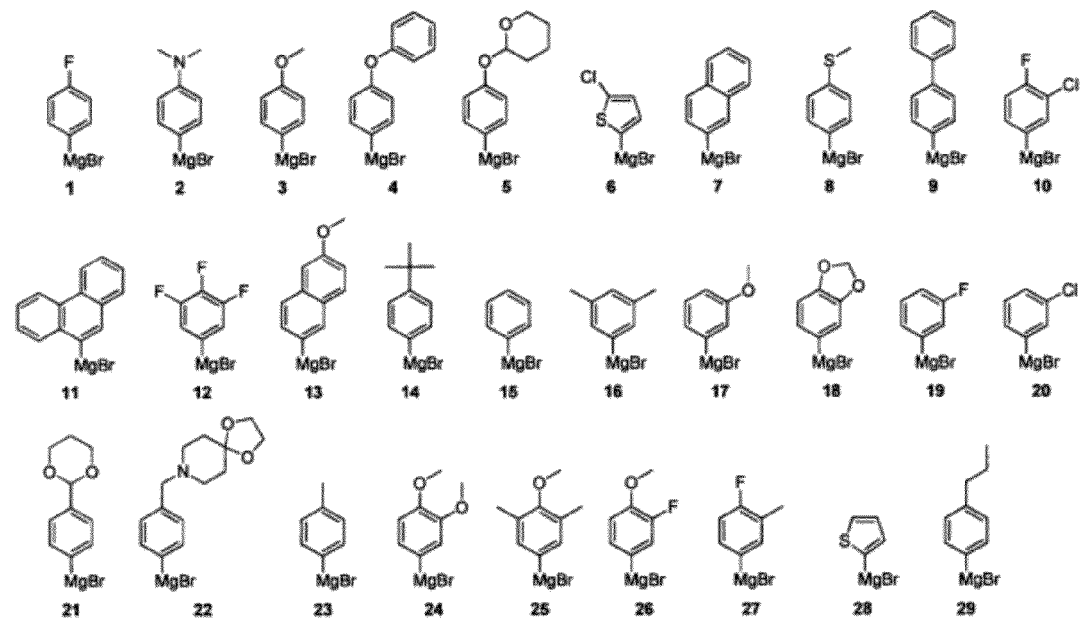
Figure 1B:
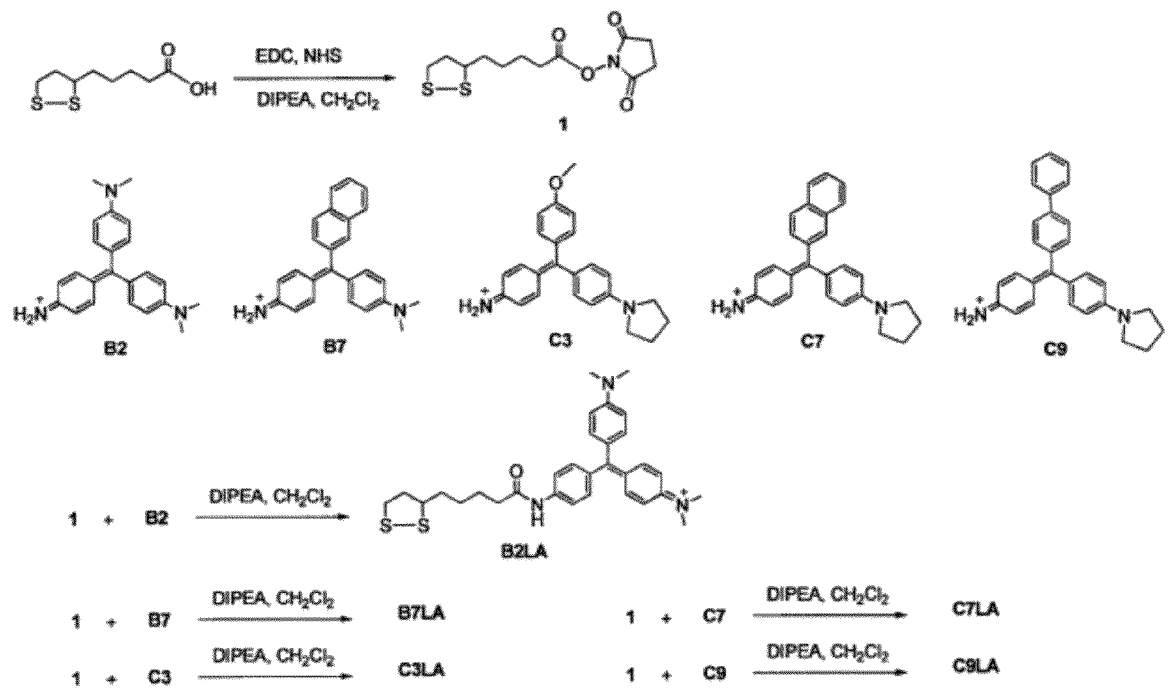
FIG. 1B is a general scheme showing the synthesis of triphenylmethine-lipoic acid (TM-LA) compounds by amide coupling of TM compounds with lipoic acid according to embodiments of the invention.
Figure 1C:
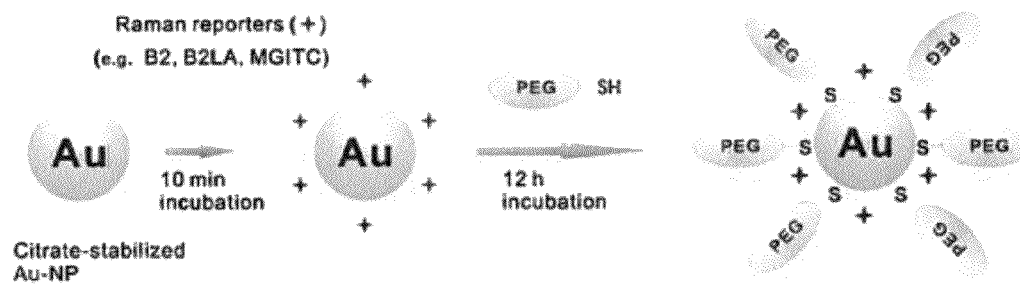
FIG. 1C is a general schematic diagram for the preparation of polyethylene glycol (PEG) encapsulated SERS nanotag.

In a first aspect, the invention refers to a compound having Formula I:

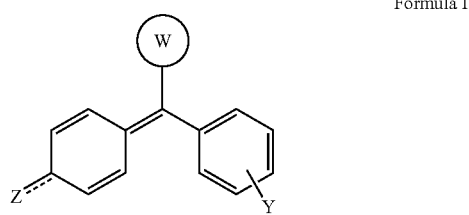

Formula I wherein W is selected from the group consisting of an optionally substituted aryl group and an optionally substituted heteroaryl group; each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms, ===== is used to denote a single bond or a double bond, and Z is NH, $NH_2$, NH—(C=O)—$(CH_2)_n$—SH, wherein n=1 to 10, or

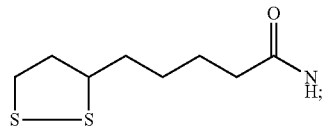

or a tautomer or stereoisomer thereof, or a salt thereof.

Surface Enhanced Raman Spectroscopy, or Surface Enhanced Raman Scattering, abbreviated SERS, is a surface sensitive technique that results in the enhancement of Raman scattering by molecules adsorbed on metal surfaces. The enhancement factor can be as much as $10^{14}$ to $10^{15}$, which allows the technique to be sensitive enough to detect single molecules.

The compounds according to various embodiments of the invention are Raman reporters, i.e. compounds which have a high Raman cross section and the Raman vibrational "finger print" is detectably altered, for example by a shift and/or an increase in intensity, upon the binding an analyte, such as to allow detection and quantitation of the analyte. Accordingly, the compounds are also known as Raman-active marker compounds, and can be considered to represent reporters or receptors of the analyte.

In various embodiments, W is an optionally substituted aryl group or an optionally substituted heteroaryl group. An "aryl" group as used herein refers to an all-carbon monocyclic or fused-ring polycyclic (i.e., rings which share adjacent pairs of carbon atoms) groups of 6 to 14 ring atoms and having a completely conjugated pi-electron system. Examples, without limitation, of aryl groups are phenyl, naphthenyl, anthracenyl and phenanthrenyl. The aryl group is optionally substituted, i.e. it may be substituted or unsubstituted. When substituted, the substituted group(s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, C-carboxy, O-carboxy, nitro, silyl, sulfinyl, sulfonyl, amino, and —$NR^3R^4$ where $R^3$ and $R^4$ are independently selected from the group consisting of hydrogen, $C_1$-$C_4$ alkyl, $C_3$-$C_8$ cycloalkyl, $C_6$-$C_{14}$ aryl, carbonyl, acetyl, sulfonyl, amino, and trifluoromethanesulfonyl, or $R^3$ and $R^4$, together with the nitrogen atom to which they are attached, combine to form a five- or six-membered heteroalicyclic ring.

A "heteroaryl" group as used herein refers to a monocyclic or fused aromatic ring (i.e., rings which share an adjacent pair of atoms) of 5 to 10 ring atoms in which one, two, three or four ring atoms are selected from the group consisting of nitrogen, oxygen and sulfur and the rest being carbon. Examples, without limitation, of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnolinyl, napthyridinyl, quinolyl, isoquinolyl, tetrazolyl, 5,6,7,8-tetrahydroquinolyl, 5, 6, 7,8-tetra-hydroisoquinolyl, purinyl, pteridinyl, pyridinyl, pyrimidinyl, carbazolyl, xanthenyl or benzoquinolyl. The heteroaryl group may be substituted or unsubstituted. When substituted, the substituted group(s) is one or more, for example one or two substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, C-carboxy, O-carboxy, nitro, silyl, sulfinyl, sulfonyl, amino, and —$NR^3R^4$, with $R^3$ and $R^4$ as defined above.

As used herein, "alkyl" refers to a saturated aliphatic hydrocarbon including straight chain, or branched chain groups. Preferably, the alkyl group has 1 to 10 carbon atoms (whenever a numerical range; e.g., "1-10", is stated herein, it means that the group, in this case the alkyl group, may contain 1 carbon atom, 2 carbon atoms, 3 carbon atoms, etc. up to and including 10 carbon atoms). More specifically, it may be a medium size alkyl having 1 to 6 carbon atoms or a lower alkyl having 1 to 4 carbon atoms e.g., methyl, ethyl, n-propyl, isopropyl, butyl, iso-butyl, tert-butyl and the like. The alkyl group may be substituted or unsubstituted. When substituted, the substituent group(s) is one or more, for example one or two groups, individually selected from the group consisting of $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, C-carboxy, O-carboxy, nitro, silyl, sulfinyl, sulfonyl, amino, and —$NR^3R^4$ with $R^3$ and $R^4$ as defined above.

A "cycloalkyl" group refers to an all-carbon monocyclic ring (i.e., rings which share an adjacent pair of carbon atoms) of 3 to 8 ring atoms wherein one of more of the rings does not have a completely conjugated pi-electron system e.g., cyclopropyl, cyclobutyl, cyclopentyl, cyclohexyl, cyclobutenyl, cyclopentenyl, cyclohexenyl, and the like. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is one or more, for example one or two groups, individually selected from $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, C-carboxy, O-carboxy, nitro, silyl, sulfinyl, sulfonyl, amino, and —$NR^3R^4$, with $R^3$ and $R^4$ as defined above.

An "alkenyl" group refers to an alkyl group, as defined herein, consisting of at least two carbon atoms and at least one carbon-carbon double bond e.g., ethenyl, propenyl, butenyl or pentenyl and their structural isomeric forms such as 1- or 2-propenyl, 1-, 2-, or 3-butenyl and the like.

An "alkynyl" group refers to an alkyl group, as defined herein, consisting of at least two carbon atoms and at least one carbon-carbon triple bond e.g., acetylene, ethynyl, propynyl, butynyl, or pentynyl and their structural isomeric forms as described above.

A "heteroalicyclic" group refers to a monocyclic or fused ring of 5 to 10 ring atoms containing one, two, or three heteroatoms in the ring which are selected from the group consisting of nitrogen, oxygen and —$S(O)_n$ where n is 0-2, the remaining ring atoms being carbon. The rings may also have one or more double bonds. However, the rings do not have a completely conjugated pi-electron system. Examples, without limitation, of heteroalicyclic groups are pyrrolidine, piperidine, piperazine, morpholine, imidazolidine, tetrahydropyridazine, tetrahydrofuran, thiomorpholine, tetrahydropyridine, and the like. The heteroalicyclic ring may be substituted or unsubstituted. When substituted, the substituted group (s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, C-carboxy, O-carboxy, nitro, silyl, sulfinyl, sulfonyl, amino, and —$NR^3R^4$, with $R^3$ and $R^4$ as defined above.

A "hydroxy" group refers to an —OH group.

An "alkoxy" group refers to an —O-unsubstituted alkyl and —O-substituted alkyl group, as defined herein. Examples include and are not limited to methoxy, ethoxy, propoxy, butoxy, and the like.

A "cycloalkoxy" group refers to a —O-cycloalkyl group, as defined herein. One example is cyclopropyloxy.

An "aryloxy" group refers to both an —O-aryl and an —O-heteroaryl group, as defined herein. Examples include and are not limited to phenoxy, naphthyloxy, pyridyloxy, furanyloxy, and the like.

A "mercapto" group refers to a —SH group.

An "alkylthio" group refers to both an S-alkyl and an —S-cycloalkyl group, as defined herein. Examples include and are not limited to methylthio, ethylthio, and the like.

An "arylthio" group refers to both an —S-aryl and an —S-heteroaryl group, as defined herein. Examples include and are not limited to phenylthio, naphthylthio, pyridylthio, furanylthio, and the like.

A "sulfinyl" group refers to a —S(O)—R' group, wherein, R' is selected from the group consisting of hydrogen, hydroxy, alkyl, cycloalkyl, aryl, heteroaryl (bonded through a ring carbon) and heteroalicyclic (bonded through a ring carbon), as defined herein.

A "sulfonyl" group refers to a —$S(O)_2R'$ group with R' is selected from the group consisting of hydrogen, hydroxy, alkyl, cycloalkyl, aryl, heteroaryl (bonded through a ring carbon) and heteroalicyclic (bonded through a ring carbon), as defined herein.

A "trihalomethyl" group refers to a —$CX_3$ group wherein X is a halo group as defined herein e.g., trifluoromethyl, trichloromethyl, tribromomethyl, dichlorofluoromethyl, and the like.

"Carbonyl" refers to a —C(=O)—R' group, where R' is selected from the group consisting of hydrogen, alkyl, cycloalkyl, aryl, heteroaryl (bonded through a ring carbon) and heteroalicyclic (bonded through a ring carbon), as defined herein. Representative examples include and the not limited to acetyl, propionyl, benzoyl, formyl, cyclopropylcarbonyl, pyridinylcarbonyl, pyrrolidin-1-ylcarbonyl, and the like.

A "thiocarbonyl" group refers to a —C(=S)—R' group, with R' as defined herein.

"C-carboxy" and "carboxy" which are used interchangeably herein refer to a —C(=O)O—R'' group, with R'' as defined herein, e.g. —COOH, methoxycarbonyl, ethoxycarbonyl, benzyloxycarbonyl, and the like.

An "O-carboxy" group refers to a —OC(=O)R' group, with R' as defined herein, e.g. methylcarbonyloxy, phenylcarbonyloxy, benzylcarbonyloxy, and the like.

An "acetyl" group refers to a —C(=O)$CH_3$ group.

A "carboxylic acid" group refers to a C-carboxy group in which R' is hydrogen.

A "halo" or "halogen" group refers to fluorine, chlorine, bromine or iodine.

A "cyano" group refers to a —CN group.

A "nitro" group refers to a —$NO_2$ group.

An "amino" group refers to an —$NR^5R^6$ group, wherein $R^5$ and $R^6$ are independently hydrogen or unsubstituted lower alkyl, e.g., —$NH_2$, dimethylamino, diethylamino, ethylamino, methylamino, and the like.

According to various embodiments of the invention, W may be one of

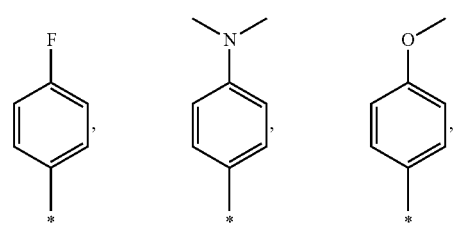
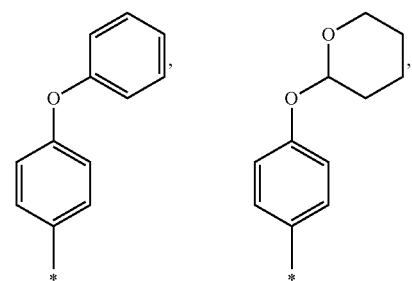
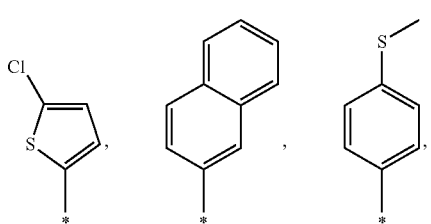
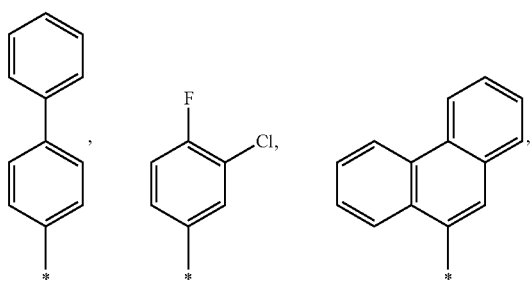
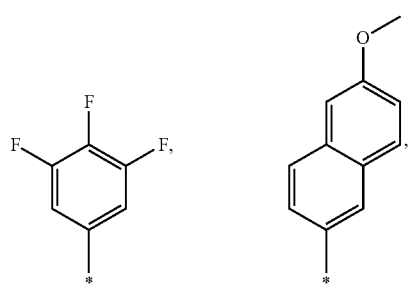
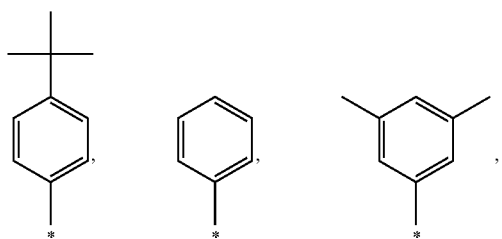
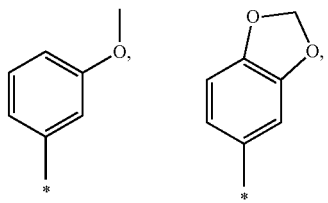
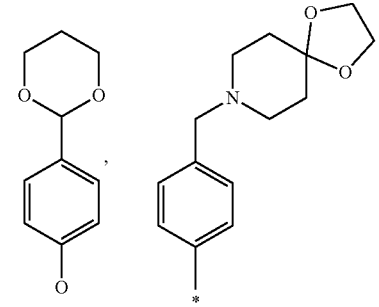
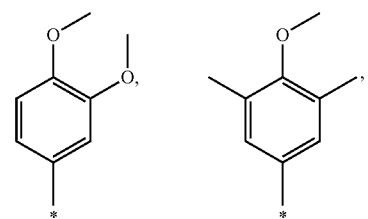
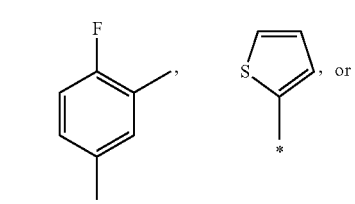
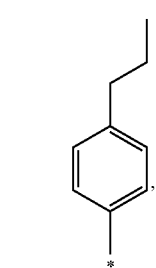
wherein the symbol "*" denotes the point at which W may be connected to the remainder of the compound of Formula I.
In various embodiments, W is one of
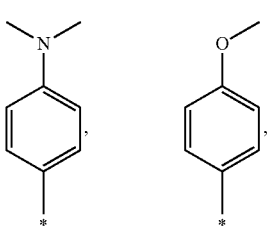

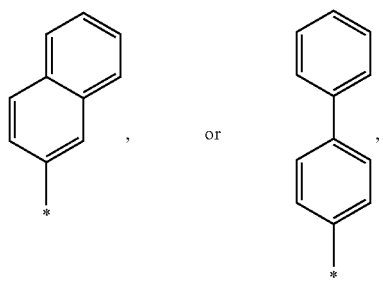

Referring to the compound of Formula I, each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms. In various embodiments, Y is in the p-position of the aromatic (phenyl) ring. In certain embodiments of the compounds, Y is selected from $N(CH_3)_2$ or $N(CH_2)_4$.

In various embodiments, the moiety Z may be NH, $NH_2$, $NH-(C=O)-(CH_2)_n-SH$, wherein n=1 to 10, or

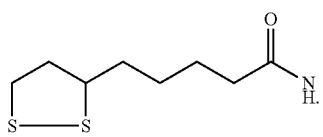

The moiety Z may be bound to the remainder of the compound of Formula I by a single bond or a double bond via its N group. When Z is bound by a single bond to the remainder of the compound of Formula I, for example, Z may be $NH_2$ or

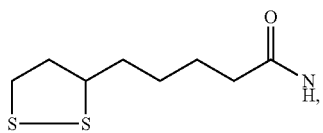

When Z is bound by a double bond to the remainder of the compound of Formula I, for example, Z may be NH.

In certain embodiments of the compounds, Y is $N(CH_3)_2$ and W is

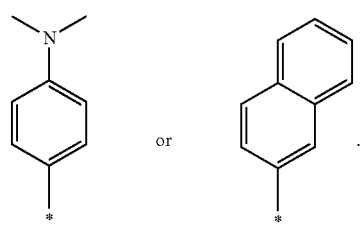

In further embodiments, Y is $N(CH_2)_4$ and W is

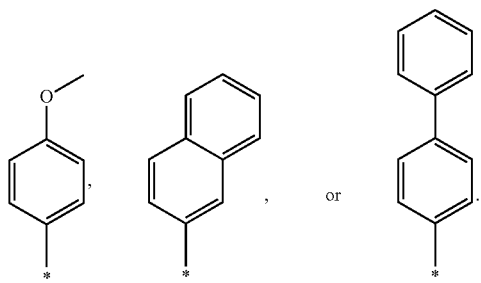

In yet further embodiments, the compound of general Formula I may be

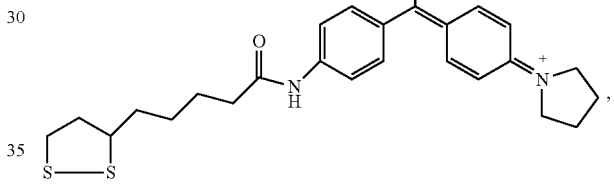

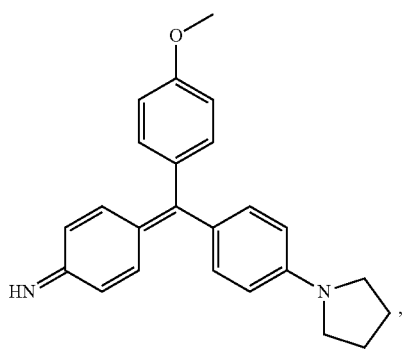

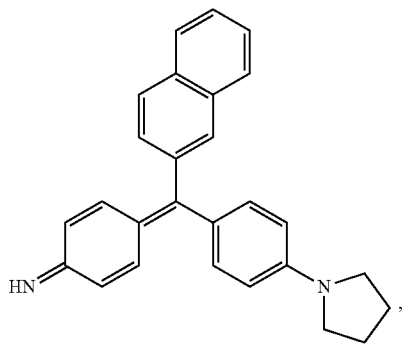

-continued

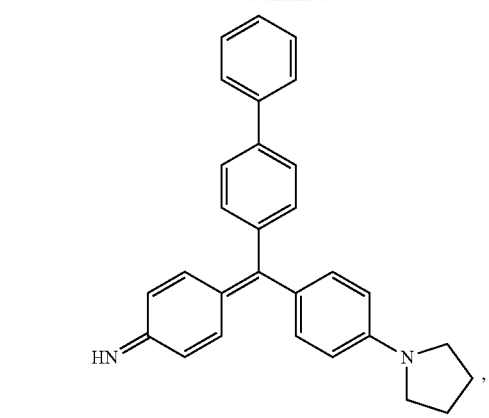

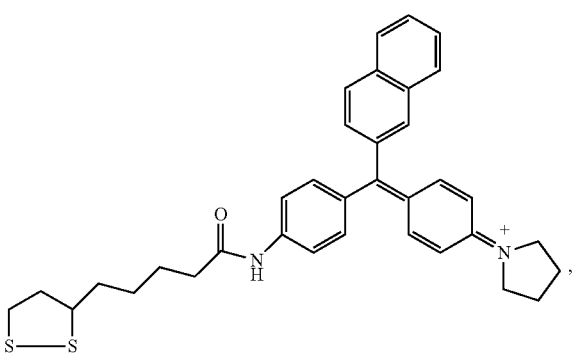

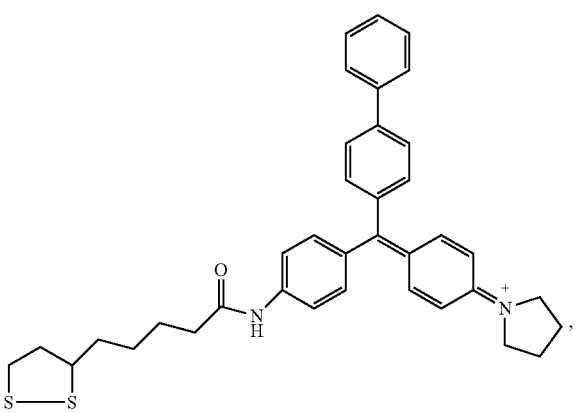

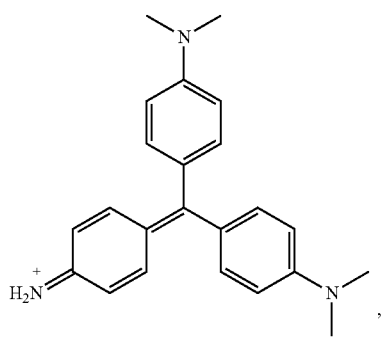

-continued

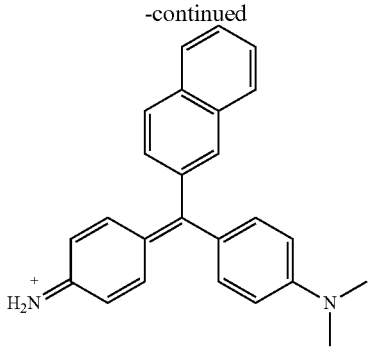

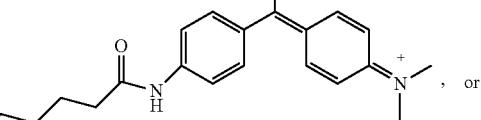, or

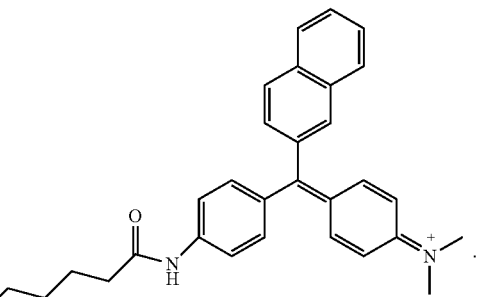

All the above compounds of the invention are useful as Raman reporters in the SERS technique, in particular the SERS-based detection methods of the invention.

The invention also relates to a method of producing a compound according to the first aspect, comprising reacting a compound represented by the general Formula II with an acid-labile resin, and subsequent reaction with a compound represented by the general Formula III

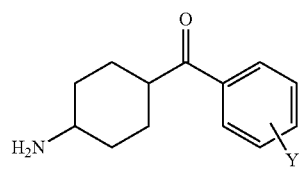

Formula II

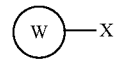

Formula III wherein
each Y independently is $NR^1R^2$, wherein $R^1$ and $R^2$ are independently selected from the group consisting of H and $C_1$-$C_6$ alkyl, or $R^1$ and $R^2$ combine to form together with the nitrogen to which they are attached a heterocyclic group with 4 to 5 carbon atoms; W is selected from the group consisting of an optionally substituted aryl group and an optionally substituted heteroaryl group; and X is a magnesium halide.

In various embodiments, a compound of general Formula II may be dissolved in a suitable solvent, such as dichloromethane. In some cases, a second solvent such as dimethylformamide may optionally or additionally be used in order to dissolve the compound. The resulting solution may be added to an acid-labile resin. The term "acid-labile" refers to a molecular segment containing at least one covalent bond that is cleaved upon exposure to acid, while the term "resin" refers to a solid support useful for solid phase synthesis. Accordingly, an "acid-labile resin" refers to a solid support containing at least one covalent bond that may be cleaved by an acid. Examples of an acid-labile resin that may be used include, but are not limited to, trityl resins such as 2-chlorotrityl chloride resin, p-alkoxybenzylalcohol resins such as PL-Wang-Br resin, phenylacetamidomethyl (PAM) resins, merrifield alpha-methoxyphenyl (MAMP) resins such as PL-MAMP-OH resin, 4-hydroxymethylpolystyrene resin (PL-HMS), chloromethylpolystyrene resin (PL-CMS), p-bromostyrene resin (PL-PBS), and 4-hydroxymethylbenzoic acid AMS resin (PL-HMBA).

The compound having Formula II may be reacted with one or more functional groups present on the acid-labile resin to form a covalent bond. In some embodiments, the acid-labile resin is 2-chlorotrityl chloride resin, which may be obtained from 2-chlorotrityl alcohol resin. The 4-aminophenyl group according to the compound having Formula II may allow linking of the compound to the 2-chlorotrityle chloride resin.

In various embodiments, a compound of general Formula III is subsequently added. The compound of general Formula III is also herein referred as a Grignard reagent. W may be selected from the group consisting of an optionally substituted aryl group and an optionally substituted heteroaryl group. Possible moieties for W have already been discussed herein. The method of the invention may further comprise an acidic cleavage from the acid-labile resin. X may be a magnesium halide, such as MgI, MgBr, and MgCl, and may be connected to W via the Mg atom. By using a solid phase chemistry approach to fabricate the compound according to various embodiments of the present invention, the use of toxic reagents and time-consuming purification steps may be avoided.

The method of the present invention may further comprise reacting the compound formed above with a compound selected from lipoic acid, di-hydrolipoic acid and SH—$(CH_2)_n$—$CO_2H$, in which n=1-10. The compound, such as lipoic acid, may be covalently bonded or conjugated to the compound. In various embodiments, lipoic acid is used. The lipoic acid may act as an anchoring molecule between the nanoparticle, such as gold or silver nanoparticle, and the compound. Through the use of lipoic acid, the dye compounds may be chemisorpted to the nanoparticle, and which may result in a more stable SERS intensity measurement.

In a third aspect, the invention refers to a SERS marker conjugate comprising a nanoparticle and a Raman-active marker compound according to the first aspect attached to the nanoparticle surface.

The SERS marker conjugate is also referred herein as a nanotag or a SERS nanotag. The term "conjugate" as used herein refers to two or more molecules which have been linked together. The linkage to each other may be covalent or non-covalent. The Raman-active marker compounds according to the first aspect may be stably adsorbed at a surface that enhances the Raman signal from the compound, such as a nanoparticle or other SERS active substrate surface by reversible electrostatic interaction, hydrophobic interaction or covalent anchoring, to form the SERS marker conjugate. "Electrostatic attraction" relates to attachment via salt bridges, hydrogen bonds and polar interactions, for example if the surface is charged negative and the compound bears a positive charge or vice versa. "Hydrophobic interaction" includes the interaction between uncharged and non-polar groups.

Ideally, the compound has a high Raman cross section and the capability to adsorb strongly on the surface of a metal nanoparticle in aqueous media so that it gives a fast and intense and non fluctuating SERS signal that is proportional to the concentration of the analyte in bulk.

In some embodiments, the SERS marker conjugate further comprises an analyte-binding molecule coupled to the Raman-active marker compound. The term "analyte binding molecule" as used herein refers to any molecule capable of binding to an analyte of choice so as to form a complex consisting of the analyte binding molecule and the analyte. In one embodiment of such a conjugate, the analyte binding molecule is covalently coupled to the Raman-active marker compound, which is in turn covalently attached to the nanoparticle surface. Preferably, the binding between the analyte binding molecule to the analyte molecule is specific so that a specific complex between analyte and analyte binding molecule is formed.

"Specifically binding" and "specific binding" as used herein mean that the analyte binding molecule binds to the target analyte based on recognition of a binding region or epitope on the target molecule. The analyte binding molecule preferably recognizes and binds to the target molecule with a higher binding affinity than it binds to other compounds in the sample. In various embodiments of the invention, "specifically binding" may mean that an antibody or other biological molecule, binds to a target molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the analyte binding molecule uniquely recognizes and binds to the target analyte.

The analyte binding molecule may be a proteinaceous molecule, such as an antibody, for example a monoclonal or polyclonal antibody, which immunologically binds to the target analyte at a specific determinant or epitope. The term "antibody" is used in the broadest sense and specifically covers monoclonal antibodies as well as antibody variants, fragments or antibody like molecules, such as for example, Fab, F(ab')$_2$, scFv, Fv diabodies and linear antibodies, so long as they exhibit the desired binding activity.

In some embodiments, the analyte binding molecule is a monoclonal antibody. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies can include "chimeric" antibodies and humanized antibodies. A "chimeric" antibody is a molecule in which different portions are derived from different animal species, such as those having a variable region derived from a murine mAb and a human immunoglobulin constant region.

Monoclonal antibodies may be obtained by any technique that provides for the production of antibody molecules by continuous cell lines in culture. These include, but are not limited to the hybridoma technique of Koehler and Milstein (U.S. Pat. No. 4,376,110), the human B-cell hybridoma technique, and the EBV-hybridoma technique. Such antibodies may be of any immunoglobulin class including IgG, IgM, IgE, IgA, IgD and any subclass thereof. The hybridoma producing the mAb may be cultivated in vitro or in vivo. Production of high titres of mAbs in vivo makes this a very effective method of production.

In some embodiments of the invention, the analyte binding molecule is a polyclonal antibody. "Polyclonal antibodies" refer to heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

The terms "analyte", "target compound", "target molecule" or "target" as interchangeably used herein, refer to any substance that can be detected in an assay by binding to a binding molecule, and which, in one embodiment, may be present in a sample. Therefore, the analyte can be, without limitation, any substance for which there exists a naturally occurring antibody or for which an antibody can be prepared. The analyte may, for example, be an antigen, a protein, a polypeptide, a nucleic acid, a hapten, a carbohydrate, a lipid, a cell or any other of a wide variety of biological or non-biological molecules, complexes or combinations thereof. Generally, the analyte will be a protein, peptide, carbohydrate or lipid derived from a biological source such as bacterial, fungal, viral, plant or animal samples. Additionally, however, the target may also be a small organic compound such as a drug, drug-metabolite, dye or other small molecule present in the sample.

The term "sample", as used herein, refers to an aliquot of material, frequently biological matrices, an aqueous solution or an aqueous suspension derived from biological material. Samples to be assayed for the presence of an analyte by the methods of the present invention include, for example, cells, tissues, homogenates, lysates, extracts, and purified or partially purified proteins and other biological molecules and mixtures thereof.

Non-limiting examples of samples typically used in the methods of the invention include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed. The samples used in the methods of the present invention will vary based on the assay format and the nature of the tissues, cells, extracts or other materials, especially biological materials, to be assayed. Methods for preparing protein extracts from cells or samples are well known in the art and can be readily adapted in order to obtain a sample that is compatible with the methods of the invention. Detection in a body fluid can also be in vivo, i.e. without first collecting a sample.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 20 to 1000 amino acids in length, more typically at least about 100 to 600 amino acids, and frequently at least about 200 to about 500 amino acids. Included are homo-polymers of one specific amino acid, such as for example, poly-lysine. "Proteins" include single polypeptides as well as complexes of multiple polypeptide chains, which may be the same or different.

Multiple chains in a protein may be characterized by secondary, tertiary and quaternary structure as well as the primary amino acid sequence structure, may be held together, for example, by disulfide bonds, and may include post-synthetic modifications such as, without limitation, glycosylation, phosphorylation, truncations or other processing.

Antibodies such as IgG proteins, for example, are typically comprised of four polypeptide chains (i.e., two heavy and two light chains) that are held together by disulfide bonds. Furthermore, proteins may include additional components such associated metals (e.g., iron, copper and sulfur), or other moieties. The definitions of peptides, polypeptides and proteins includes, without limitation, biologically active and inactive forms; denatured and native forms; as well as variant, modified, truncated, hybrid, and chimeric forms thereof.

The terms "contacting" or "incubating" as used interchangeably herein refer generally to providing access of one component, reagent, analyte or sample to another. For example, contacting can involve mixing a solution comprising an analyte binding protein or conjugate thereof with a sample. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples.

The term "detecting" as used herein refers to a method of verifying the presence of a given molecule. The technique used to accomplish this is surface enhanced Raman spectroscopy (SERS). The detection may also be quantitative, i.e. include correlating the detected signal with the amount of analyte. The detection includes in vitro as well as in vivo detection.

The method of the invention can also be a multiplex method for detecting more than one analyte, i.e. two or more different analytes. This usually requires the use of more than one analyte binding molecule in the contacting step so that each analyte is bound by a specific analyte binding molecule. The signal obtained from a multitude of different analyte binding molecule:analyte complexes can be resolved by using different Raman-active linker molecules that produce distinct SERS signals.

The Raman-active marker compound according to various embodiments of the invention may be attached to the surface of a nanoparticle to form the SERS marker conjugate. "Nanoparticle" as used herein relates to a particle sized between 1 and 100 nanometers, such as 10, 20, 30, 40, 50, 60, 70, 80, or 90 nm. Methods for the production of nanoparticles are well-known in the art and include sol-gel processes. The nanoparticle may be coated with or consist of a noble metal, or copper. "Noble metal", as used herein, relates to a metal selected from the group consisting of ruthenium, rhodium, silver, palladium, osmium, iridium, platinum, and gold, preferably silver and gold. For example, the nanoparticles may be made of plastic, ceramics, composites, glass or organic polymers and coated with the metal of choice, such as silver or gold. In some embodiments, the nanoparticle may be a citrate-stabilized gold nanoparticle.

In various embodiments, the SERS marker conjugate may further comprise a material selected from silica ($SiO_2$), bovineserum albumin (BSA) cross linked with glutaraldehyde, thiolated DNA, and thiolated polyethylene glycol (PEG). In some embodiments, the material is PEG. The material, for example PEG, may form a layer around the conjugate, thereby encapsulating the conjugate. In some embodiments, gold nanoparticles are used. In such cases, the thiolated PEG may be covalently bonded to the surface of the gold nanoparticles via the thiol group on the PEG molecules. The PEG layer may serve to protect the SERS marker conjugate from aggregation in aqueous media, and may result in stable SERS intensities during measurement.

These conjugates can be part of a kit for the detection of a given analyte or the conjugate components can, together with coupling agents, form part of a kit, requiring that before use, the conjugate is formed.

In a further aspect, the invention relates to a biosensor for the detection of an analyte using surface-enhanced Raman spectroscopy, comprising one or more of the above conjugates. The biosensor may further comprise a substrate with the nanoparticles being attached to or adherent to the substrate. The biosensor can be configured for in vivo and/or in vitro use. The use of such a biosensor may be in vivo or in vitro. The invention also relates to a method for the detection of an analyte using the SERS marker conjugate or the biosensor described herein. The method may comprise contacting the SERS marker conjugate or the biosensor with the analyte containing medium, for example a sample or body fluid, and detecting the SERS signal from the sensor. In some embodiments, the biosensor is configured for a multiplex method that allows the detection of more than one analyte.

The invention illustratively described herein may suitably be practiced in the absence of any element or elements, limitation or limitations, not specifically disclosed herein. Thus, for example, the terms "comprising", "including", "containing", etc. shall be read expansively and without limitation.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

FIG. 1A is a general scheme showing the synthesis of triphenylmethine (TM) compounds according to embodiments of the invention. Embodiments of the chemical structure of the Y building blocks S1 (Intermediates A to D) and W building blocks represented by compounds 1 to 29 are also shown in FIG. 1A. Intermediate A was commercially available from Aldrich. Intermediates B to D were synthesized according to the procedures outlined in Examples 2 to 4. Each intermediate A to D was respectively loaded on an acid-labile resin such as 2-chlorotrityl chloride resin in Step a), and reacted with 29 different Grignard reagents (W building block) in Step b) (see Examples 5 and 6). Step c) comprises an acidic cleavage from the acid-labile resin using an acid such as 1% trifluoroacetic acid (TFA) (see Example 7). Step c) may further comprise addition of a compound such as lipoic acid, which allows for chemisorption of the compounds on nanoparticles to form SERS marker conjugates.

Synthesis of the triphenylmethine (TM) compounds according to an embodiment of the invention is described as follows in Scheme 1.

Scheme 1:

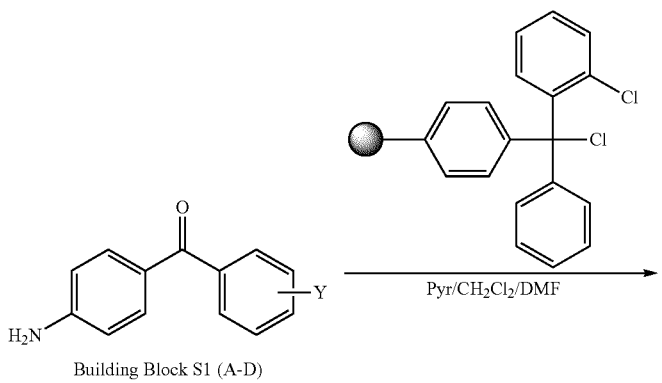

Building Block S1 (A-D)

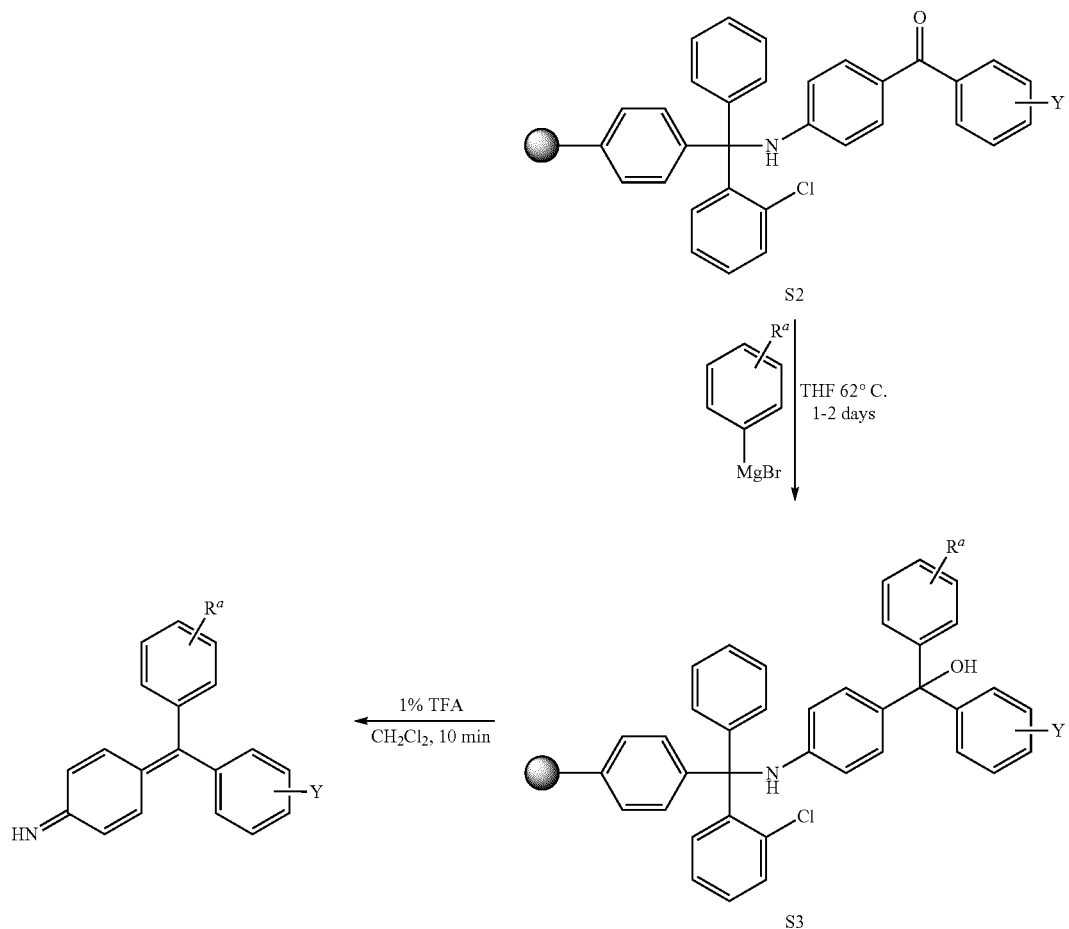

Referring to Scheme 1, each intermediate A to D was respectively loaded on 2-chlorotrityl chloride resin, and reacted with 29 different Grignard reagents ($R^a$ building block). Reagents and conditions: Step (a) 2-chlorotrityl chloride resin (1.37 mmol/g$^{-1}$), pyridine, dichloromethane (CH$_2$Cl$_2$), and dimethylformamide (DMF); Step (b) Grignard reagents, tetrahydrofuran (THF), 62° C.; Step (c) 1% trifluoroacetic acid (TFA), CH$_2$Cl$_2$. An acidic cleavage from the resin resulted in the dehydration of the corresponding tertiary alcohols, resulting in the fully conjugated TM derivatives. Use of the 4-aminophenyl group present on the Y building block (S1) has the advantages of providing a linker group to the resin and also of providing a reactive group to the metal surface in the final TM compound.

All the compounds were characterized by LCMS and 52 relatively pure compounds were selected for further studies with purity and characterization, as well as modification with thiolated PEG, as outlined in Examples 8 to 12.

In further embodiments, the five best TM compounds (B2, B7, C3, C7 and C9) in terms of highest SERS intensity were reacted with lipoic acid (LA) and contacted with noble metal nanoparticles to allow chemisorption of the compounds on the nanoparticles to form SERS marker conjugates (see Example 13). The SERS marker conjugates were characterized as well as modified with thiolated PEG as outlined in Examples 14 to 17.

Example 1

Chemicals and Analytical Equipments

Unless otherwise noted, all the chemicals and solvents were obtained from commercial suppliers (Acros and Aldrich) and used without further purification. 2-chlorotrityl alcohol resin (1.37 mmol/g) was purchased from BeadTech Inc., Korea. All the Grignard reagents were purchased from Aldrich or Rieke Metals, Inc.

All compounds were identified using a liquid chromatography-mass spectrometer (LC-MS) from Agilent Technology with a C18 column (20×4.0 mm), with 4 minutes elution using a gradient solution of acetonitrile-water (CH$_3$CN—H$_2$O) (containing 0.1% acetic acid), with ultraviolet (UV) detector and an electrospray ionization source. Nuclear Magnetic Resonance (NMR) spectra were recorded on a Bruker DPX 300 ($^1$H NMR at 300 MHz; $^{13}$C NMR at 75 MHz) spectrometer. High-resolution mass spectra were determined on a Finnigem MAT95XL-T instrument. Ultraviolet-Visible (UV-Vis) absorption spectra were recorded on HITACHI U-2900 spectrometer. The standard extraction work-up procedure includes pouring the reaction mixture into a excess amount of water, extracting with the organic solvent indicated, washing the combined extracts successively with water and brine, drying the extract over anhydrous sodium sulfate (Na$_2$SO$_4$) or magnesium sulfate (MgSO$_4$) and evaporating the solvent.

Example 2

Synthesis of intermediate B

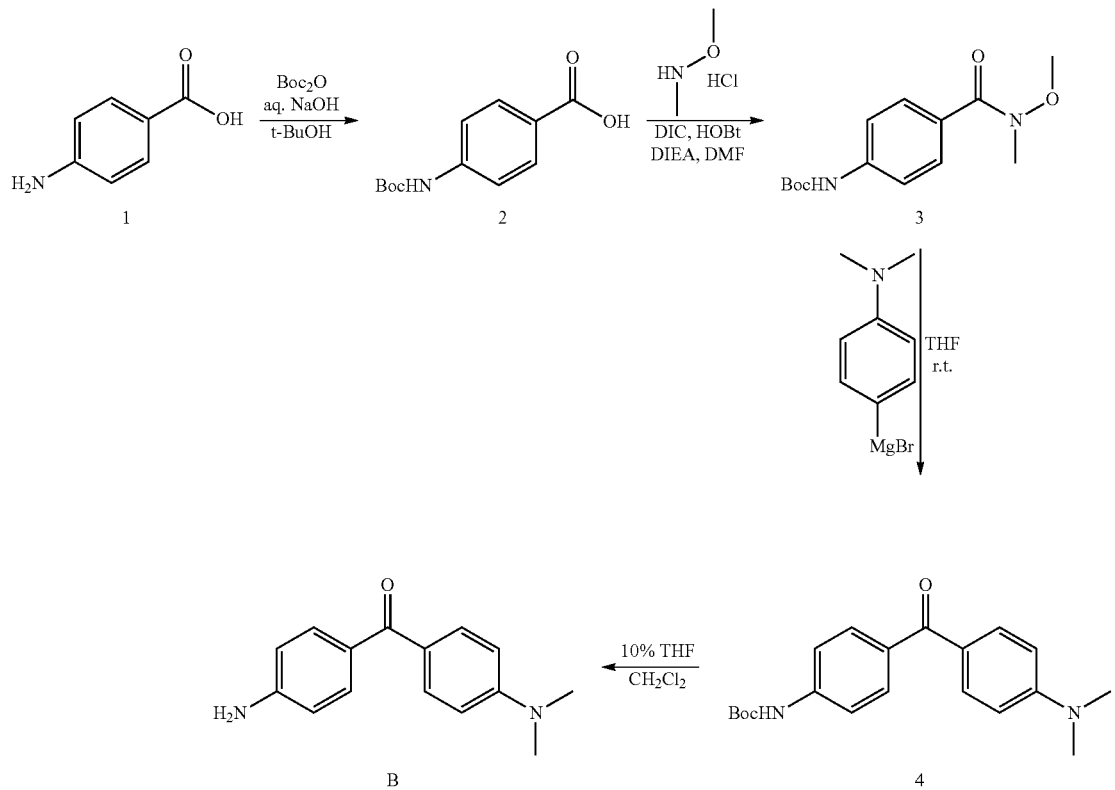

Example 2.1

Synthesis of 4-(tert-butoxycarbonylamino)-benzoic acid (2)

Di-tert-butyl dicarbonate (Boc₂O) (5.73 g, 26.3 mmol) and sodium hydroxide (NaOH) (0.97 g, 24.2 mmol) were added to a solution of 4-aminobenzoic acid (3.0 g, 21.9 mmol) in t-butyl alcohol (t-BuOH) (20 mL) and water (H₂O) (20 mL). The reaction mixture was stirred at room temperature (r.t.), for 12 hours. The reaction mixture was diluted with water and washed with dichloromethane (CH₂Cl₂). The aqueous layer was adjusted to a pH of about 2 with 2N hydrochloric acid (HCl) and extracted with ethyl acetate. The organic layer was dried over sodium sulphate (Na₂SO₄), and the filtrate was concentrated and purified by silica column chromatography (ethyl acetate/hexane=1/1) (4.64 g, 89%). $^1$H-NMR (CD₃OD) 7.79 (d, J=8.7, 2H), 7.48 (d, J=8.7, 2H), 1.49 (s, 9H). ESI-MS m/z calcd for $C_{12}H_{15}NO_4$: 237.2518. found: 235.9861 [M−1].

Example 2.1

Synthesis of tert-butyl 4-[N-methyl-N-methoxyamido]-phenylcarbamate (3)

Hydroxybenzotriazole (HOBt) (2.83 g, 21.1 mmol) and diisopropylcarbodiimide (DIC) (3.0 mL, 19.4 mmol) were added to a solution of 2 (2.0 g, 8.4 mmol) in dimethylformamide (DMF) (15 mL). After stirring for 15 minutes, N,O-dimethylhydroxylamine hydrochloride (1.64 g, 16.8 mmol) dissolved in DMF (10 mL) and diisopropylethylamine (DIPEA) (8.2 mL, 46.4 mmol) were added to the solution, and the mixture was stirred at room temperature for 12 hours. The reaction mixture was diluted with ethyl acetate and washed with 1N hydrochloric acid (HCl), sodium bicarbonate (NaHCO₃), and sodium chloride (NaCl) aqueous solution respectively. The organic layer was dried over Na₂SO₄, and the filtrate was concentrated and purified by silica column chromatography (ethyl acetate/hexane=1/1) (1.5 g, 64%). $^1$H-NMR (CDCl₃) 7.67 (d, J=8.4, 2H), 7.40 (d, J=8.4, 2H), 3.53 (s, 3H), 3.33 (s, 3H), 1.50 (s, 9H) ppm; ESI-MS m/z calcd for $C_{15}H_{20}N_2O_4$: 280.3196. found 281.1251 [M+1].

Example 2.2

Synthesis of tert-butyl 4-[4'-(dimethylamino)benzoyl]-phenylcarbamate (4)

4-(dimethylamino)phenyl) magnesium bromide (16 mL, 8.0 mmol) was added to a solution of 3 (0.56 g, 2.0 mmol) in tetrahydrofuran (THF) (10 mL) at 0° C. and stirred at room temperature for 12 hours. The reaction mixture was diluted with ethyl acetate and washed with $^1$N—HCl, NaHCO₃, and NaCl aqueous solution respectively. The organic layer was dried over Na₂SO₄, and the filtrate was concentrated and purified by silica column chromatography (ethyl acetate/hexane=1/2) (0.55 g, 81%). $^1$HNMR (CDCl₃) 7.77 (d, 9.0, 2H), 7.72 (d, J=8.7, 2H), 7.45 (d, J=8.7, 2H), 6.67 (d, J=9.0, 2H), 3.06 (s, 6H), 1.53 (s, 9H) ppm; ESI-MS m/z calcd for $C_{20}H_{24}N_2O_3$: 340.4162. found 341.2371 [M+1].

Example 2.3

Synthesis of 4-aminophenyl[4'-(dimethylamino)phenyl]-methanone (B)

The compound 4 (51 mg, 0.15 mmol) was stirred in 10% trifluoroacetic acid (TFA) in dichloromethane (10 mL) at room temperature for 1 hour and extracted with ethyl acetate with aqueous NaHCO$_3$. The organic layer was dried over Na$_2$SO$_4$, and the filtrate was concentrated to give intermediate B (34 mg, 95%). $^1$H-NMR (CDCl$_3$) 7.76 (d, J=8.7, 2H), 7.66 (d, J=8.4, 2H), 6.68 (d, J=8.7, 2H), 6.67 (d, J=8.4, 2H), 4.04 (br. s, 1H), 3.06 (s, 6H) ppm; ESI-MS m/z calcd for C$_{15}$H$_{16}$N$_2$O: 240. 3004. found 241.2071 [M+1].

Example 3

Synthesis of Intermediate C

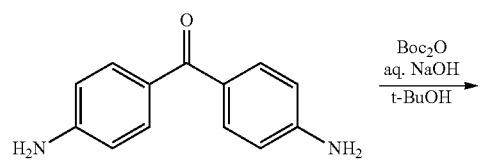

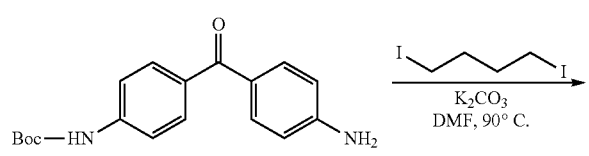

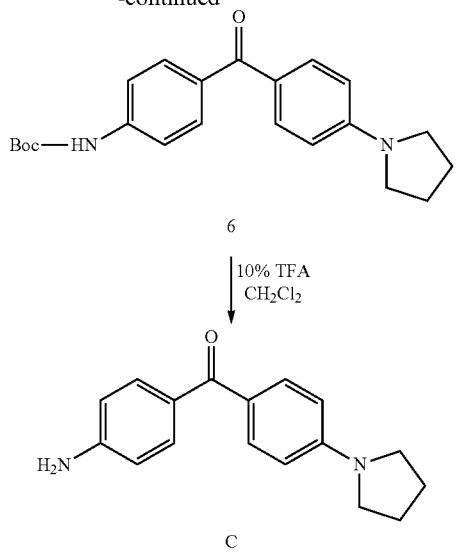

Boc$_2$O (1.2 g, 5.6 mmol) was added to a solution of 4,4'-diaminobenzophenone (1.0 g, 4.7 mmol) in t-BuOH (10 mL) and H$_2$O (10 mL). The reaction mixture was stirred at room temperature for 12 hours. The reaction mixture was diluted with water and washed with CH$_2$Cl$_2$. The aqueous layer was adjusted to a pH of about 2 with 2N HCl and extracted with ethyl acetate. The organic layer was dried over Na$_2$SO$_4$, and the filtrate was reacted with 1,4-diiodobutane and potassium carbonate (K$_2$CO$_3$) in dimethylformamide (DMF) at 90° C. for 12 hours. The reaction mixture was diluted with ethyl acetate and washed with 1N HCl, NaHCO$_3$, and NaCl aqueous solution, respectively. The organic layer was dried over Na$_2$SO$_4$, and the filtrate was concentrated. The compound 6 was subsequently stirred in 10% trifluoroacetic acid (TFA) in dichloromethane (10 mL) at room temperature for 1 hour and extracted with ethyl acetate with aqueous NaHCO$_3$. The organic layer was dried over Na$_2$SO$_4$, and the filtrate was concentrated to give intermediate C (overall 250 mg, 20%). $^1$H-NMR (CDCl$_3$) 7.67 (d, J=8.7, 2H), 7.56 (d, J=8.4, 2H), 6.57 (d, J=8.4, 2H), 6.44 (d, J=8.7, 2H), 3.26 (m, 4H), 1.93 (m, 4H) ppm; $^{13}$C-NMR (CDCl$_3$): 25.54, 47.45, 110.48, 117.20, 131.42, 132.67, 141.23, 142.03, 150.66, 152.22, 160.94 ppm; HRMS (ESI): m/z calcd for C$_{17}$H$_{18}$N$_2$O: 266.3376. found 267.3781 [M+1].

Example 4

Synthesis of Intermediate D

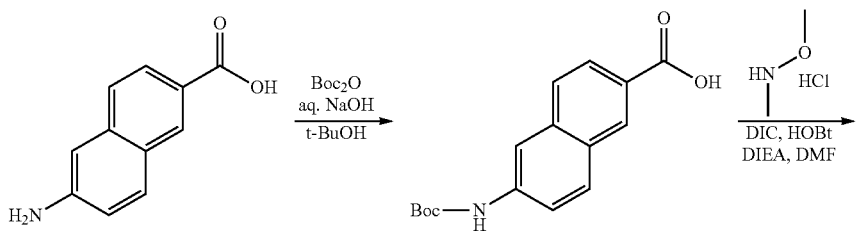

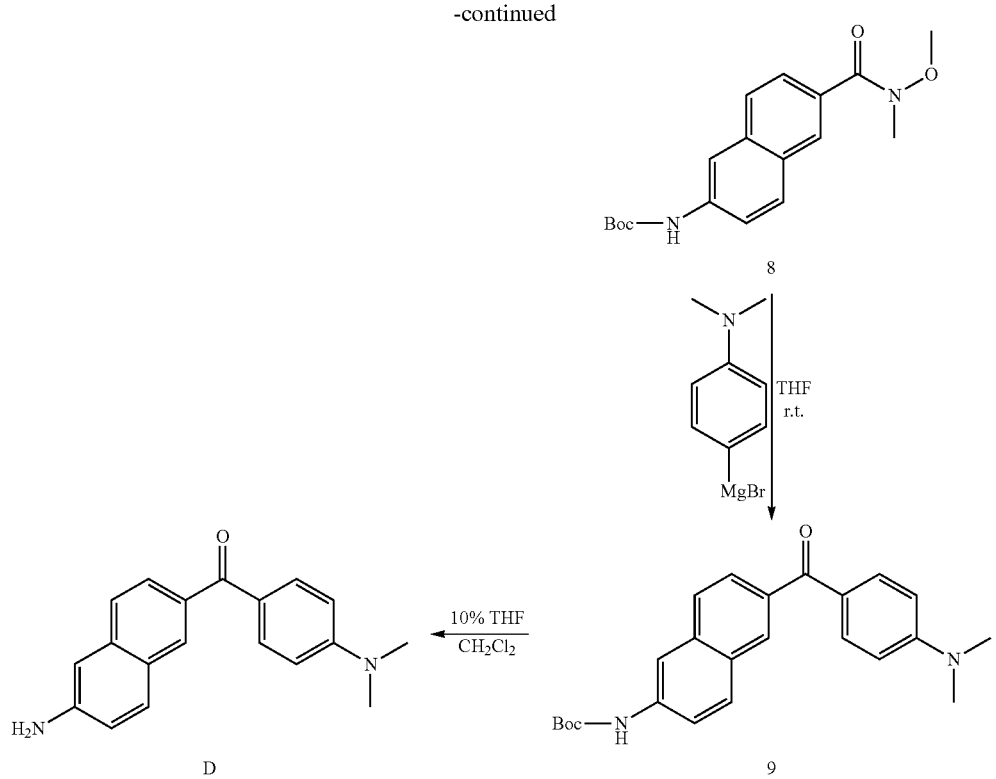

Example 4.1

Synthesis of 6-(tert-butoxycarbonylamino)-2-naphthoic acid (7)

Boc$_2$O (280 mg, 1.28 mmol) and NaOH (40 mg, 1.0 mmol) were added to a solution of 6-amino-2-naphthoic acid (200 mg, 1.07 mmol) in t-BuOH (6 mL) and H$_2$O (6 mL). The reaction mixture was stirred at room temperature for 12 hours, after which it was diluted with water and washed with CH$_2$Cl$_2$. The aqueous layer was adjusted to a pH level of about 2 with 2N HCl and extracted with ethyl acetate. The organic layer was dried over Na$_2$SO$_4$, and the filtrate was concentrated and purified by silica column chromatography (ethyl acetate/hexane=1/1) (300 mg, 98%). $^1$H-NMR (CD$_3$OD) 8.48 (s, 1H), 8.05 (s, 1H), 7.95 (d, J=8.4, 1H), 7.86 (d, J=8.7, 1H), 7.75 (d, J=8.7, 1H), 7.51 (d, J=8.8, 1H) 1.53 (s, 9H) ppm; ESI-MS m/z calcd for C$_{16}$H$_{17}$N$_2$O: 287.3105. found 288.8273 [M+1].

Example 4.2

Synthesis of tert-butyl 6-[N-methyl-N-methoxyamido)-naphthalen-2-ylcarbamate (8)

HOBt (351 mg, 2.6 mmol) and DIC (0.37 mL, 2.4 mmol) were added to a solution of 7 (300 mg, 1.04 mmol) in DMF (5 mL). After stirring for 15 min, N,O-dimethylhydroxylamine hydrochloride (203 mg, 2.09 mmol) dissolved in DMF (5 mL) and DIPEA (1.1 mL, 5.74 mmol) were added to the solution, then the mixture was stirred at room temperature for 12 hours. The reaction mixture was diluted with ethyl acetate and washed with 1N HCl, NaHCO$_3$, and NaCl aqueous solution, respectively. The organic layer was dried over Na$_2$SO$_4$, and the filtrate was concentrated and purified by silica column chromatography (ethyl acetate/hexane=1/1) (300 mg, 87%). $^1$HNMR (CDCl$_3$) 8.14 (s, 1H), 8.05 (s, 1H), 7.76 (m, 2H), 7.37 (d, J=8.4, 1H), 6.87 (s, 1H), 3.56 (s, 3H), 3.40 (s, 3H), 1.55 (s, 9H) ppm; ESI-MS m/z calcd for C$_{18}$H$_{22}$N$_2$O$_4$: 330.3783. found 331.1728 [M+1].

Example 4.3

Synthesis of tert-butyl 6-[4-(dimethylamino)benzoyl]-naphthalen-2-ylcarbamate (9)

(4-(dimethylamino)phenyl) magnesium bromide (6.8 mL, 3.4 mmol) was added to a solution of 8 (280 mg, 0.85 mmol) in THF (8 mL) at 0° C. and stirred for 12 hours. The reaction mixture was diluted with ethyl acetate and washed with 1N—HCl, NaHCO$_3$, and NaCl aqueous solution, respectively. The organic layer was dried over Na$_2$SO$_4$, and the filtrate was concentrated and purified by silica column chromatography (ethyl acetate/hexane=1/2) (70 mg, 21%). $^1$HNMR (CDCl$_3$) 8.14 (s, 1H), 8.07 (s, 1H), 7.83 (m, 3H), 7.39 (d, J=6.0, 1H), 6.83 (s, 1H), 6.70 (d, J=9.0, 2H) 3.08 (s, 6H), 1.56 (s, 9H) ppm; ESI-MS m/z calcd for C$_{24}$H$_{26}$N$_2$O$_3$: 390.4748. found 391.6231 [M+1].

Example 4.4

Synthesis of 6-aminonaphthalen-2-yl-[4-(dimethylamino)phenyl]-methanone (D)

The compound 9 (70 mg, 0.18 mmol) was stirred in 10% TFA in dichloromethane (10 mL) at room temperature for 1 hour and extracted with ethyl acetate with aqueous NaHCO$_3$. The organic layer was dried over Na$_2$SO$_4$, and the filtrate was concentrated to give intermediate D (50 mg, 96%). $^1$H-NMR (CD$_3$OD) 8.02 (s, 1H), 7.59-7.78 (m, 5H), 7.00-7.07 (m, 2H), 6.80 (m, 3H), 3.09 (s, 6H) ppm; ESI-MS m/z calcd for $C_{19}H_{18}N_2O$: 290.3590. found 291.1821 [M+1].

Example 5

Preparation of 2-Chlorotrityl Chloride from 2-Chlorotrityl Alcohol Resin

2-Chlorotrityl alcohol resin (500 mg 1.37 mmol/g) was suspended in dichloromethane (5 mL) for 10 minutes. Thionyl chloride (150 µL, 2.06 mmol) was added and the resin solution was shaken for 2 hours at room temperature. The resin was filtered and washed with dichloromethane and acetonitrile then dried.

Example 6

General Procedure for Loading Intermediates A to D to Solid Resin

Each intermediate compound A to D (0.411 mmol) was dissolved in dichloromethane (5 mL) contained in a 20 mL vial. If the compound was not soluble, DMF was further added (about 1 to 2 mL). The solution was added to 2-chlorotrityl chloride resin (0.274 mmol) suspended in dichloromethane (1 mL), and pyridine (4.1 mmol) was added. After stirring for 4 hours, the resin was filtered through a 3 mL cartridge and washed with DMF (×5), methanol (×10), and dichloromethane (×10), and dried.

Example 7

General Procedure of Grignard Reaction and Cleavage from the Resin

For each reaction, a resin (10 mg) was suspended in freshly distilled tetrahydrofuran (THF) (0.1 mL) in a 4 mL glass vial. Each Grignard reagent (0.5 M in THF) (1.5 mL) was added and capped tightly with tetrafluoroethylene (TFE) lined cap, and heated at 62° C. on standard heat-block for 1 to 2 days. The list of Grignard reagents used is denoted by Compounds 1 to 29 as W building blocks as shown in FIG. 1A. The resin was filtered through a 1 mL cartridge and washed with dichloromethane (×5), DMF (×5), methanol (×5), and dichloromethane (×5). The resin was dried and treated with 1% trifluoroacetic acid (TFA) in dichloromethane (1.5 mL) for 15 minutes. The solution was drained to the 4 mL vial, and dried using Speed Vacuum.

Example 8

Raman Microscopy of TM Compounds

The experiments were carried out using Renishaw InVia Raman (UK) microscope system having an excitation laser at 633 nm. The laser intensity at the sample after passing through the objective lens was about 6.2 mW. System is connected with Leica microscope and laser light was coupled through a 50× objective lens, which was used to excite the sample and also to collect the return Raman signal. The system uses a Peltier cooled CCD detector to collect all the Raman signals.

The WiRE 3.0 software package (provided with the Renishaw system) was employed for instrument control and data acquisition. Stoke shifted Raman spectra were collected in the wave number range of 400 $cm^{-1}$ to 2000 $cm^{-1}$ with a spectral resolution of about 1 $cm^{-1}$. The exposure time of 10 s was chosen for each measurement. Prior to measurement, the instrument was calibrated with the Raman signal from a silicon standard, centered at 520 $cm^{-1}$.

Example 9

Incubation of TM Compounds with Gold Nanoparticles to Form TM Compound-Gold Nanoparticle Nanotag and SERS Measurement Each dye compound was incubated in a 60 nm citrate stabilized gold colloidal solution to form a TM compound-gold nanoparticle nanotag, and subsequently measure SERS spectra under a confocal Raman microscope. 2 µL of the dye solution (10 µM stock solution deionized water) was mixed with 18 µL of gold (Au) colloid ($2.6 \times 10^{10}$ particles/mL, BB International, UK) in a 1:9 ratio (v/v) to get a 1 µM effective concentration of the dye. 20 µl of the dye-Au colloid mixture solution was pipetted out to a clean glass slide and covered with a cover slip and kept under microscope objective lens for Raman measurement. The average intensities were obtained by three individual measurements of each sample.

Figure 2:
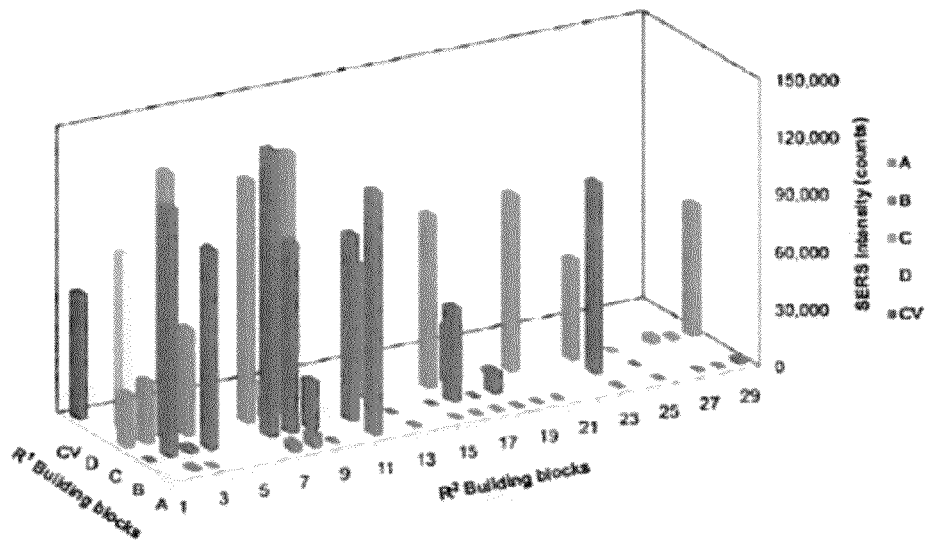
FIG. 2 is a graph comparing SERS intensities of TM compounds from A to D building blocks with crystal violet (CV). SERS spectra were obtained from excitation at 633 nm with laser power of 3 mW. As can be seen from the graph, at least 13 compounds exhibited a stronger SERS signal than CV. In general, compounds with building blocks B and C showed higher SERS intensity than those with building blocks A and D.
Figure 3:
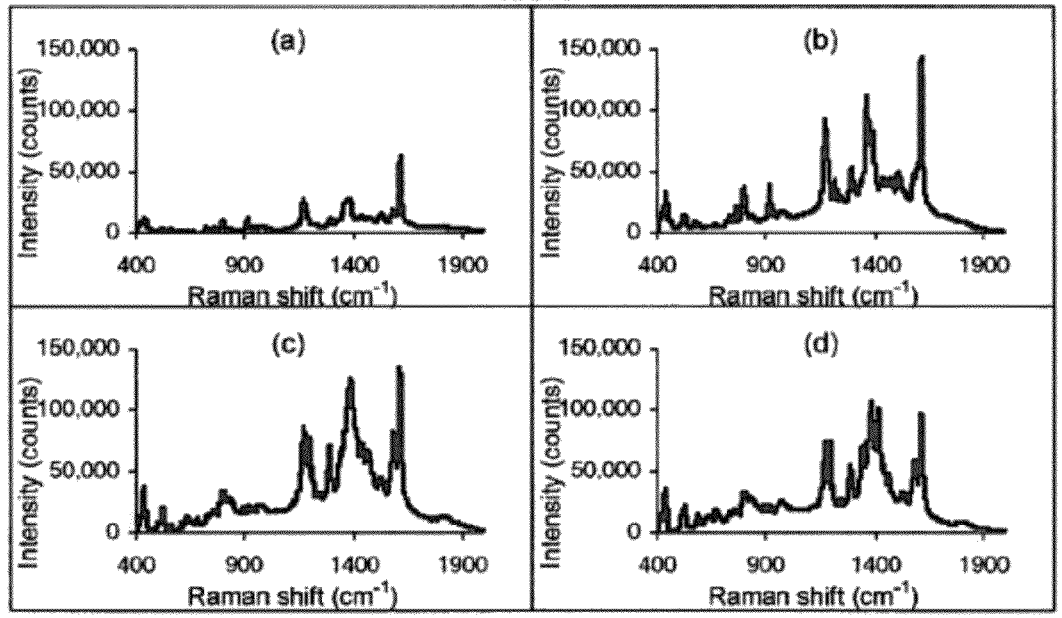
FIG. 3(A) to (D) are graphs showing the SERS spectra of (A) CV and the SERS spectra of PEG encapsulated nanotags of the best three TM compounds: (B) B2; (C) B7; and (D) C7, along with their chemical structures. The highest intensity peak of each SERS spectra was used for comparison and shown in FIG. 4.
Figure 3:
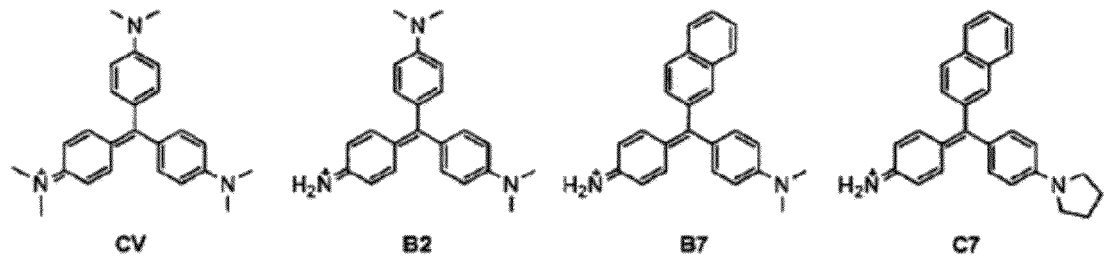

The highest SERS intensity from each spectrum was identified and compared with that of crystal violet (CV) as a reference in FIG. 2. FIG. 2 is a graph comparing SERS intensities of TM compounds from A to D building blocks with CV. SERS spectra were obtained from excitation at 633 nm with laser power of 3 mW. As can be seen from the graph, the SERS signal varies significantly across the different TM compounds, and at least 13 compounds exhibited a stronger SERS signal than CV. In general, compounds with building blocks B and C show higher SERS intensity than those with building blocks A and D.

The best five compounds from the initial screening (B2, B7, C3, C7, and C9) were resynthesized, and the SERS study was carried out in various conditions. In many cases, it was observed that the SERS signal was fluctuating over the measurement and storage time, perhaps due to the aggregation of Au nanoparticles.

Example 10

Modification of TM Compound-Gold Nanoparticle Nanotags with Thiolated PEG

To stabilize the SERS signal, the nanotags were modified by encapsulating the gold surface with thiolated PEG which protected the nanotags from aggregation in aqueous media. Freshly prepared TM compounds, herein also referred as reporter solutions, at concentrations of 5, 10, 20, 30 µM were each rapidly mixed with gold colloid at a volumetric ratio of 1:9 (reporter/colloid). It was found that the molar ratio of TM compounds, herein referred also as reporter molecules, at a dye concentration of 10 µM was optimized with maximum SERS intensities and minimum colloidal aggregation. After incubating for 5 minutes, thiolated PEG (PEG-SH, Molecular Weight of PEG ($M.W_{PEG}$): 5000 dalton, RAPP Polymere GmbH) solution (100 µM) was added around 10 to 20 fold excess in order to get maximum surface coverage. After incubating overnight, the excess PEG-SH was removed by three round of centrifugation (8000 rpm for 3 minutes) and re-suspended with water.

It was observed that PEG encapsulated nanotags did not show significant aggregation under ambient conditions and furnished stable SERS intensity for all five compounds. FIG. 3(A) to (D) are graphs showing the SERS spectra of PEG encapsulated nanotags and corresponding structure of the best three TM compounds: (A) CV; (B) B2; (C) B7; and (D) C7. The highest intensity peak has been chosen for comparison, and shown in FIG. 4.

Figure 4:
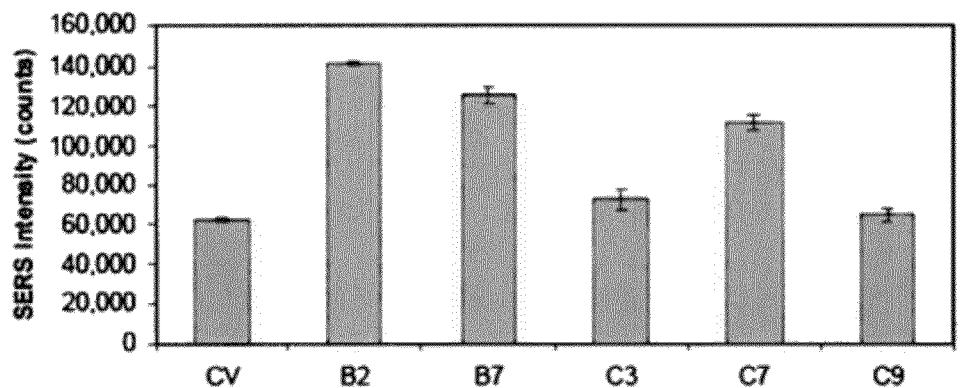
FIG. 4 is a graph comparing the SERS intensities obtained from the highest intensity peak of the respective spectra of PEG encapsulated nanotags of the best five TM compounds B2, B7, C3, C7 and C9, compared with that obtained for CV. The average intensities of five individual measurements are shown in the graph, with error bars denoting their standard deviation. The SERS spectra were obtained from excitation at 633 nm with laser power of 3 mW. As can be seen from the graph, the SERS intensities of the PEG encapsulated nanotags of the TM compounds according to various embodiments of the invention are higher than that for CV.

FIG. 4 is a graph comparing the SERS intensities of PEG encapsulated nanotags. The average intensities of five individual measurements are shown, with error bars denoting their standard deviation. The SERS spectra were obtained from excitation at 633 nm with laser power of 3 mW. Using the graph, the SERS intensities of the PEG encapsulated nanotags could be optimized by changing the dye concentration to that which gave the most stable enhanced signals. As can be seen from FIG. 4, novel reporters B2, B7, and C7 showed 2.3, 2.0, and 1.8 fold increased signal respectively, compared with CV under optimum conditions (10 mM of each dye).

By modifying the hit compounds with surface stabilization, three highly Raman active compounds (B2, B7, and C7) have been identified with high potential as SERS reporters for biological applications.

Example 11

SERS Intensity, Absorbance, Purity, and Mass Data Table for the Nanotags

TABLE 1

| Compound | (i) SERS Intensity (counts) | (ii) Abs (nm) | (iii) Purity | (iv) Mass (calc) | (v) Mass (found) |
|---|---|---|---|---|---|
| A-2 | 1,764 | 572 | 90% | 316.2 | 316.2 |
| A-3 | 0 | 550 | 97% | 303.2 | 303.2 |
| A-7 | 3,894 | 580 | 97% | 323.2 | 323.3 |
| A-8 | 6,549 | 562 | 93% | 319.1 | 319.3 |
| A-9 | 0 | 570 | 83% | 349.2 | 349.4 |
| A-11 | 126,863 | 578 | 96% | 373.2 | 373.3 |
| A-13 | 0 | 566 | 95% | 353.2 | 353.1 |
| A-15 | 0 | 572 | 95% | 273.1 | 273.2 |
| A-16 | 0 | 570 | 97% | 301.2 | 301.2 |
| A-17 | 0 | 586 | 94% | 303.2 | 303.2 |
| A-18 | 0 | 562 | 92% | 317.1 | 317.1 |
| A-19 | 0 | 576 | 86% | 291.1 | 291.2 |
| A-20 | 0 | 570 | 88% | 307.1 | 307.1 |
| A-23 | 0 | 562 | 95% | 287.1 | 287.2 |
| A-25 | 0 | 560 | 97% | 331.2 | 331.2 |
| A-27 | 0 | 574 | 92% | 305.1 | 305.1 |
| A-28 | 0 | 574 | 90% | 279.1 | 279.1 |
| A-29 | 1,878 | 566 | 96% | 315.2 | 315.2 |
| B-1 | 0 | 596 | 93% | 319.2 | 319.4 |
| B-2 | 129,997 | 586 | 92% | 344.2 | 344.4 |
| B-3 | 2,626 | 586 | 98% | 331.2 | 331.3 |
| B-4 | 104,281 | 586 | 83% | 393.2 | 393.4 |
| B-7 | 157,517 | 600 | 95% | 351.2 | 351.4 |
| B-8 | 99,667 | 600 | 96% | 347.2 | 347.3 |
| B-9 | 25,196 | 600 | 91% | 377.2 | 377.3 |
| B-11 | 97,303 | 602 | 99% | 401.2 | 401.4 |
| B-13 | 0 | 600 | 96% | 381.2 | 381.1 |
| B-15 | 0 | 596 | 93% | 301.2 | 301.2 |
| B-16 | 48,933 | 588 | 94% | 329.2 | 329.2 |
| B-17 | 0 | 600 | 93% | 331.2 | 331.2 |
| B-18 | 11,169 | 586 | 91% | 345.2 | 345.2 |
| B-23 | 99,523 | 586 | 96% | 315.2 | 315.2 |
| B-25 | 0 | 588 | 93% | 359.2 | 359.2 |
| C-1 | 27,572 | 596 | 91% | 345.2 | 345.2 |
| C-2 | 32,254 | 596 | 91% | 370.2 | 370.2 |
| C-3 | 139,373 | 584 | 90% | 357.2 | 357.2 |
| C-4 | 55,437 | 598 | 94% | 419.2 | 419.2 |
| C-7 | 126,862 | 598 | 90% | 377.2 | 377.2 |
| C-8 | 8,805 | 602 | 94% | 373.2 | 373.2 |
| C-9 | 137,243 | 600 | 91% | 403.2 | 403.2 |
| C-13 | 69,210 | 596 | 95% | 407.2 | 407.2 |
| C-16 | 89,703 | 596 | 93% | 355.2 | 355.2 |
| C-17 | 29,557 | 602 | 94% | 357.2 | 357.2 |
| C-19 | 3,048 | 602 | 88% | 345.2 | 345.2 |
| C-20 | 92,382 | 602 | 87% | 361.2 | 361.1 |
| C-23 | 52,236 | 586 | 86% | 341.2 | 341.2 |
| C-25 | 0 | 596 | 95% | 385.2 | 385.2 |
| C-27 | 3,676 | 596 | 91% | 359.2 | 359.2 |
| C-28 | 1,529 | 602 | 95% | 333.1 | 333.2 |
| C-29 | 68,516 | 596 | 97% | 369.2 | 369.2 |
| D-2 | 92,117 | 614 | 100% | 394.2 | 394.2 |
| D-9 | 9,113 | 608 | 97% | 427.2 | 427.2 |
| CV | 65,977 | 590 | | | |

Table 1 is a summary table summarizing the (i) SERS intensity; (ii) absorption values; (iii) purity; (iv) calculated mass; and (v) measured mass.

The SERS spectra for (i) were obtained from excitation at 633 nm with laser power of 6.2 mW. The absorption data for (ii) was obtained by SpectraMax Plus384 absorbance plate reader in 50 µM. Purity data for (iii) was calculated on the basis of the integration in the LCMS trace at 550 nm. Mass was calculated as (M+) for (iv), and measured in ESI-MS m/e for (v).

Example 12 $^1$H-NMR, $^{13}$C-NMR, HRMS (ESI), and UV-Vis Data of Re-Synthesized TM Compounds As discussed in Example 9, the best five compounds from the initial screening (B2, B7, C3, C7, and C9) were resynthesized for further studies. $^1$H-NMR, $^{13}$C-NMR, HRMS (ESI), and UV-Vis data of re-synthesized TM compounds are provided as follows.

Figure 5:
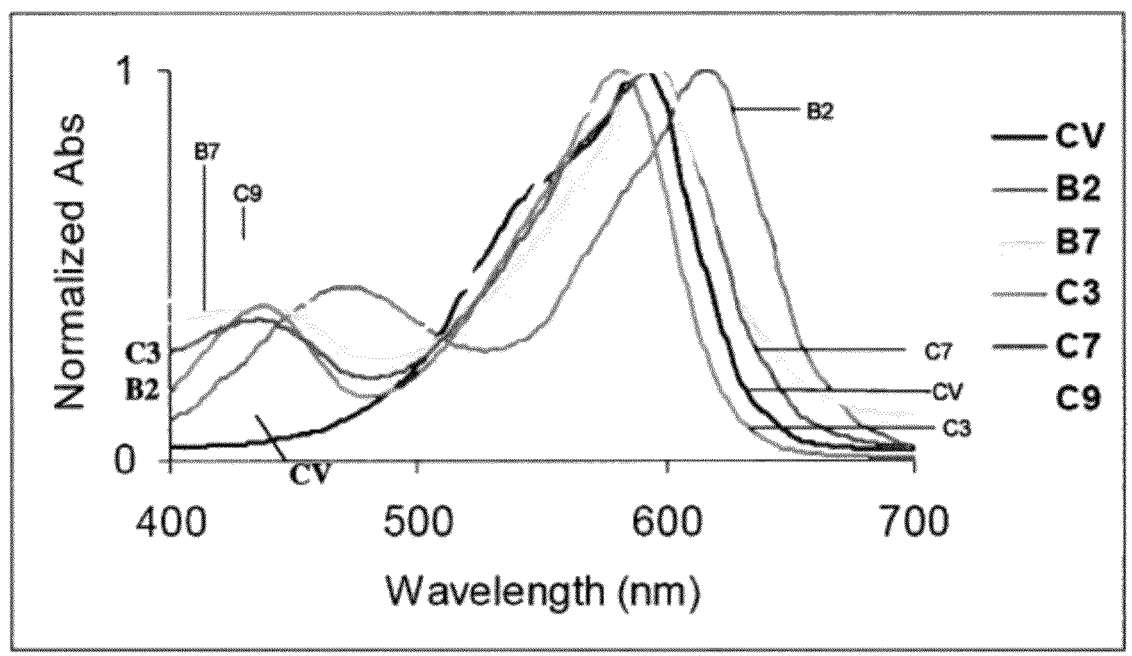
FIG. 5 is a graph showing the ultraviolet-visible (UV-Vis) spectra of the synthesized compounds B2, B7, C3, C7, and C9, and CV.
Figure 6:
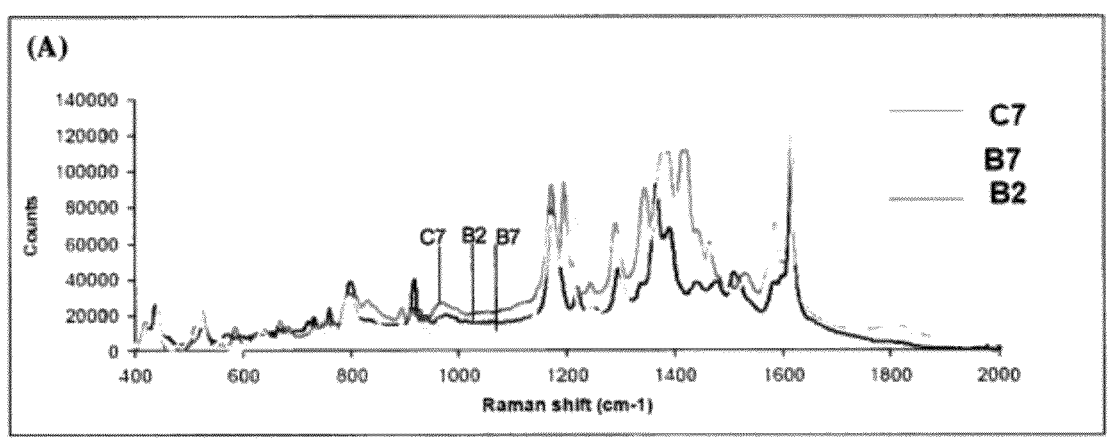
FIG. 6 is (A) a graph showing the SERS spectra of B2, B7, and C7, and (B) a table showing unique identifiable peaks attributable to each of the three curves ($cm^{-1}$).
Figure 7:
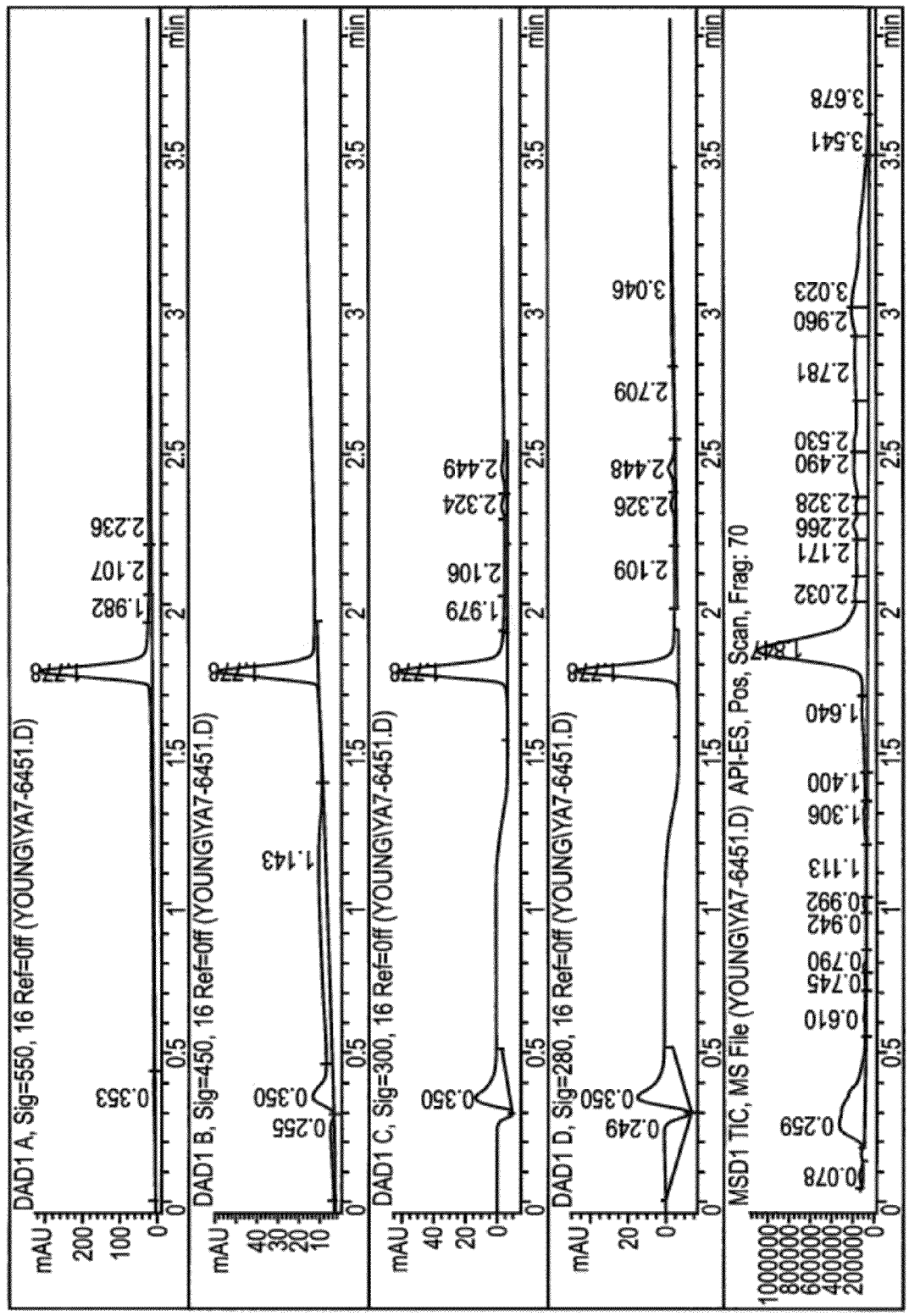
FIG. 7 are liquid chromatography mass spectrometry (LCMS) data of some of the synthesized triphenylmethine compounds and intermediate according to various embodiments of the invention: (A)(i) and (ii) A-2; (B)(i) and (ii) A-13; (C)(i), (ii) and (iii) B-2; (D)(i) B-4; (E)(i), (ii) and (iii) B-7; (F)(i) and (ii) B-16; (G)(i) and (ii) B-25; (H)(i), (ii) and (iii) C-3; (I)(i), (ii) and (iii) C-7; (J)(i) and (ii) C-16; (K)(i) and (ii) C-28; (L) C9, and (M) intermediate C.
Figure 7:
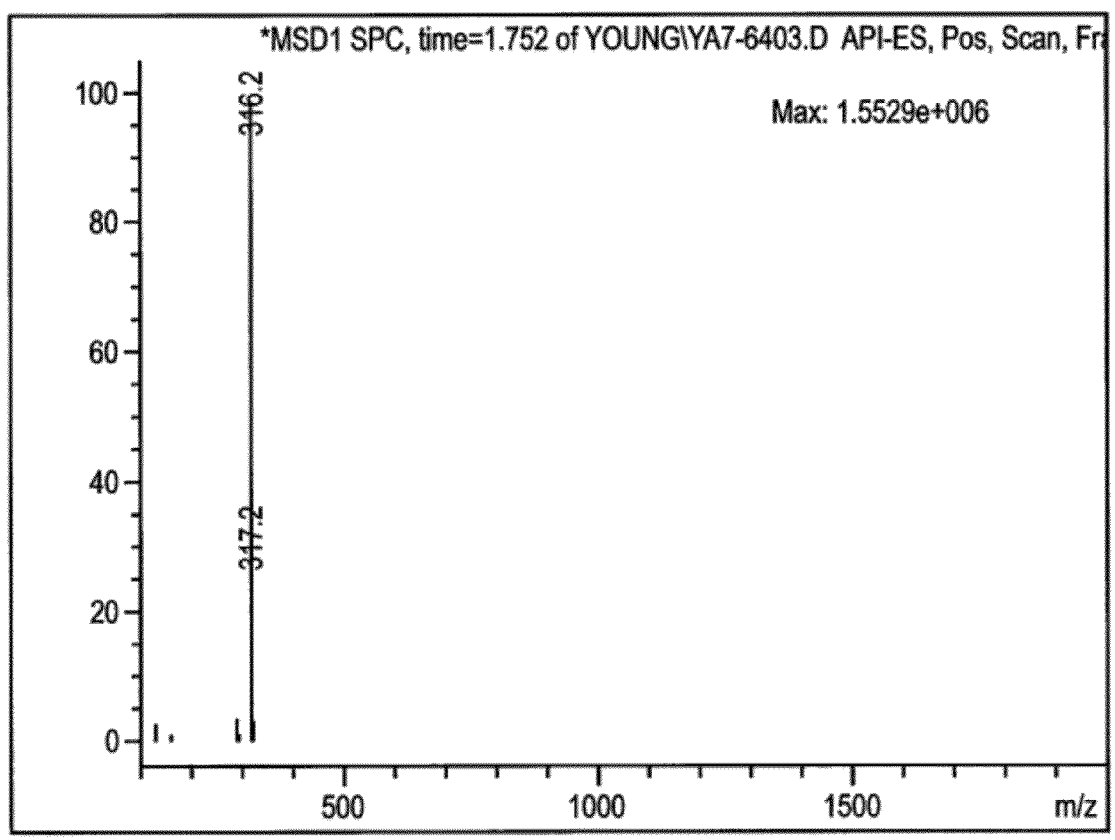
Figure 7:
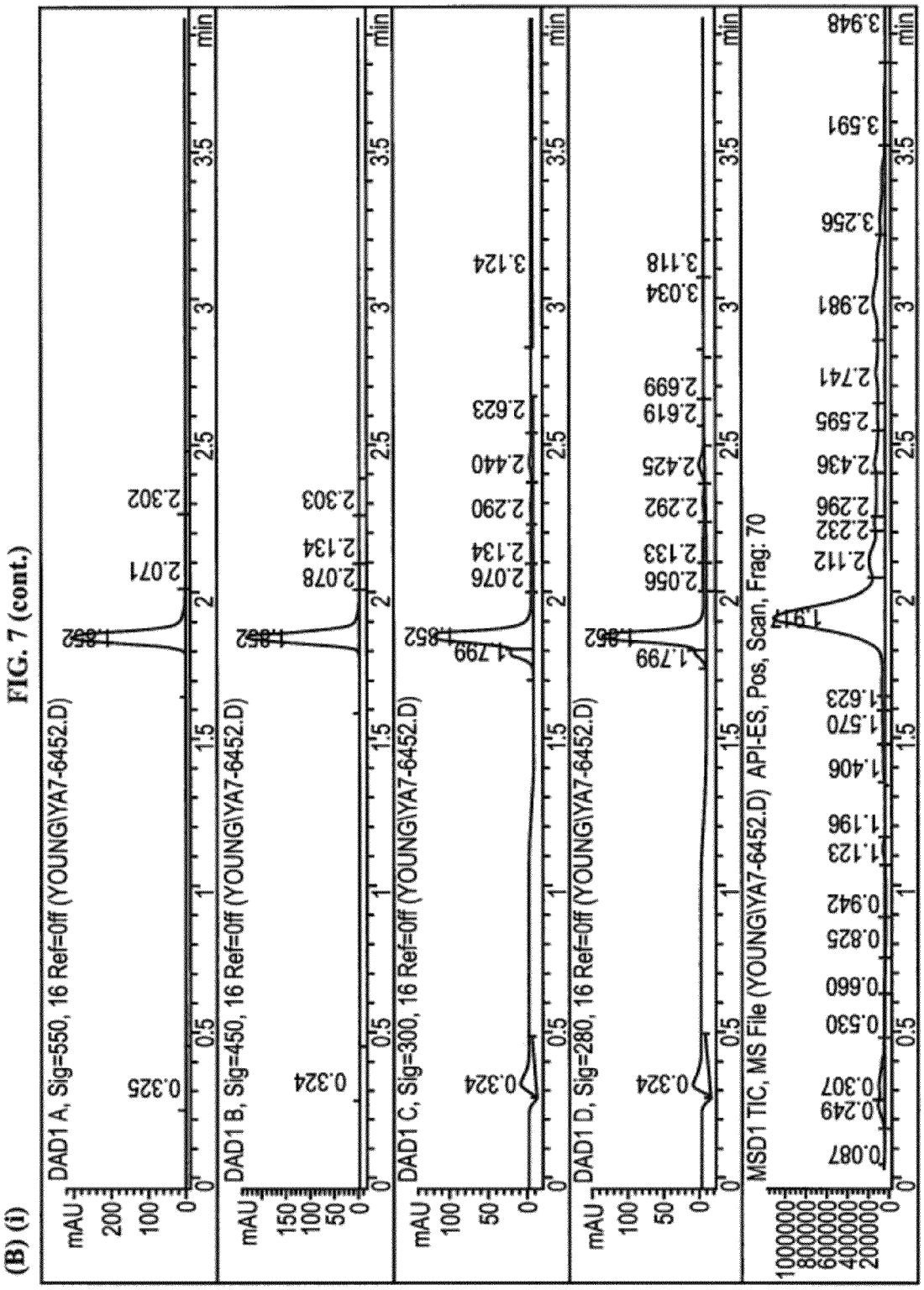
Figure 7:
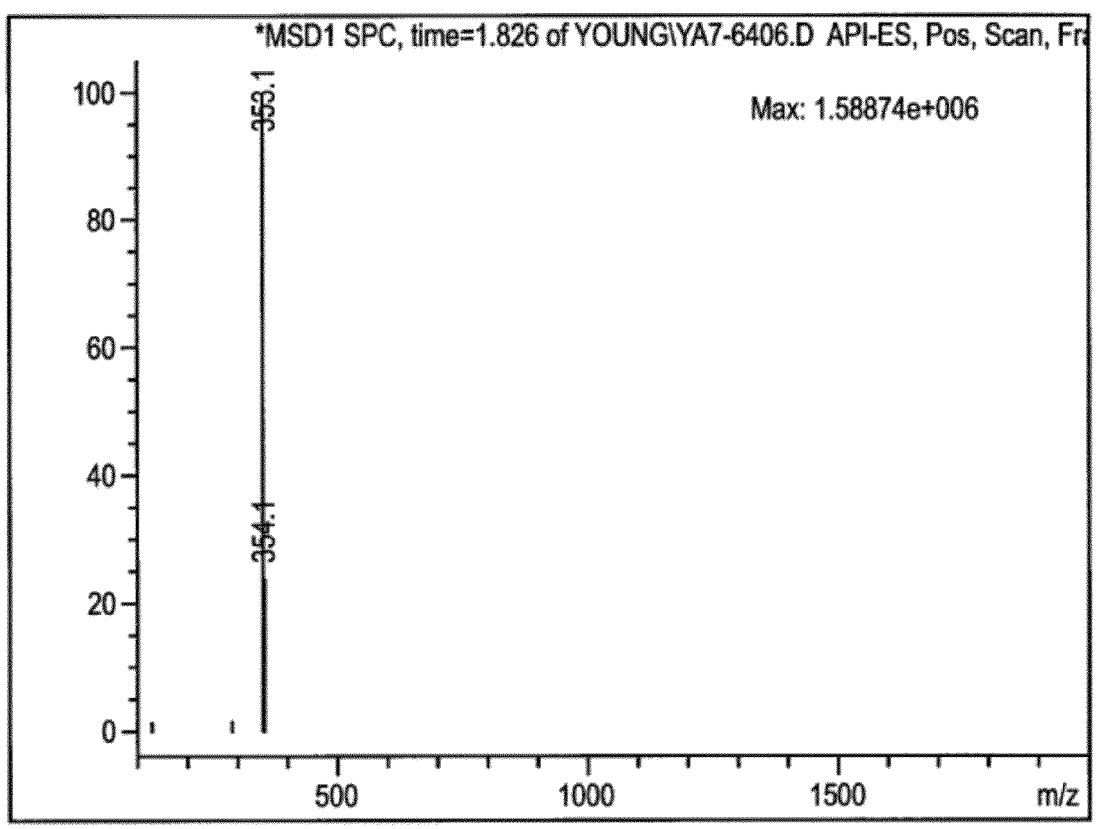
Figure 7:
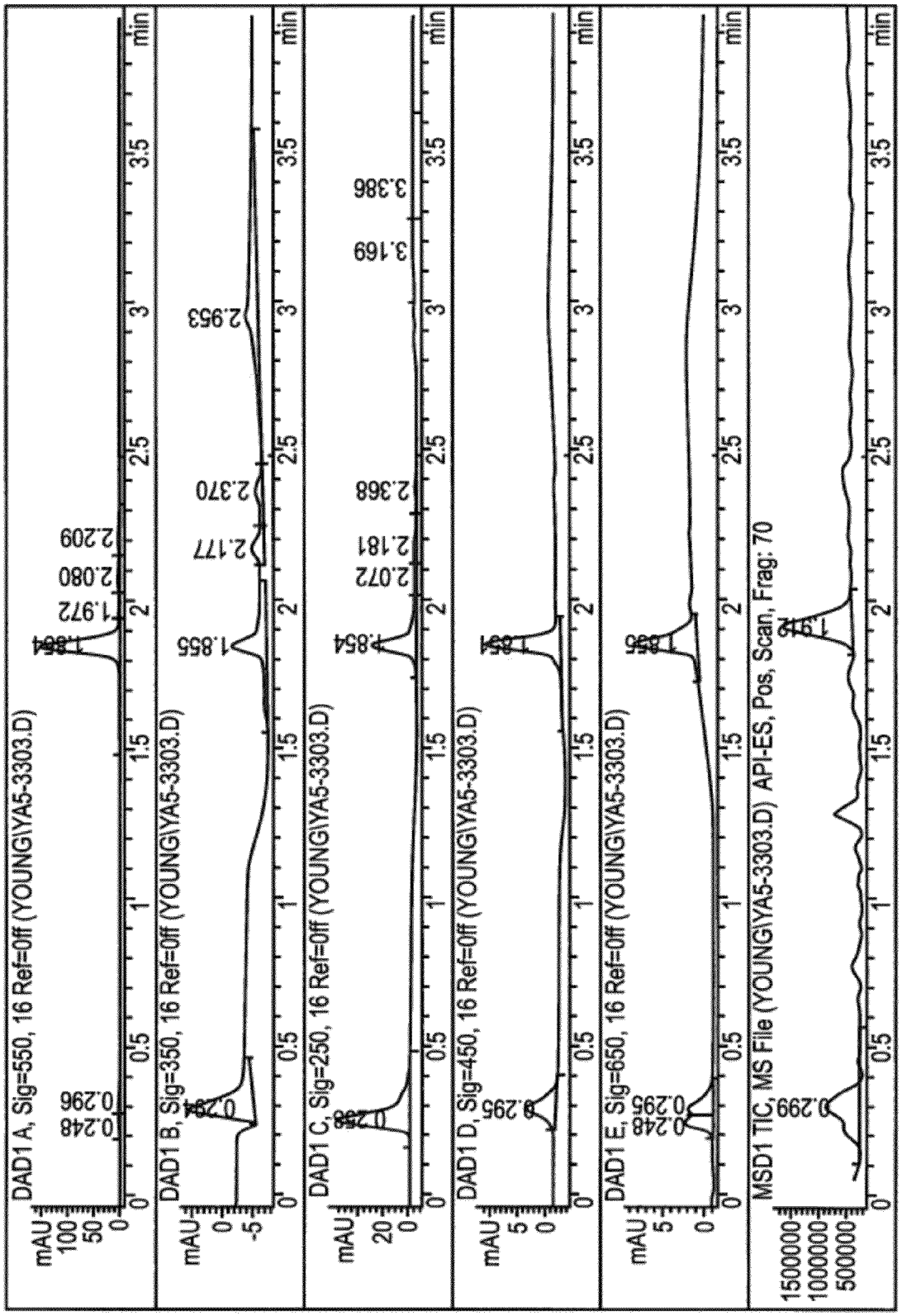
Figure 7:
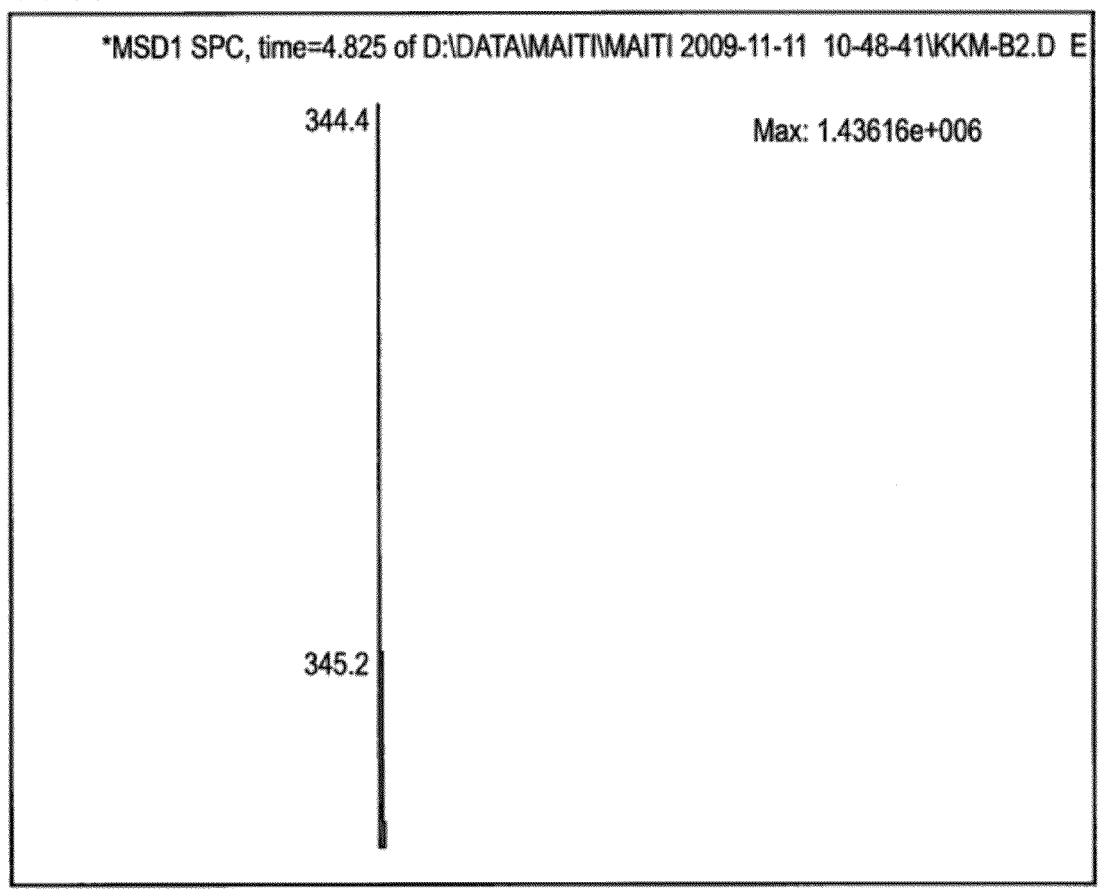
Figure 7:
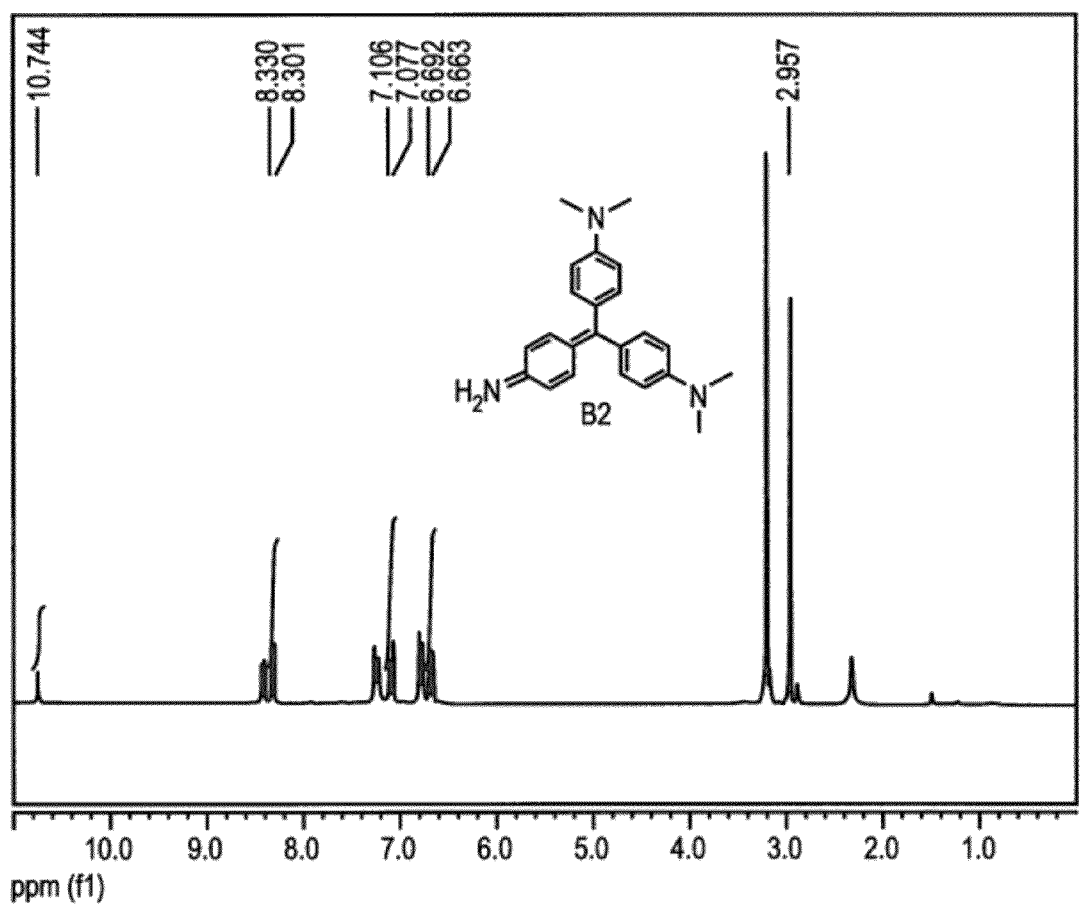
Figure 7:
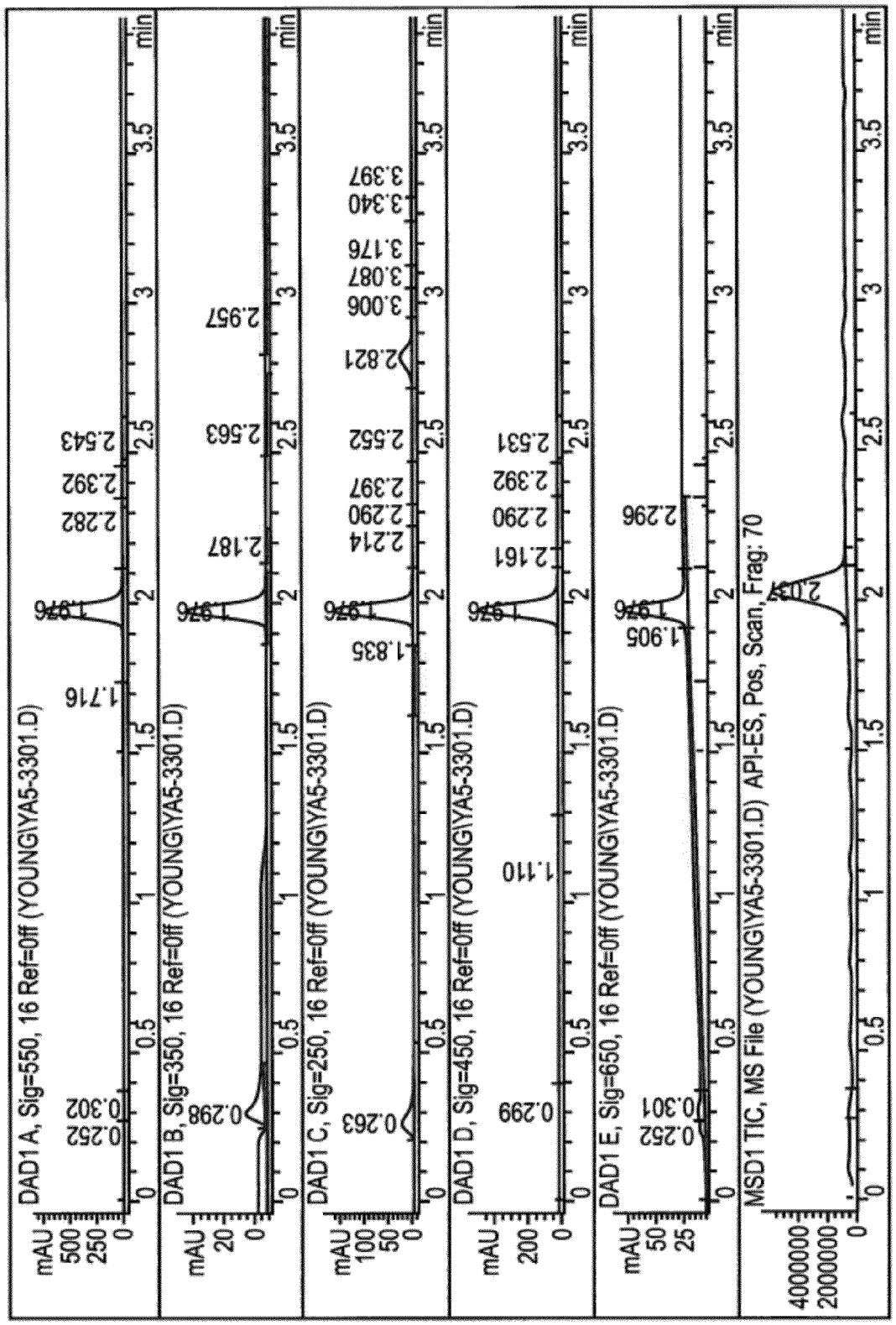
Figure 7:
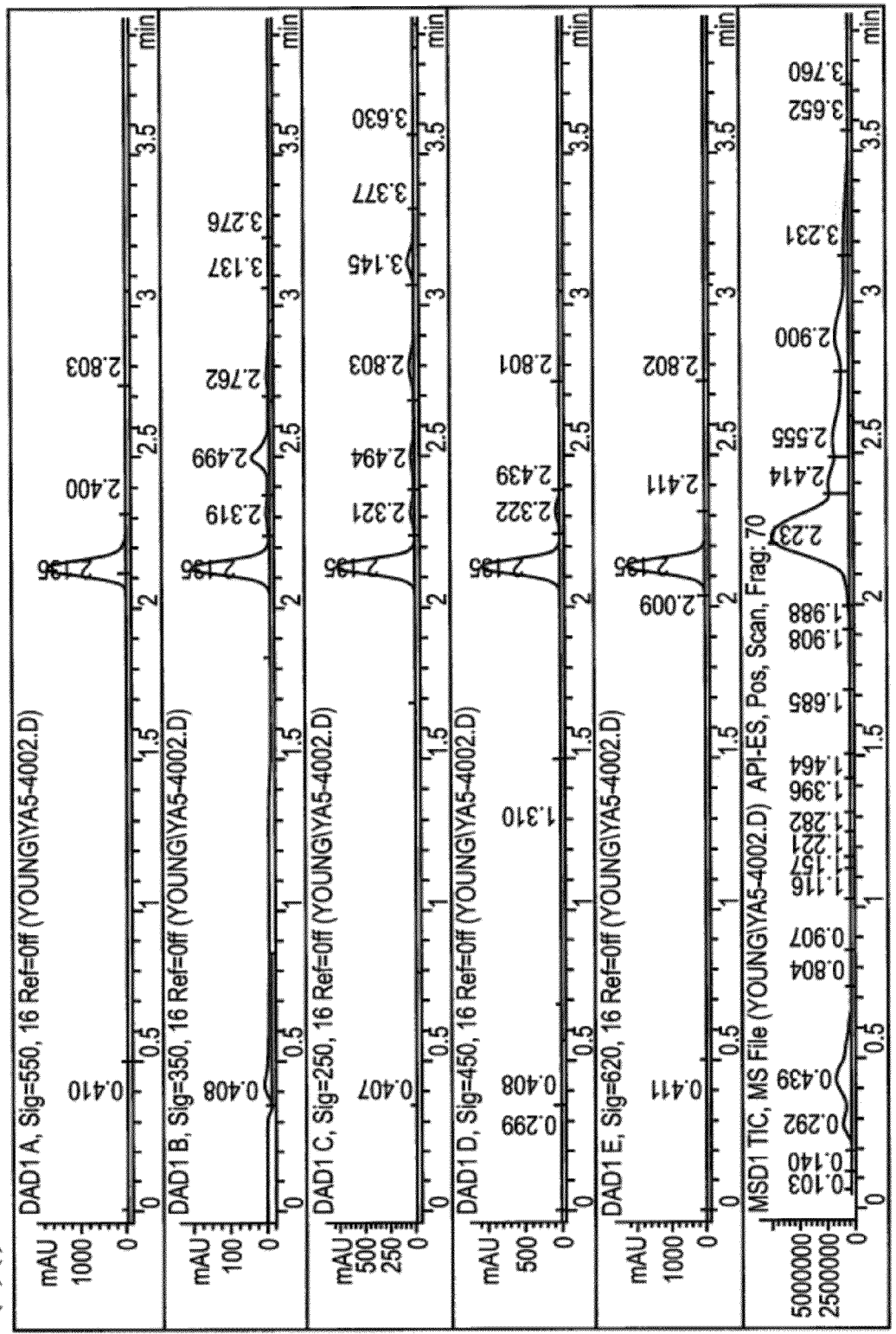
Figure 7:
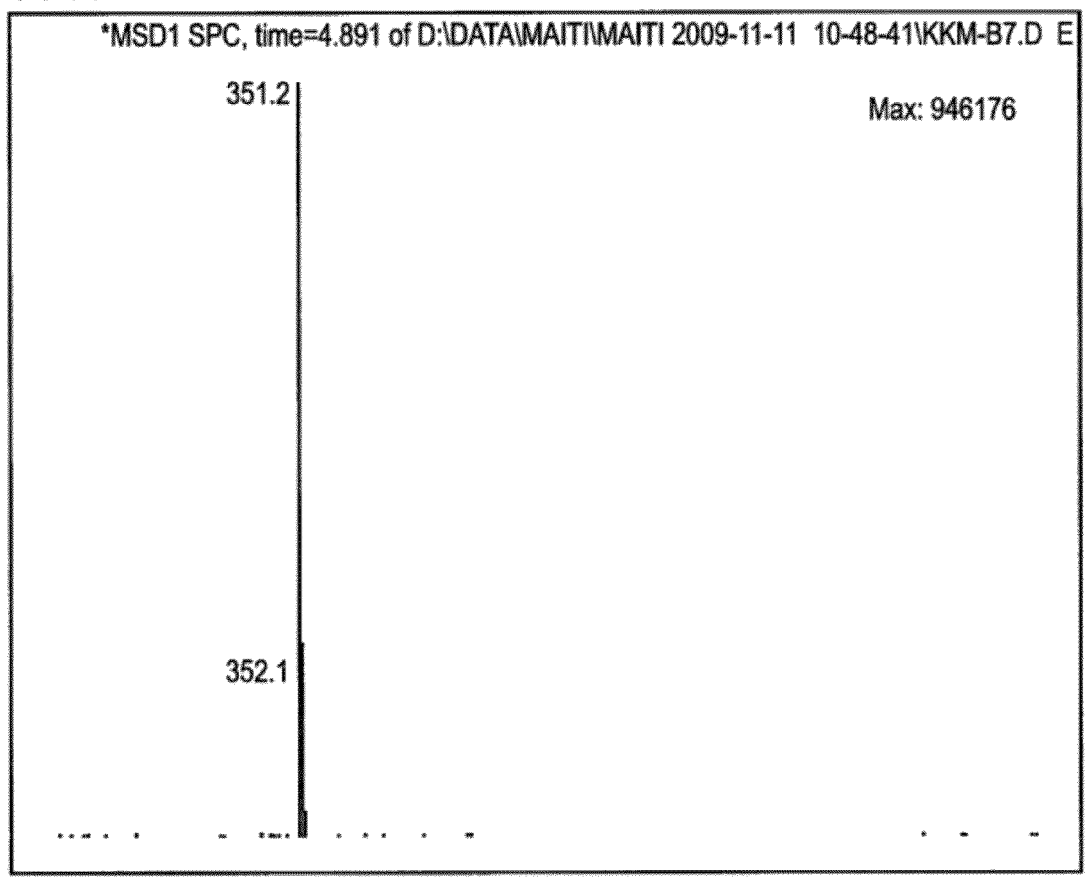
Figure 7:
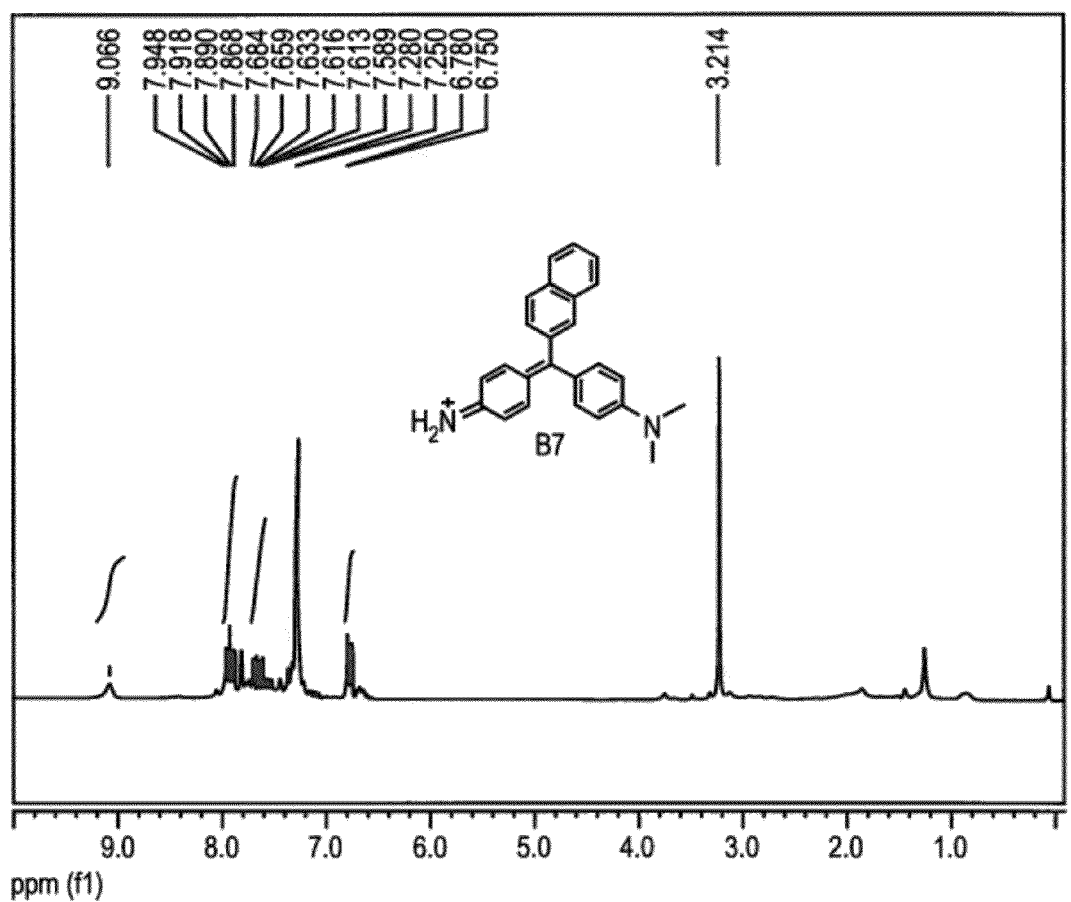
Figure 7:
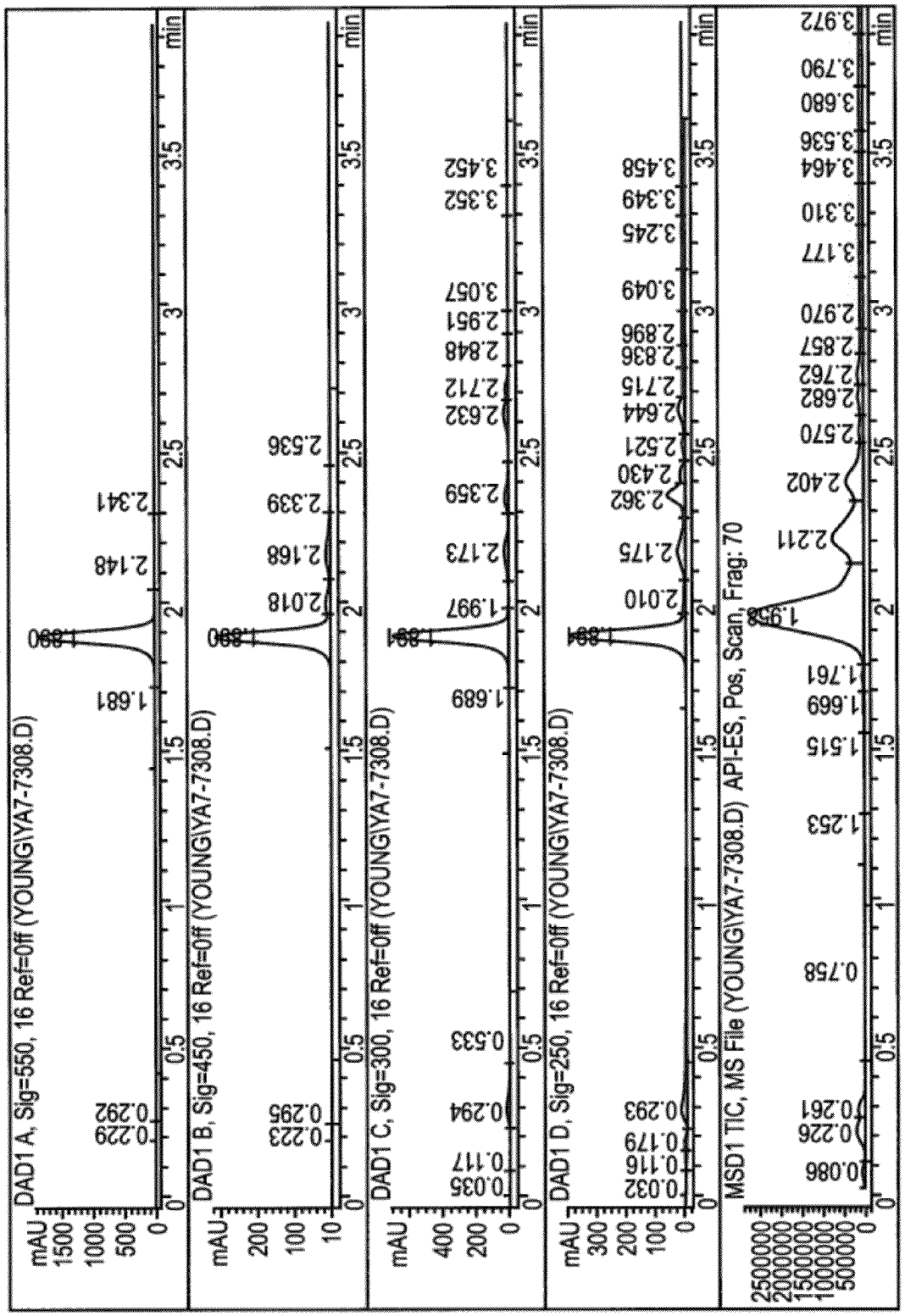
Figure 7:
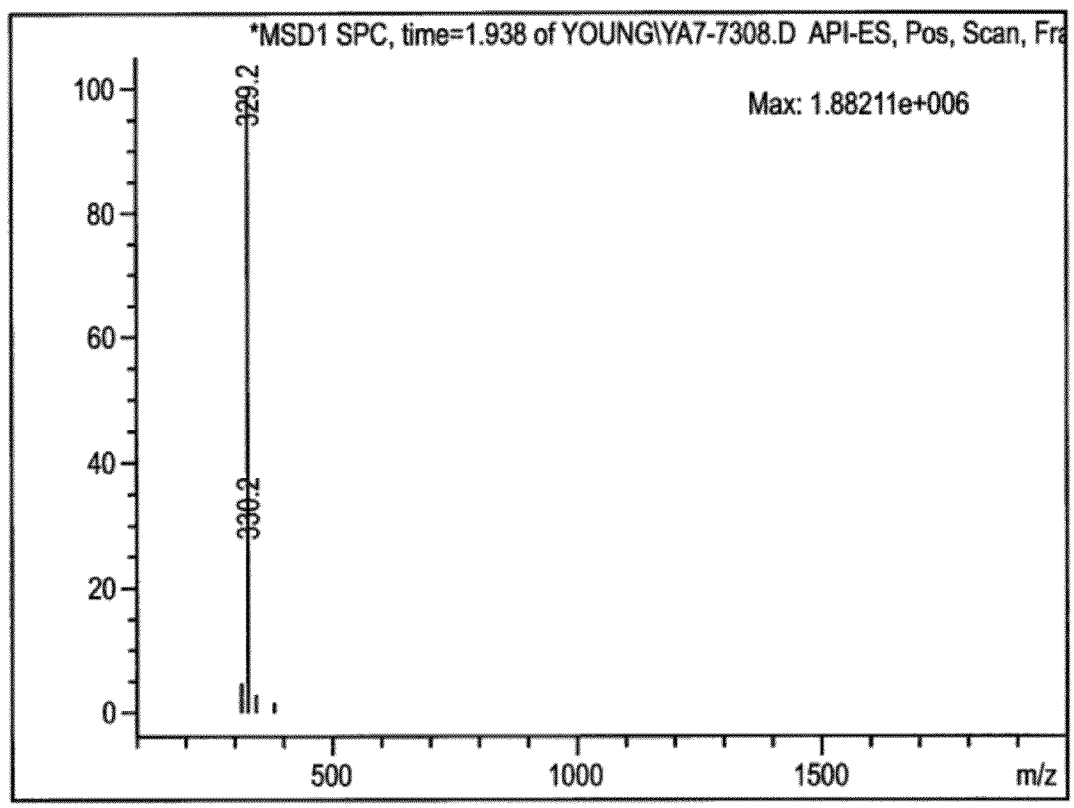
Figure 7:
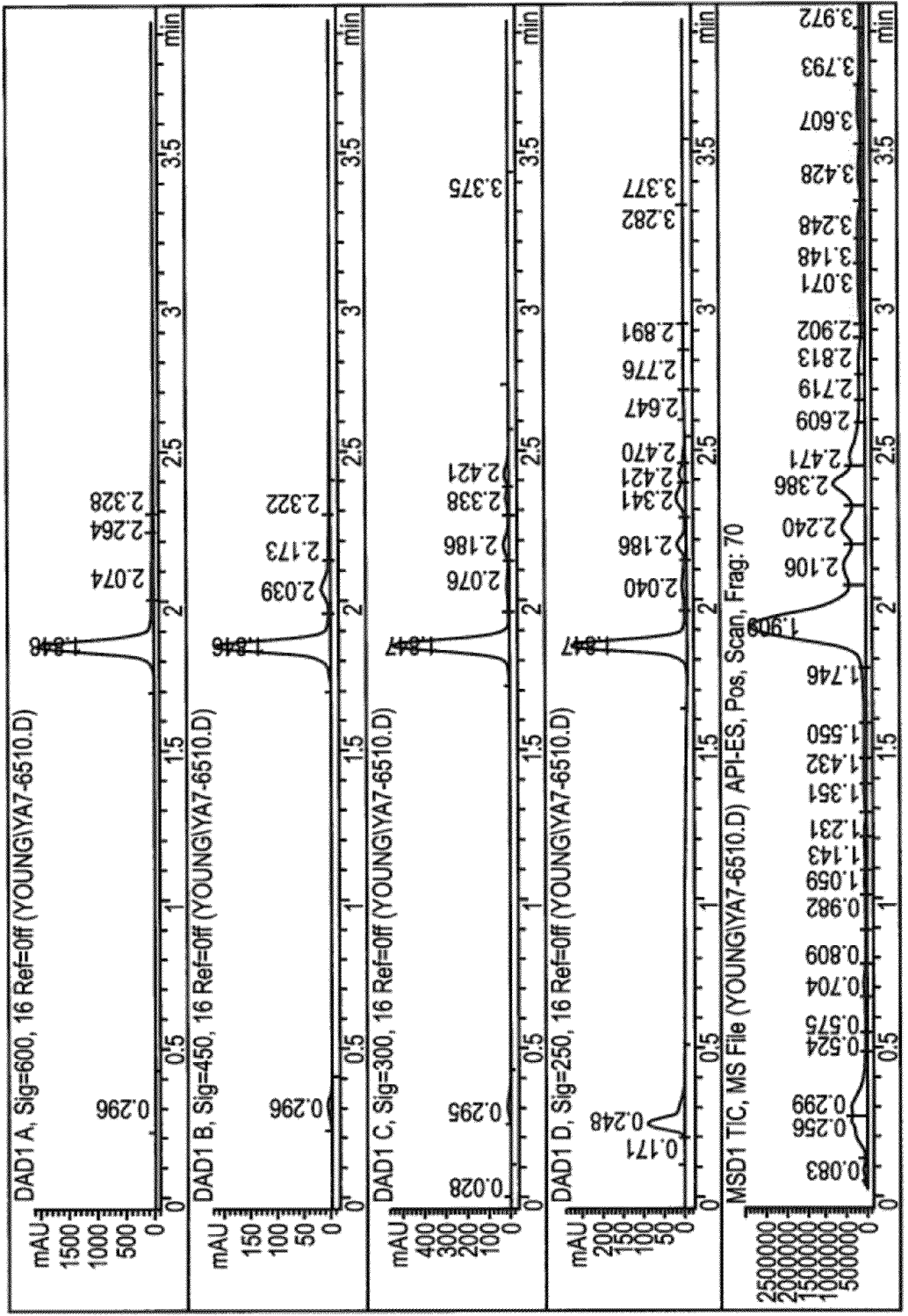
Figure 7:
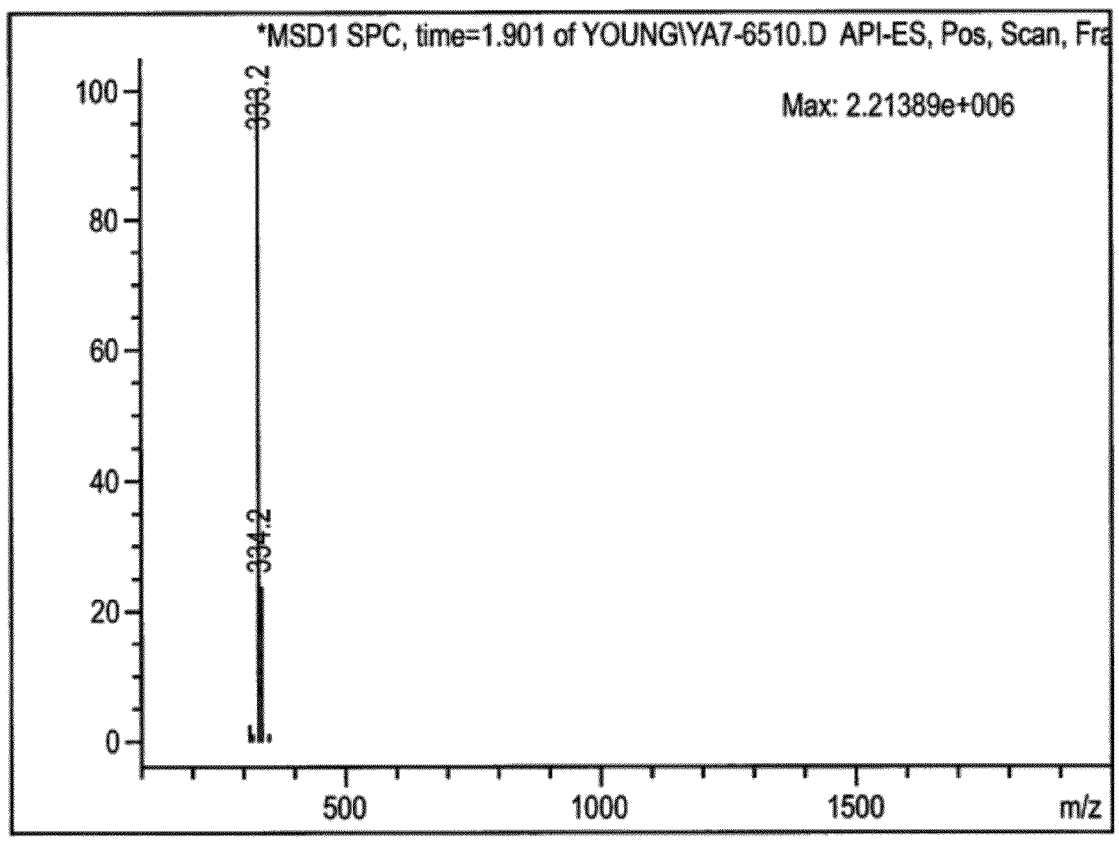
Figure 7:
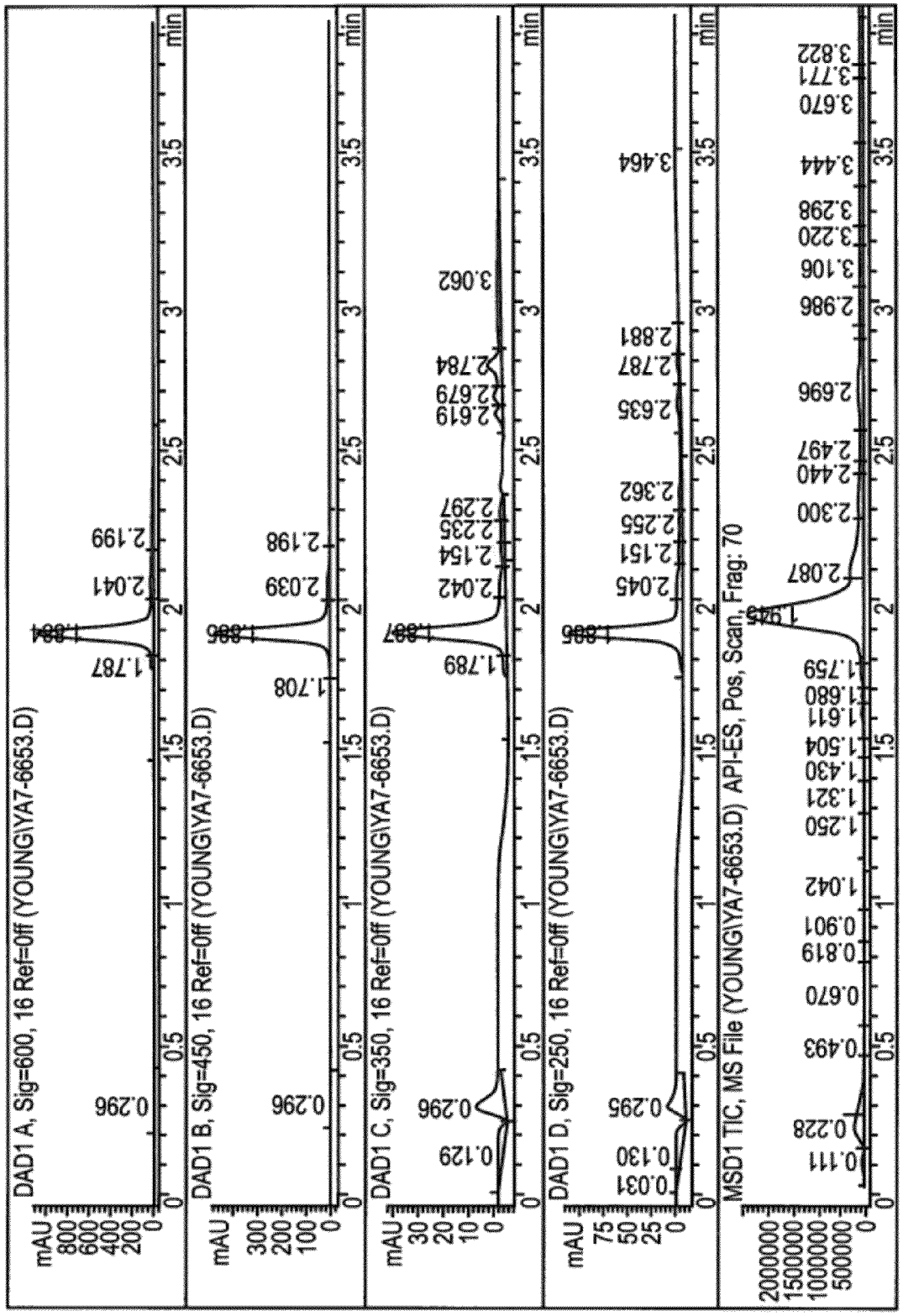
Figure 7:
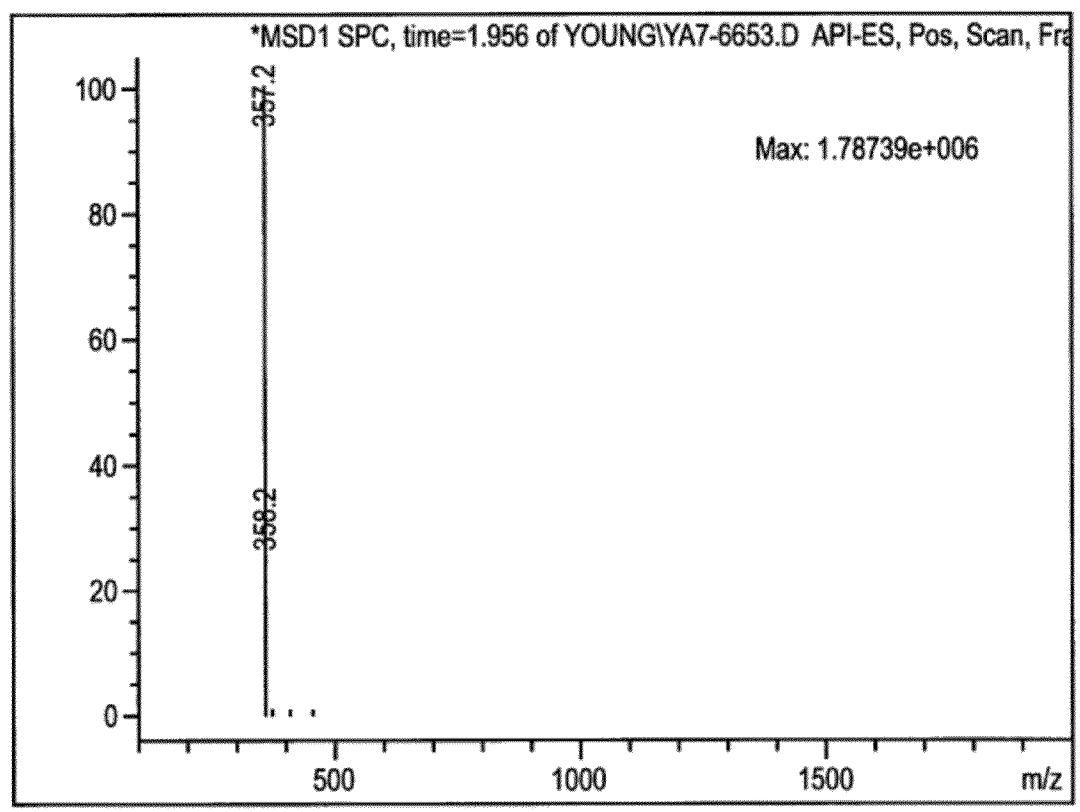
Figure 7:
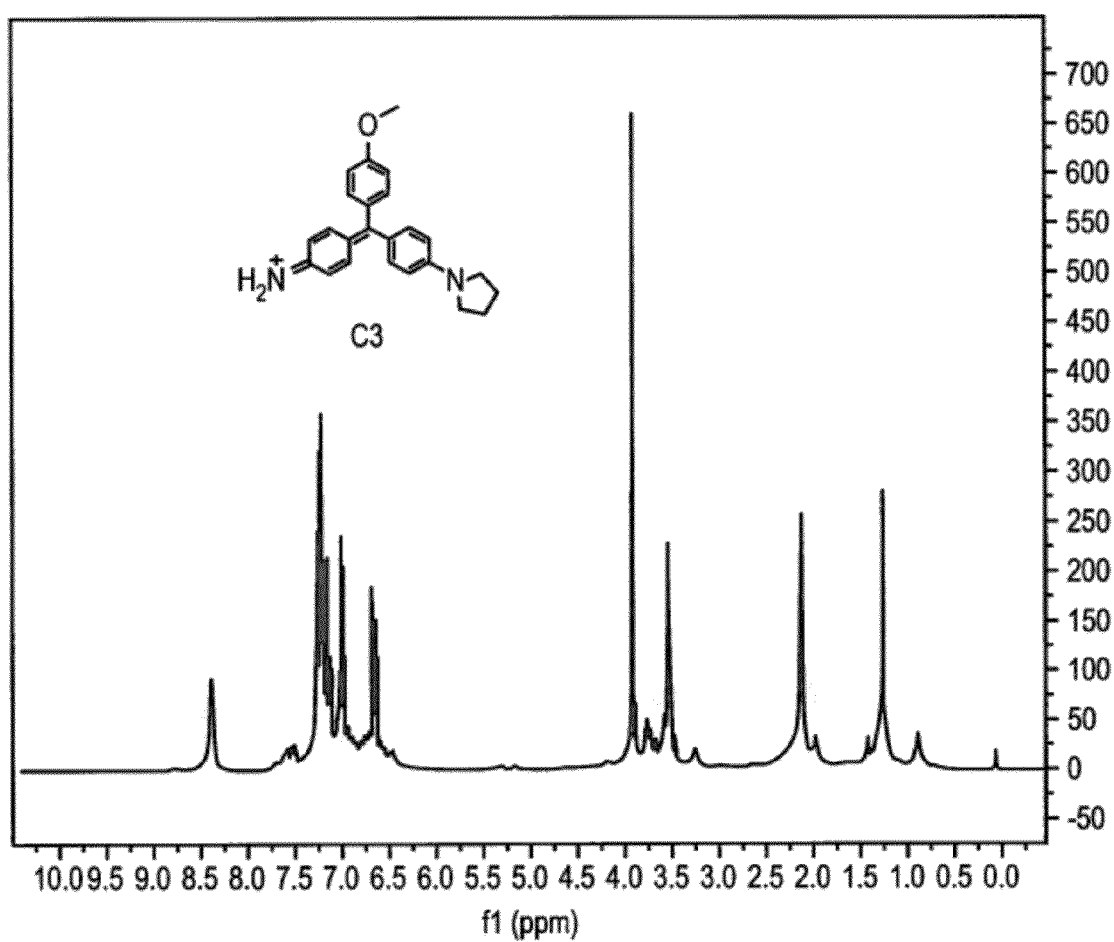
Figure 7:
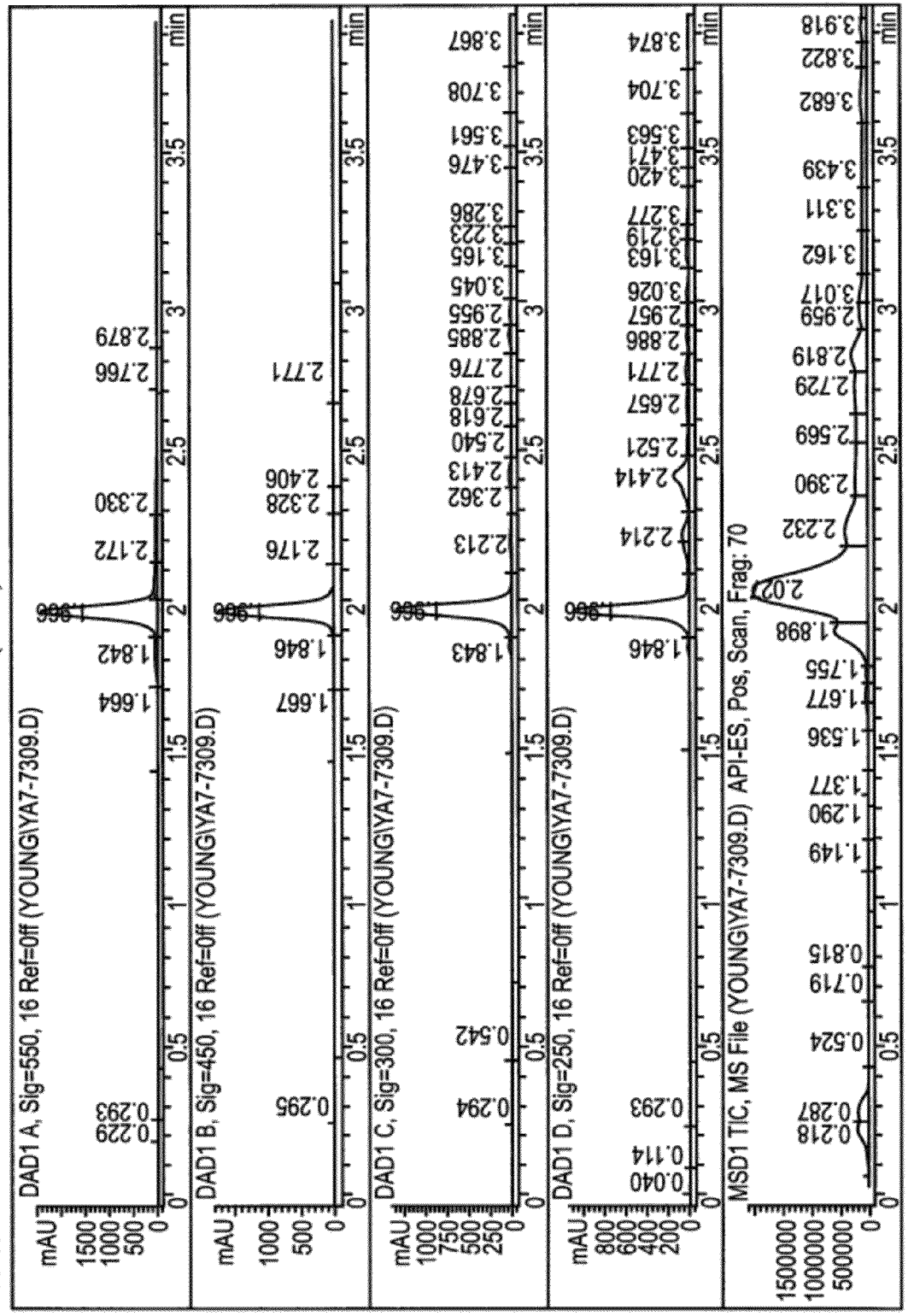
Figure 7:
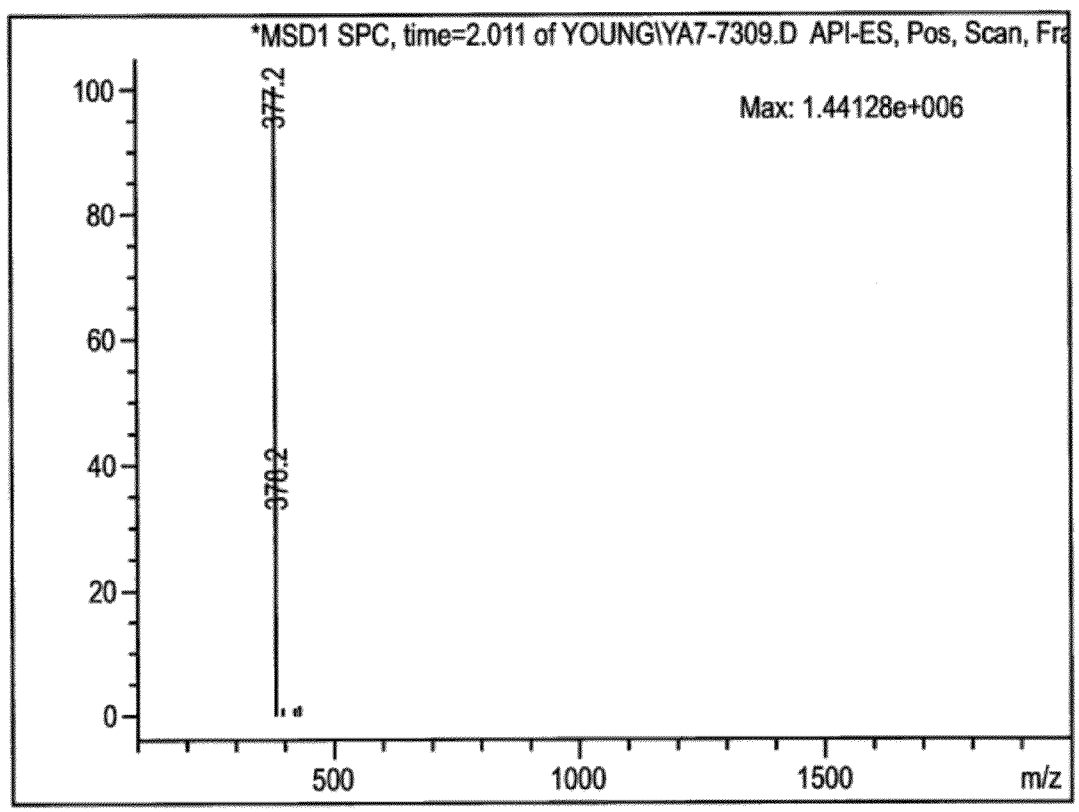
Figure 7:
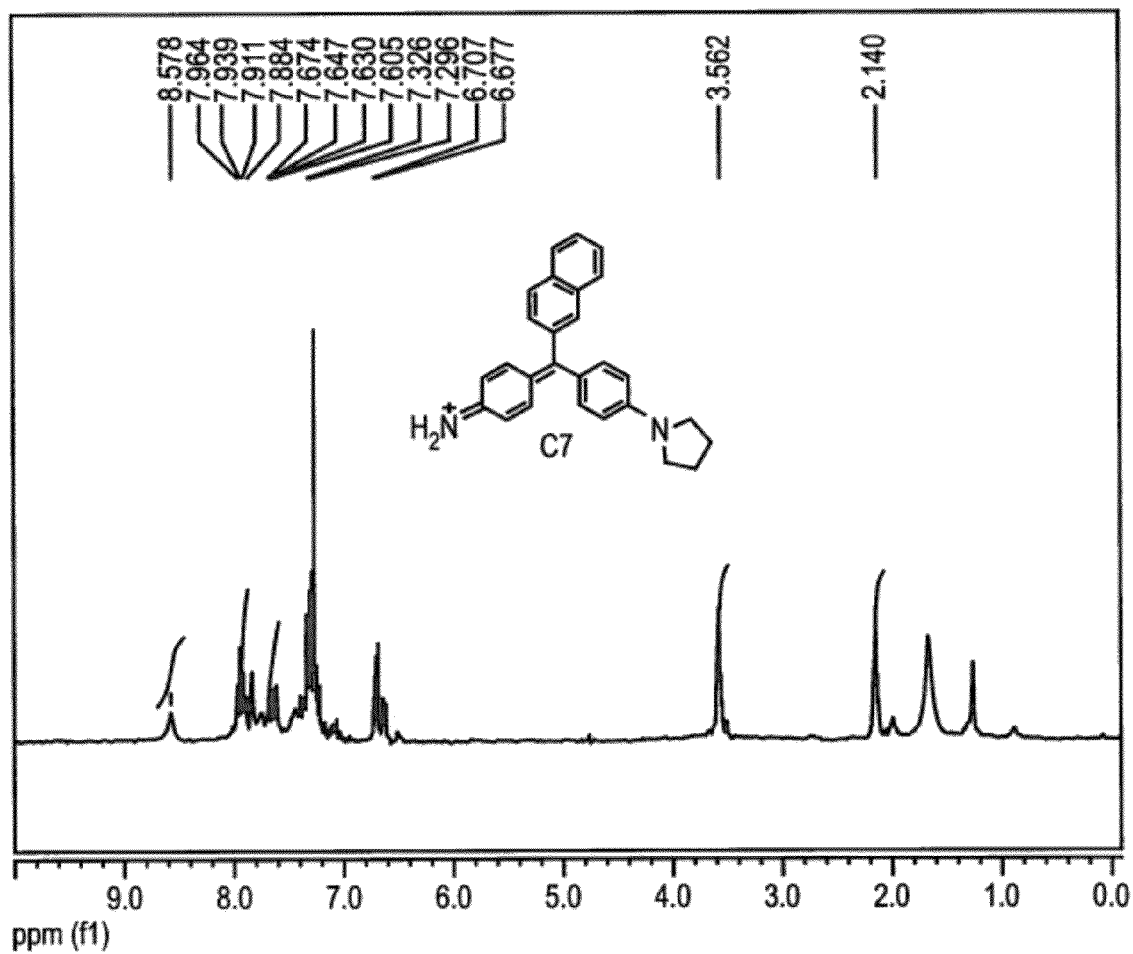
Figure 7:
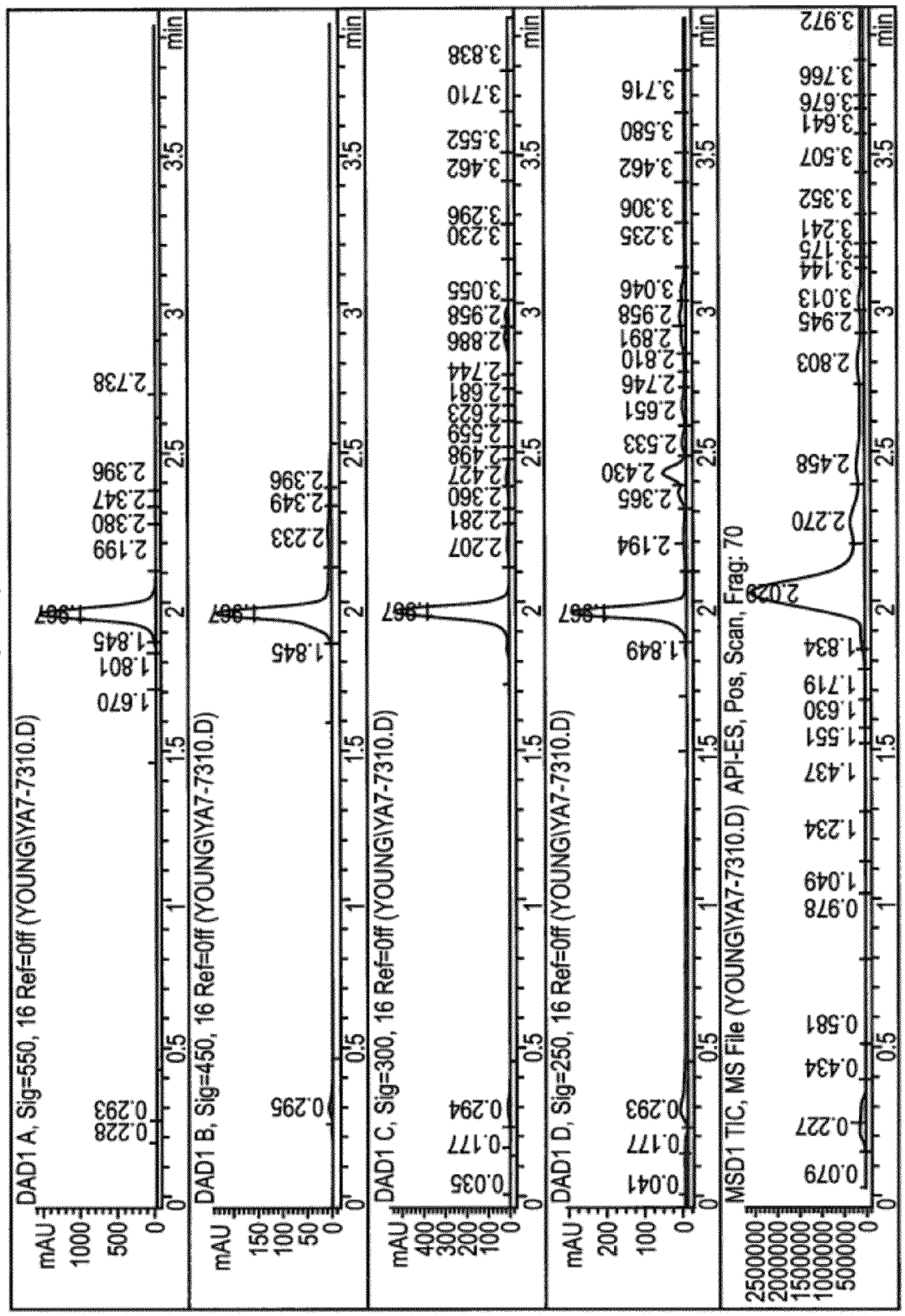
Figure 7:
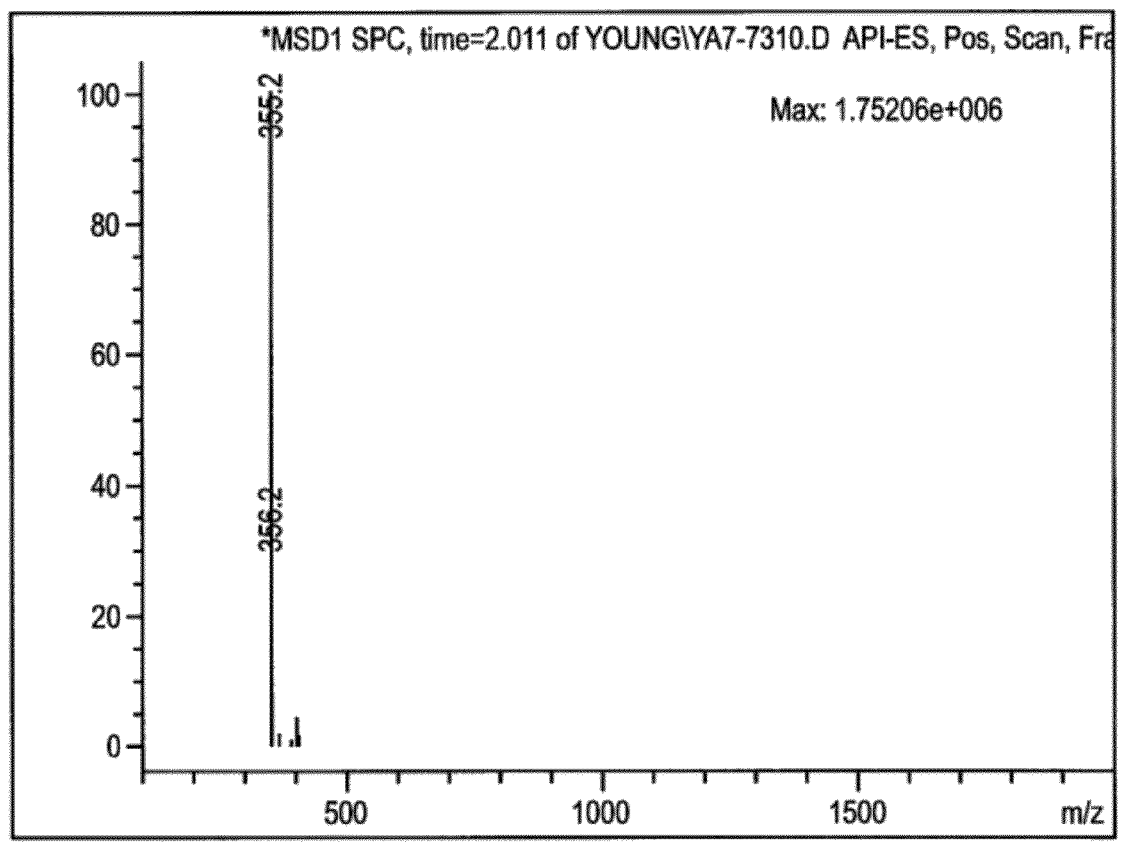
Figure 7:
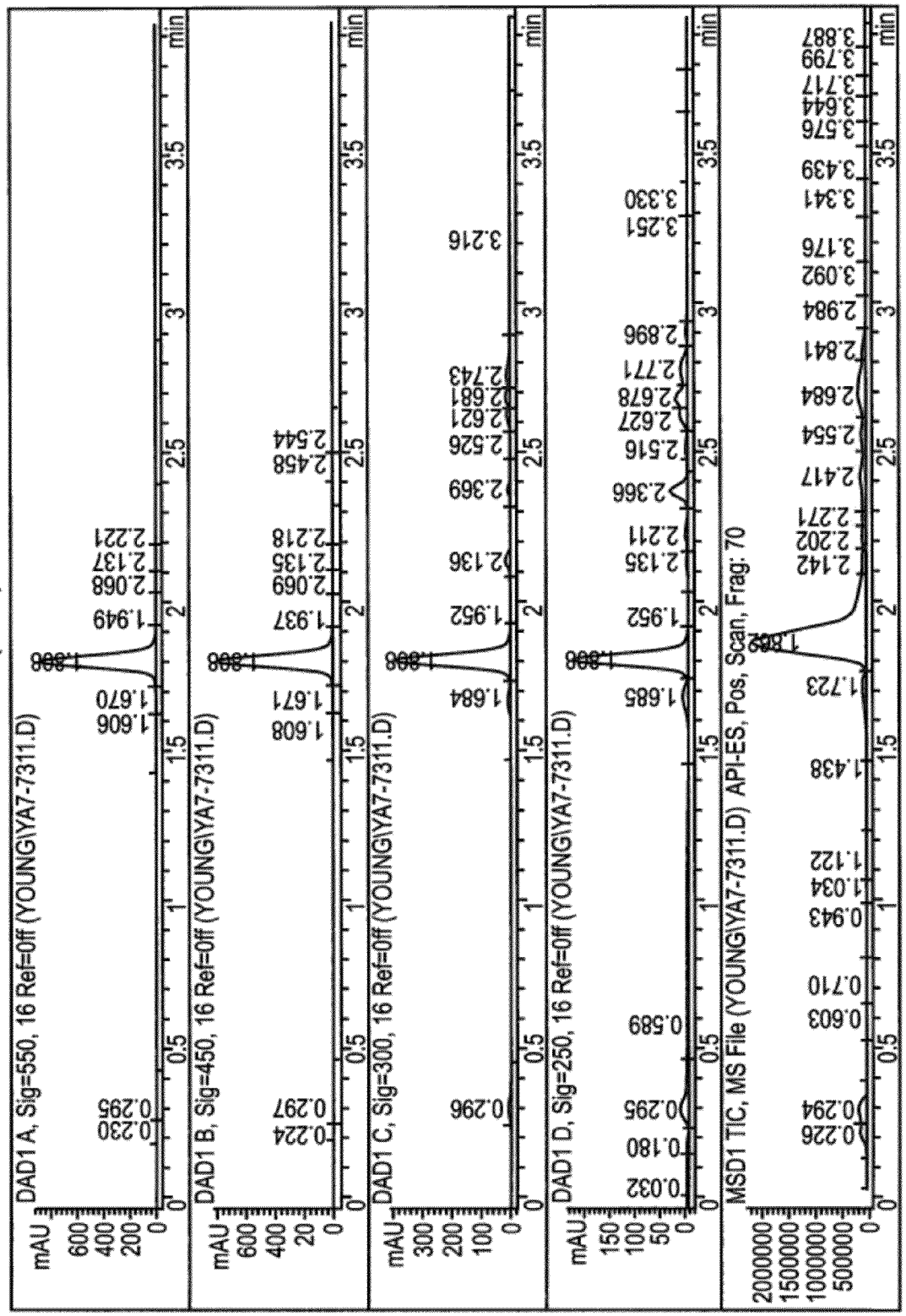
Figure 7:
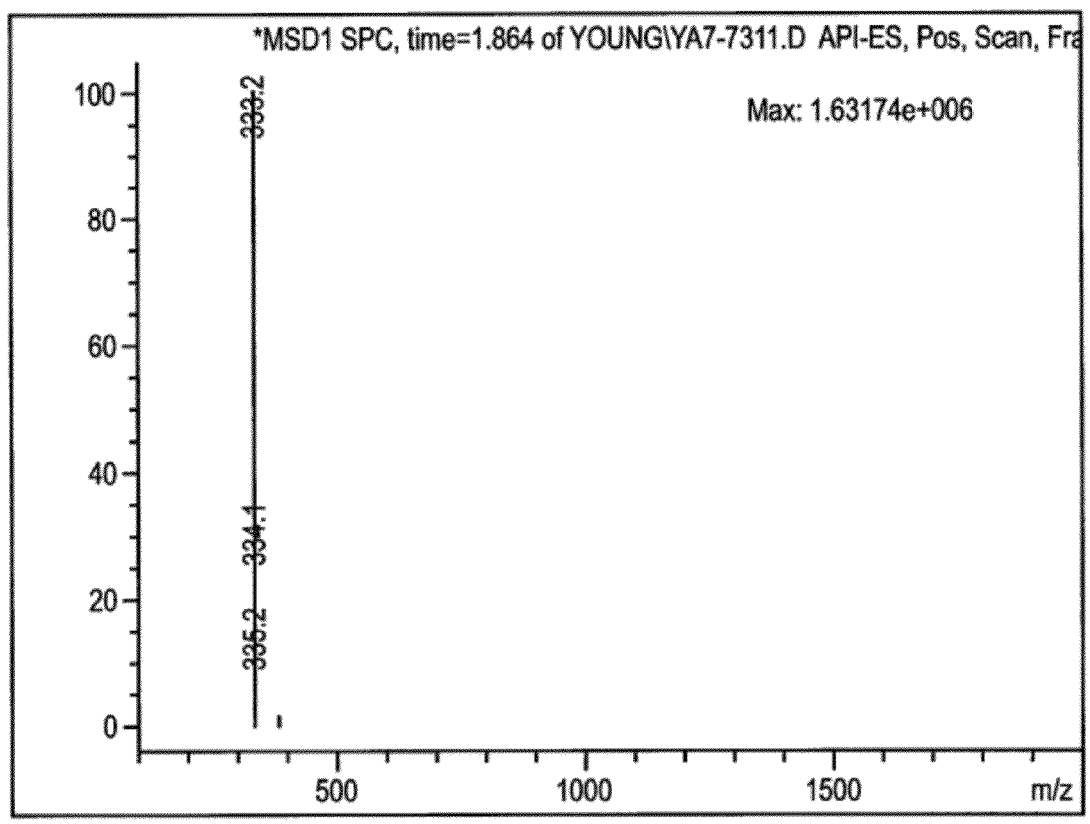
Figure 7:
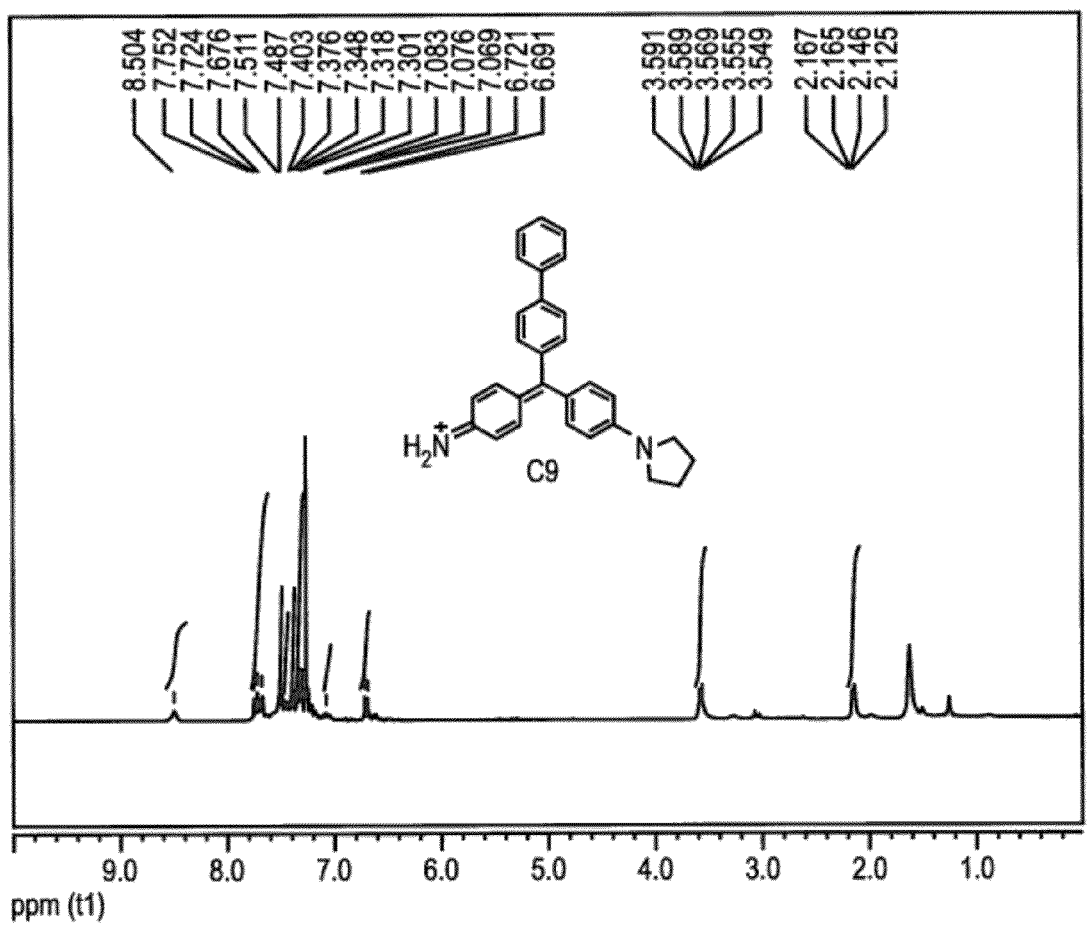
Figure 7:
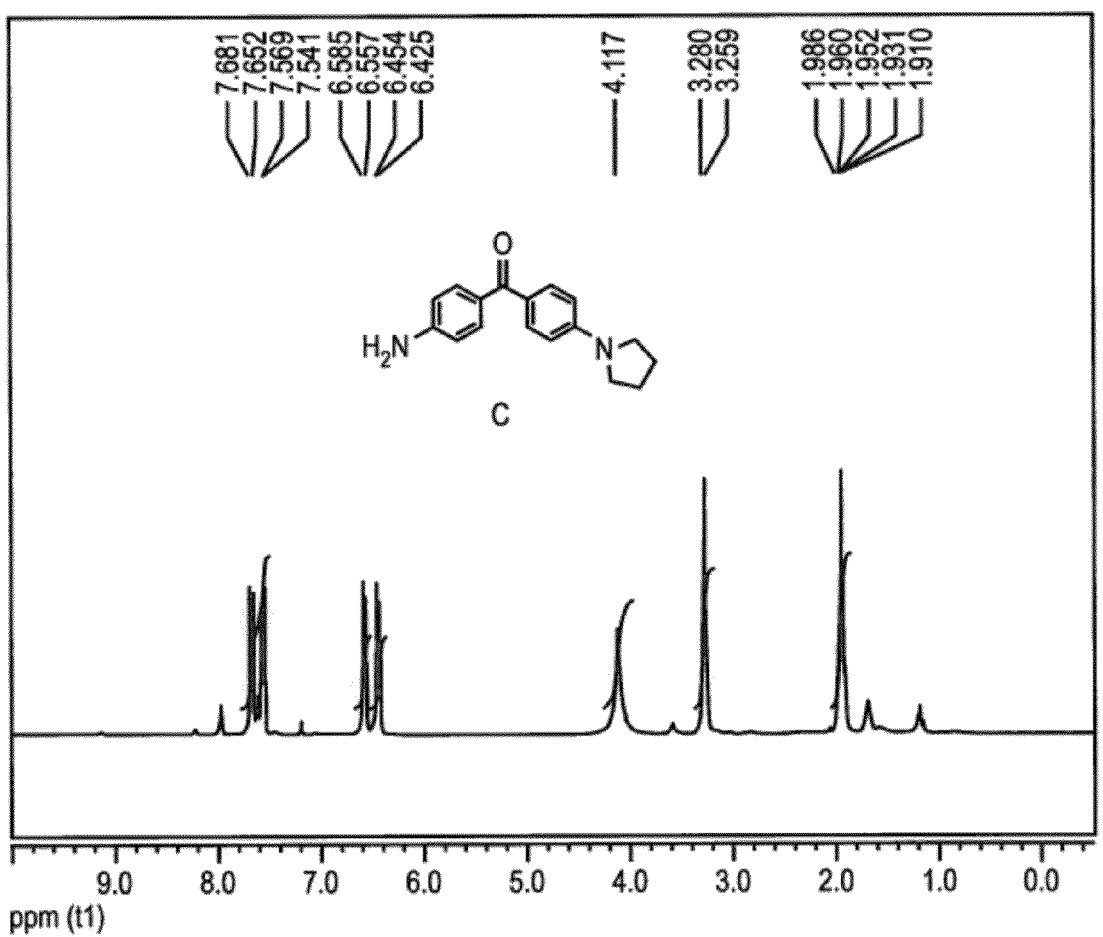

B2: $^1$H-NMR (CDCl$_3$) 10.74 (s, 2H, NH$_2^+$), 8.8.31 (d, J=8.7 Hz, 4H), 7.09 (d, J=8.7 Hz, 4H), 6.68 (d, J=8.7 Hz, 4H), 2.96 (s, 12H); $^{13}$C-NMR (CDCl$_3$): 31.18 [N(CH$_3$)$_2$], 31.81 [N(CH$_3$)$_2$], 109.10, 112.12, 118.79, 125.05, 128.4, 130.71, 135.10, 138.91, 145.47, 150.89, 54.41, 165.00, 176.85 ppm; HRMS (ESI): m/z calcd for C$_{23}$H$_{26}$N$_3$: 344.2121. found: 345.2133 [M+H]$^+$; UV (H$_2$O): δ$_{max}$ (ε): 614 nm (48000 cm$^{-1}$ M$^{-1}$);

B7: $^1$H-NMR (CDCl$_3$) 9.07 (s, 2H, NH$_2^+$), 7.95-7.87 (m, 4H), 7.68-7.59 (m, 3H), 7.26 (d, J=9 Hz, 2H), 6.76 (d, J=9 Hz, 2H), 3.21 (s, 6H); $^{13}$C-NMR (CDCl$_3$): 38.54 [N(CH$_3$)$_2$], 110.29, 116.26, 125.10, 125.51, 125.96, 126.15, 127.12, 127.44, 128.29, 130.53, 133.27, 134.26, 135.12, 137.35, 140.53, 153.16, 159.61, 174.12 ppm; HRMS (ESI): m/z calcd for C$_{25}$H$_{23}$N$_2$: 351.4630. found: 352.1895 [M+H]$^+$; UV (H$_2$O): δ$_{max}$ (ε): 594 nm (38000 cm$^{-1}$ M$^{-1}$);

C3: $^1$H-NMR (CDCl$_3$) 8.14 (s, 2H, NH$_2^+$), 7.18-7.25 (m, 6H, aromatic), 7.09 (d, aromatic 2H, J=8.4 Hz), 6.97 (d, 2H, J=8.7 Hz, aromatic), 6.62 (d, 2H, J=9.0 Hz, aromatic), 3.89 (s, 3H), 3.49 (m, 4H), 2.08 (m, 4H); $^{13}$C-NMR (CDCl$_3$): 25.85, 48.30, 55.79, 113.09, 114.15, 117.18, 126.47, 127.30, 131.90, 137.58, 139.66, 142.04, 153.30, 160.28, 164.27, 176.35 ppm; HRMS (ESI): m/z calcd for C$_{24}$H$_{25}$N$_2$O: 357.1961. found: 358.2014 [M+H]$^+$; UV (H$_2$O): δ$_{max}$ (ε): 580 nm (41600 cm$^{-1}$ M$^{-1}$);

C7: $^1$H-NMR (CDCl$_3$) 8.58 (s, 2H, NH$_2^+$), 7.96-7.88 (m, 4H), 7.67-7.60 (m, 3H), 7.31 (d, J=9 Hz, 2H), 6.69 (d, J=9 Hz, 2H), 3.56 (s, 4H), 2.14 (s, 4H); $^{13}$C-NMR (CDCl$_3$): 25.47, 48.49, 113.24, 117.82, 127.48, 127.91, 128.06, 128.10, 129.02, 129.37, 130.24, 132.48, 135.22, 136.27, 137.07, 139.91, 142.20, 153.50, 161.24, 176.61 ppm; HRMS (ESI): m/z calcd for C$_{27}$H$_{25}$N$_2$: 377.2012. found: 378.2047 [M+H]$^+$; UV (H$_2$O): δ$_{max}$ (ε): 594 nm (59500 cm$^{-1}$ M$^{-1}$);

C9: $^1$H-NMR (CDCl$_3$) 8.50 (s, 2H, NH$_2$$^+$), 7.75-7.68 (m, 2H), 7.51-7.30 (m, 12H), 7.08-7.07 (m, 1H), 6.70 (d, 2H), 3.57 (s, 4H), 2.16 (s, 4H); $^{13}$C-NMR (CDCl$_3$): 23.45, 46.31, 110.65, 111.31, 115.35, 125.03, 125.80, 127.22, 130.88, 132.03, 137.51, 138.76, 139.22, 140.29, 154.24, 162.48, 172.26 ppm; HRMS (ESI): m/z calcd for C$_{29}$H$_{27}$N$_2$: 403.2169. found: 404.2209 [M+H]$^+$; UV (H$_2$O): $\delta_{max}$($\epsilon$): 592 nm (34000 cm$^{-1}$ M$^{-1}$);

FIG. 5 is a graph showing the UV-Vis spectra of the synthesized compounds B2, B7, C3, C7, C9 and CV. FIG. 6 is (A) a graph showing the SERS spectra of B2, B7, and C7, and (B) a table showing unique identifiable peaks attributable to each of the three curves (cm$^{-1}$). FIG. 7 are liquid chromatography mass spectrometry (LCMS) data of some of the synthesized triphenylmethine compounds and intermediate: (A)(i) and (ii) A-2; (B)(i) and (ii) A-13; (C)(i), (ii) and (iii) B-2; (D)(i) B-4; (E)(i), (ii) and (iii) B-7; (F)(i) and (ii) B-16; (G)(i) and (ii) B-25; (H)(i), (ii) and (iii) C-3; (I)(i), (ii) and (iii) C-7; (J)(i) and (ii) C-16; (K)(i) and (ii) C-28; (L) C9 and (M) intermediate C.

Example 13

Modification of TM Compounds with Lipoic Acid

Example 13.1

Synthesis of Lipoic Acid (10)

Diisopropylethylamine (DIPEA) (anhydrous, 4.3 ml, 24.2 mmol) was added to a solution of EDC.HCl (604 mg, 3.15 mmol) in dichloromethane (15 ml) and stirred for 10 minutes. N-hydroxysuccinimide (390 mg, 3.39 mmol) was added followed by DL-lipoic acid (500 mg, 2.43 mmol). The reaction mixture was stirred in an ice bath for half an hour and then slowly continued overnight under room temperature. The reaction mixture was washed with HCl (5% v/v, 25 ml×2) and water (50 ml×3). The organic layer was dried over Na$_2$SO$_4$, filtered and concentrated. The crude residue was purified by silica gel column chromatography (ethylacetate/hexane=2:1) (618 mg, 85%); $^1$H-NMR (CDCl$_3$) 1.62-1.98 (7H, m), 2.29-2.47 (1H, m), 2.69 (2H, t, J=7.4), 3.02 (4H, s, succinimidyl CH$_2$×2), 3.21-3.28 (2H, m), 3.60-3.65 (1H, m); ESI-MS m/z calcd for C$_{12}$H$_{17}$NO$_4$S$_2$: 303.2518. found: 304.1861 [M+1].

Example 13.2

General Procedure for Coupling Between Lipoic Acid (10) and TM Compounds

Catalytic amount of diisopropylethylamine (DIPEA) was added respectively to a solution of TM compound (B2, B7, C3, C7 and C9) (1 eqv.) and activated ester of lipoic acid (1.3 eqv.) in dichloromethane. Each reaction mixture was stirred under nitrogen (N$_2$) atmosphere for 24 to 30 hours. Subsequently, each reaction mixture was concentrated and crude residue was purified by silica gel flash column chromatography. A yield of about 20 to 45% was obtained, with dichloromethane/MeOH=10:1 (v/v).

Upon reaction with lipoic acid (10), the TM compounds B2, B7, C3, C7 and C9 translates into B2LA, B7 LA, C3 LA, C7 LA and C9LA respectively.

Example 14

Raman Microscopy of TM-LA Compounds and SERS Measurement of TM-LA-Gold Colloid Mixture The spectral measurements of the synthesized TM-LA compounds were carried out using a Renishaw InVia Raman (UK) microscope with settings as detailed in Example 8.

The same procedure outlined in Example 9 was used to incubate TM-LA compounds with gold nanoparticles. For Raman measurements, experiments were repeated five times and the average intensities were calculated.

Figure 8:
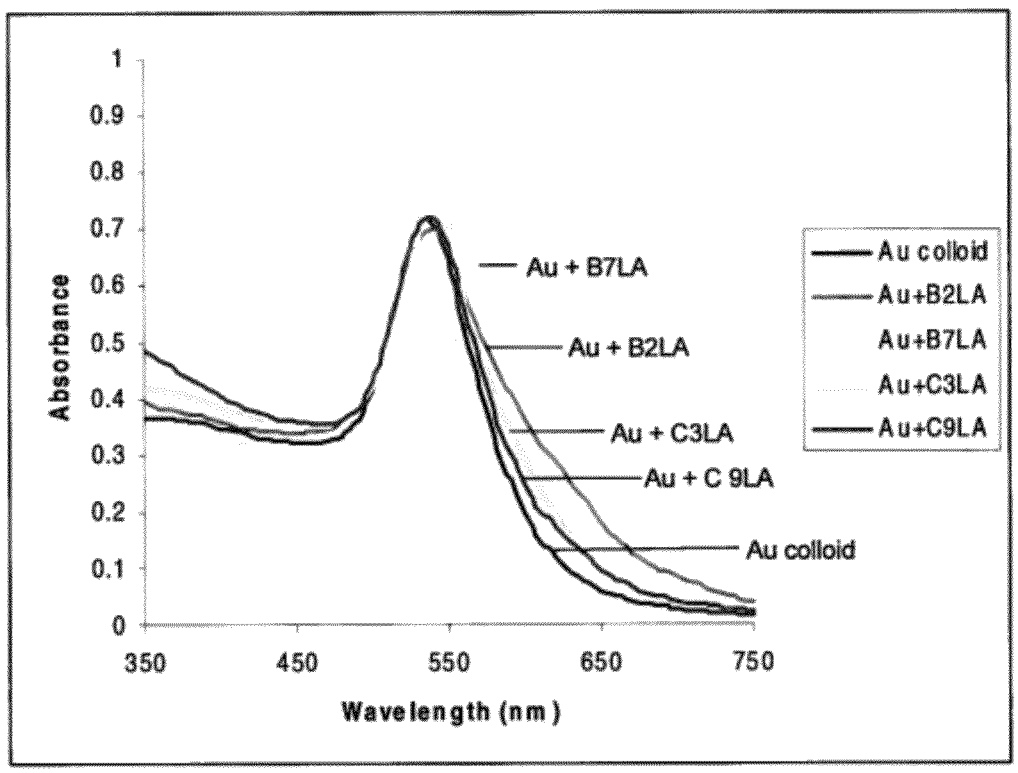
FIG. 8 is a graph showing surface plasmon absorption spectra of gold (Au) colloid and nanotag containing Raman reporters.

FIG. 8 is a graph showing surface plasmon absorption spectra of gold (Au) colloid and nanotag containing Raman reporters.

Example 15

Modification of TM-LA Compound-Gold Nanoparticle Nanotags with Thiolated PEG

Freshly prepared reporter solutions with various concentrations (5, 10, 20, 30 µM) was rapidly mixed with gold colloid in a 1:9 ratio (v/v). This molar ratio of reporter molecules was optimized to a concentration of 5 to 10 µM by maximizing SERS intensities and minimum colloidal aggregation. The surface coverage values for the synthesized Raman reporters was estimated based on the established method outlined in Liz-Marzan et al. (Liz-Marzan et al., 1996, Langmuir, 12, 4329-4335) which showed that around 15440 (B2LA), 13600 (B7LA), 11200 (C7LA), 11800 (C3LA) and 9800 (C9LA) molecules were adsorbed per Au (60 nm) nanoparticle. After 5 minutes of incubation, thiolated PEG (PEG-SH, molecular weight of PEG (M.W.$_{PEG}$): 5000 Da, RAPP Polymere GmbH) solution (100 µM) was added around 10 to 20-fold excess in order to get maximum surface coverage. After overnight incubation, the excess PEG-SH was removed by three rounds of centrifugation (8000 rpm for 3 minutes) and re-suspended in water.

Example 16

$^1$H-NMR, $^{13}$C-NMR, HRMS (ESI), and UV-Vis data of TM-LA Raman Reporters B2LA, B7LA, C3LA, C7LA and C9LA $^1$H-NMR, $^{13}$C-NMR, HRMS (ESI), and UV-Vis data of TM-LA Raman reporter compounds are provided as follows.

B2LA: (CDCl$_3$): 8.41 (d, J=8.7 Hz, 2H), 8.11 (d, J=8.2 Hz, 2H), 7.94 (d, J=7.9 Hz, 2H), 7.83 (t, J=8.3 Hz, 2H), 7.55-7.42 (m, 2H), 7.43-7.38 (m, 2H), 3.68-3.58 (m, 1H), 3.20-3.14 (m, 2H), 2.90 (t, J=8.8 Hz, 2H), 2.55-2.39 (m, 2H), 2.02 (s, 6H, N(CH$_3$)$_2$), 1.86-1.55 (m, 6H); $^{13}$C-NMR (CDCl$_3$): 24.40, 24.41, 29.58, 30.18 [N(CH$_3$)$_2$], 31.81[N(CH$_3$)$_2$], 34.34, 34.72, 38.48, 40.14, 56.00, 109.10, 116.12, 118.79, 125.05, 129.4, 130.71, 134.19, 136.98, 144.40, 169.90, 169.66 ppm; MS (ESI): m/z calcd for C$_{31}$H$_{38}$N$_3$OS$_2$: 532.2456. found: 533.4321 [M+H]$^+$; UV (H$_2$O): $\delta_{max}$ ($\epsilon$): 620 nm (43000 cm$^{-1}$ M$^{-1}$);

B7LA: $^1$H-NMR (CDCl$_3$) 7.94-7.89 (m, 4H), 7.62-7.58 (m, 3H), 7.26-7.22 (m, 2H), 6.61 (t, J=8.3 Hz, 2H), 3.58-3.55 (m, 1H), 3.16-3.04 (m, 2H), 2.65-2.29 (m, 4H), 2.11 (s, 3H, N(CH$_3$)$_2$), 1.88-1.45 (m, 6H); $^{13}$C-NMR (CDCl$_3$): 38.54 [N(CH$_3$)$_2$], 110.29, 116.26, 125.10, 125.51, 125.96, 126.15, 127.12, 127.44, 128.29, 130.53, 133.27, 134.26, 135.12, 137.35, 140.53, 153.16, 159.61, 174.12 ppm; MS (ESI): m/z calcd for C$_{33}$H$_{36}$N$_2$OS$_2$: 539.7738. found: 540.4571[M+H]$^+$; UV (H$_2$O): $\delta_{max}$ ($\epsilon$): 617 nm (48000 cm$^{-1}$ M$^{-1}$);

C3LA: $^1$H-NMR (CDCl$_3$) 7.44-7.23 (m, 4H), 7.18-6.97 (m, 4H), 6.86-6.72 (m, 2H), 6.48 (d, J=8.1 Hz, 2H), 3.62-3.53 (m, 1H), 3.46-3.11 (m, 4H), 2.89 (s, 3H), 2.65 (t, J=8.1 Hz, 2H), 2.52-2.33 (m, 4H), 2.02-1.49 (m, 6H); $^{13}$C-NMR (CDCl$_3$): 25.85, 48.30, 55.79, 113.09, 114.15, 117.18, 126.47, 127.30, 131.90, 137.58, 139.66, 142.04, 153.30, 160.28, 164.27, 176.35 ppm; MS (ESI): m/z calcd for $C_{32}H_{38}N_2O_2S_2$: 546.2375. found: 547.3481 [M+H]$^+$; UV (H$_2$O): $\delta_{max}$ ($\epsilon$): 588 nm (39000 cm$^{-1}$ M$^{-1}$);

C7LA: $^1$H-NMR (CDCl$_3$) 7.86-7.70 (m, 4H), 7.56-7.41 (m, 5H), 7.26 (d, J=8.1 Hz, 2H), 7.11 (d, J=8.8 Hz, 2H), 6.66 (d, J=8.3 Hz, 2H), 6.45 (d, J=8.7 Hz, 2H), 3.58-3.54 (m, 1H), 3.39-3.19 (m, 4H), 2.84-2.76 (m, 2H); 2.02-1.39 (m, 12H); MS (ESI): m/z calcd for $C_{35}H_{37}N_2OS_2$: 565.2347. found: 566.2441 [M+H]$^+$; UV (H$_2$O): $\delta_{max}$ ($\epsilon$): 602 nm (54000 cm$^{-1}$ M$^{-1}$);

C9LA: $^1$H-NMR (CDCl$_3$) 7.75-7.28 (m, 12H), 7.02 (d, J=7.9 Hz, 2H), 6.48 (d, J=8.2 Hz, 2H), 3.57-3.51 (m, 1H), 3.26-2.86 (m, 4H), 2.54 (t, J=8.3 Hz, 2H), 2.48-2.42 (m, 2H), 1.84-1.31 (m, 12H); MS (ESI): m/z calcd for $C_{37}H_{39}N_2OS_2$: 591.2504. found: 592.0321 [M+H]$^+$; UV (H$_2$O): $\delta_{max}$ ($\epsilon$): 594 nm (49000 cm$^{-1}$ M$^{-1}$);

Example 17

UV-Vis Spectra and SERS Spectra of Synthesized TM-LA Raman Reporters

Figure 9:
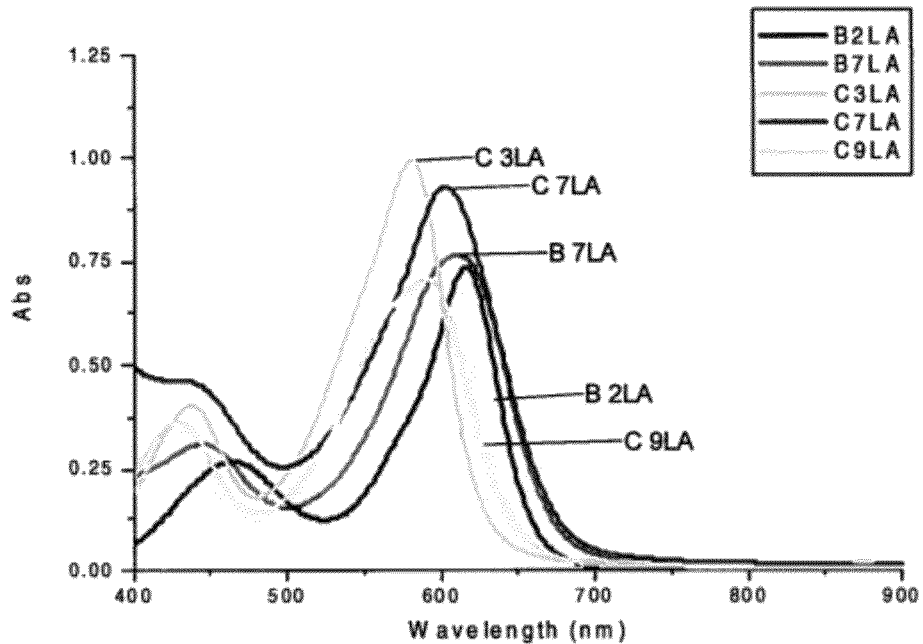
FIG. 9 is a graph showing the UV-Vis spectra of the synthesized TM-LA Raman reporters (A) B2LA; (B) B7LA; (C) C3LA; (D) C7LA; and (E) C9LA compounds.

FIG. 9 is a graph showing the UV-Vis spectra of the synthesized TM-LA Raman reporters (A) B2LA; (B) B7LA; (C) C3LA; (D) C7LA; and (E) C9LA compounds.

Figure 10A:
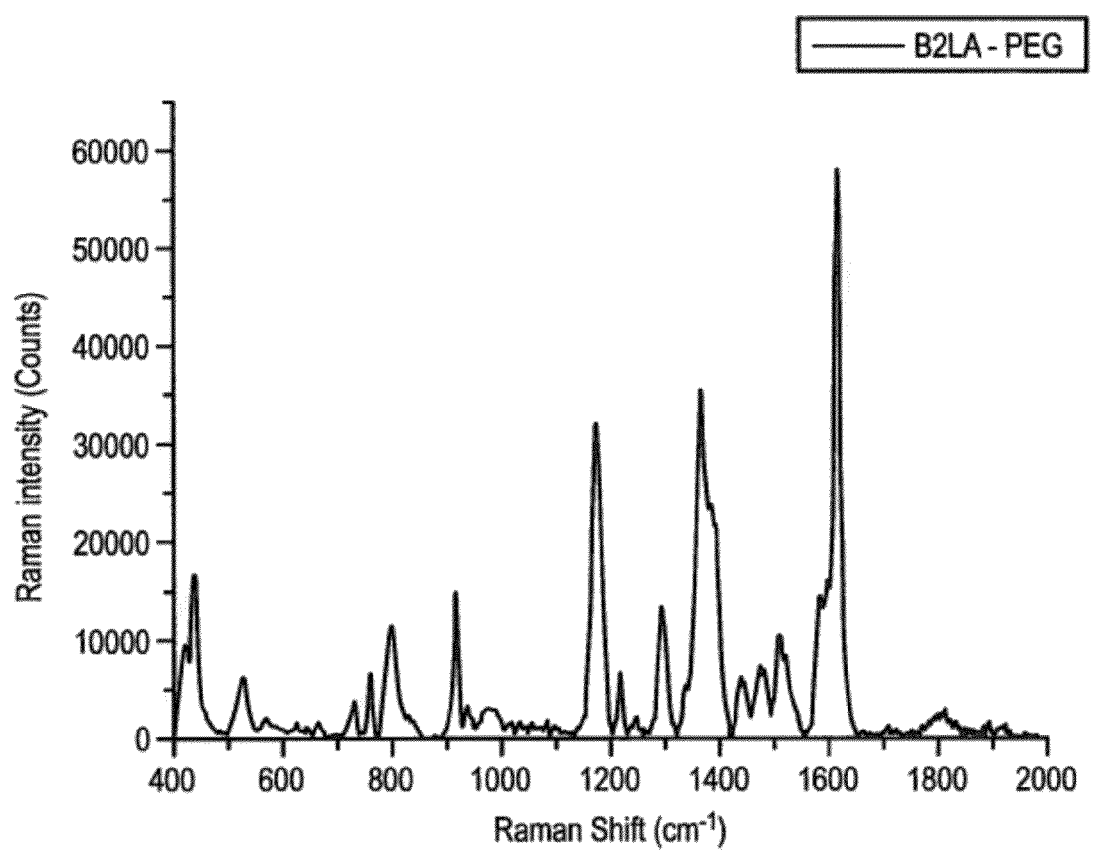
FIG. 10 are graphs showing the SERS spectra of PEG encapsulated nanotags of (A) B2LA reporter molecules, and (B) MGITC reporter molecules. SERS spectra were obtained with 633 nm laser excitation at 6.2 mW.
Figure 10B:
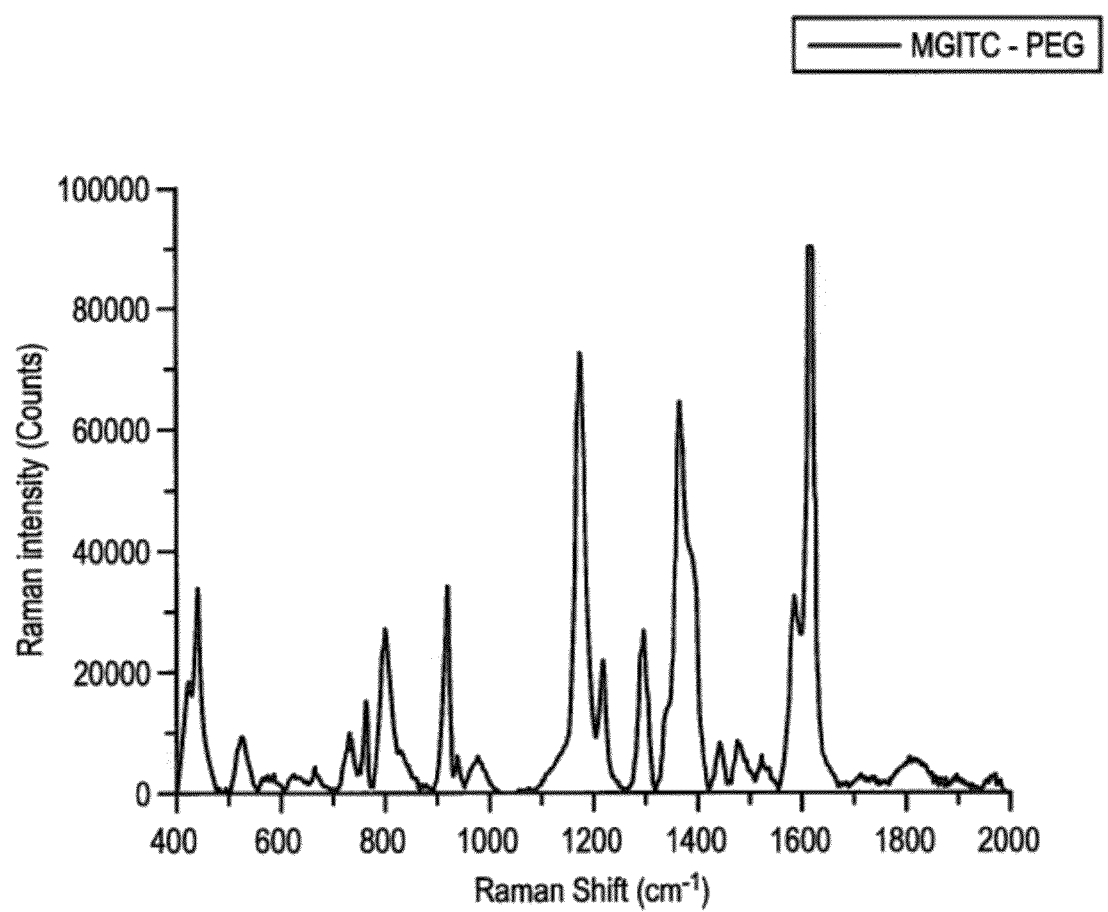

FIG. 10 is a graph showing the SERS spectra of PEG encapsulated nanotags with (A) B2LA and (B) MGITC reporter molecules. SERS spectra were obtained with 633 nm laser excitation at 6.2 mW.

Figure 11:
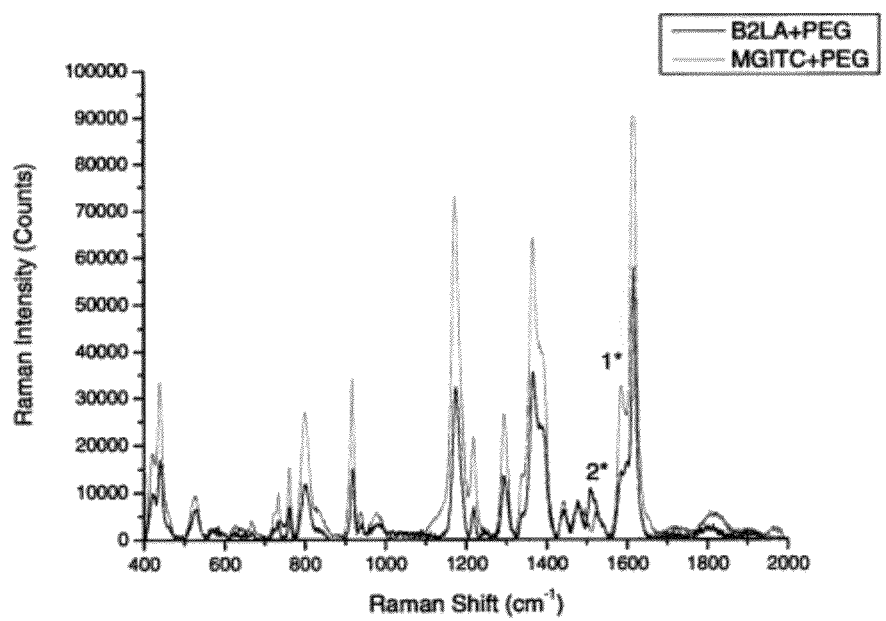
FIG. 11 is a graph showing overlapped SERS spectra of B2LA and MGITC-containing nanotag with identifiable peaks ($cm^{-1}$). The SERS spectra obtained with these two dyes containing nanotag have a similar pattern, which may be due to the triphenylmethine moiety present in both molecules. In addition, there was little difference between the SERS spectra obtained for the two molecules as can be seen from the overlapped SERS spectra. [1*-1590 $cm^{-1}$ (present in MGITC); 2*-1510 $cm^{-1}$ (present in B2LA)].

FIG. 11 is a graph showing overlapped SERS spectra of B2LA and MGITC-containing nanotag with identifiable peaks (cm$^{-1}$). The SERS spectra obtained with these two dyes containing nanotag have a similar pattern, which may be due to the common basic skeleton i.e triphenylmethine moiety for both molecules. Moreover, little difference between two molecules when both the SERS spectra was overlapped was observed. [1*-1590 cm$^{-1}$ (present in MGITC); 2*-1510 cm$^{-1}$ (present in B2LA)].

Example 18

Antibody Conjugation on Gold Nanoparticle (Au-NP)

First, the reporter molecule B2LA (10 μm) was mixed with citrate stabilized Au-colloid and the mixture was incubated for 10 minutes to allow sufficient adsorption of reporter molecules on Au-colloid. The heterofunctional linker HS-PEG-CO$_2$H (10 μM) was added to 2.6 ml of Au-B2LA solution in a polypropylene tube with rapid mixing. After 15 minutes of mixing, the Au-colloid was exposed to excess of PEG-SH (1.8 ml, 10 μM) to maximize its surface coverage and to stabilize the PEG, and the chemisorbed reporter molecule. Free PEG-SH was removed after 3 hours of thorough mixing by three rounds of centrifugation (4000 rpm, 15 min) and re-suspended in phosphate buffered saline (PBS) which was ready for covalent conjugation at the carboxyl terminal of heterofunctional PEG. For bioconjugation, the —COOH groups on the particle surface was activated by adding ethyl dimethylaminopropyl carbodiimide (EDC) and N-hydroxy succinimide (NHS) solution (5 μl) at a concentration of 25 mM each respectively. After 30 minutes of mixing, the excess EDC and NHS were separated from the bioconjugation-active nanoparticles by three rounds of centrifugation (8000 rpm, 10 min) and re-suspended in PBS using Amicon Ultra centrifuge filter (3K MWCO, Milipore). The purified Au particles with activated carboxyl groups were then reacted with antibody (EGFR 528, 12 nM, a mouse monoclonal anti-EGFR 1gG$_{2a}$ purchased from Santa Cruz, sc-120) and another antibody (HER2, a mouse monoclonal, purchased from Santa Cruz (Neu (0.N.211) sc-71667) at 25° C. for 2 hours and then stored the antibody conjugated nanotag at 4° C. overnight. Further non-specific binding chemicals and antibodies were removed by centrifugation (8000 rpm, 10 minutes) and final nanotags were resuspended in PBS.

Figure 12:
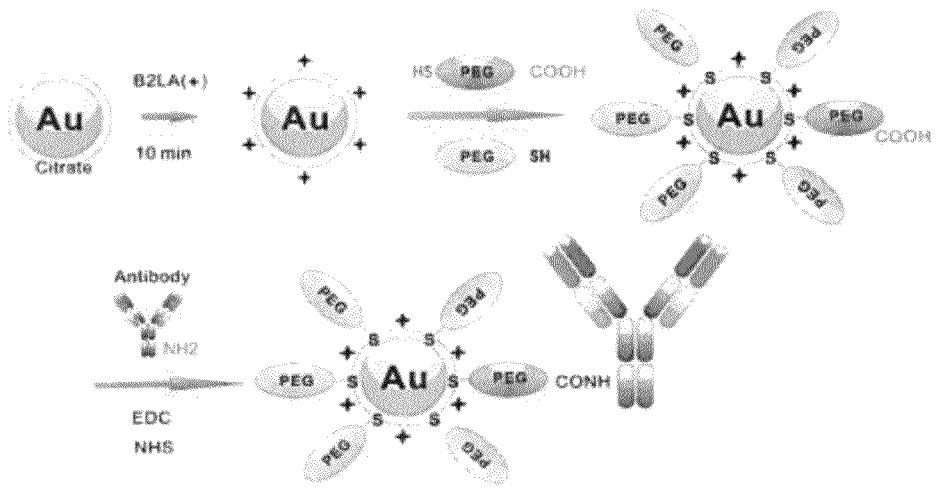
FIG. 12 is a schematic diagram showing the preparation of smart nanoparticle tags attached to an antibody, as well as steps for preparing an antibody conjugate with PEG molecules functionalized with a thiol group (PEG-SH) and heterofunctional PEG molecules functionalized with a thiol group and a carboxyl group (SH-PEG-$CO_2H$).

FIG. 12 is a schematic diagram showing the preparation of smart nanoparticle tags attached to an antibody, as well as steps for preparation of antibody conjugation with PEG-SH and heterofunctional SH-PEG-CO$_2$H.

Figure 13:
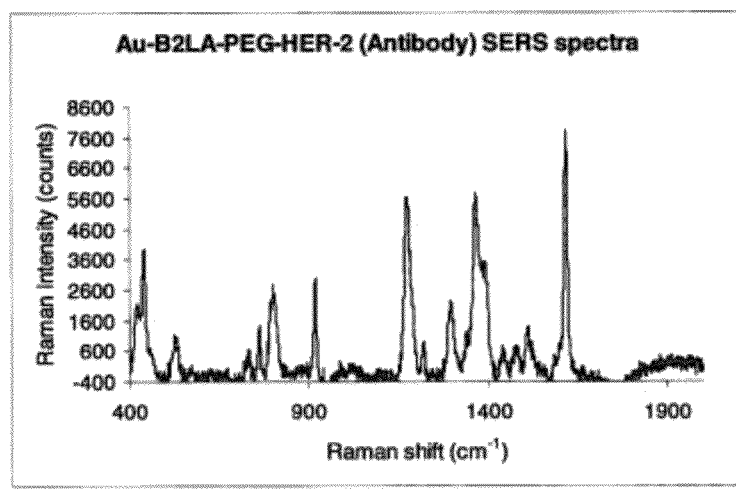
FIG. 13 are graphs showing representative SERS spectra of PEG encapsulated nanotags of reporter molecules B2LA with (A) HER-2 antibody attached; and (B) EGFR antibody attached. SERS spectra were obtained with 633 nm laser excitation; laser power 6.2 mW.
Figure 13:
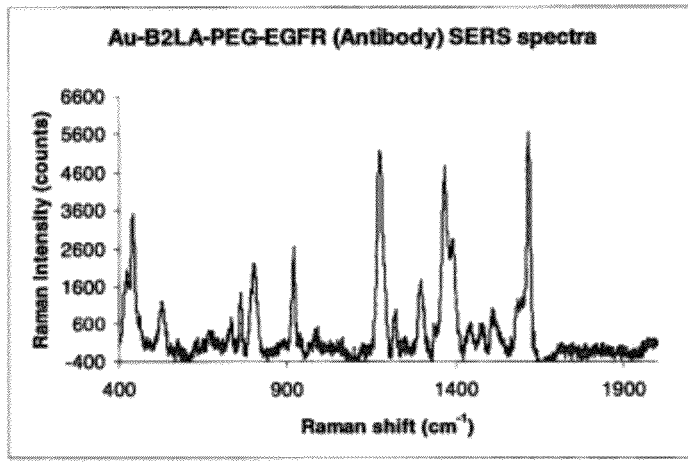

FIG. 13 are graphs showing representative SERS spectra of PEG encapsulated nanotags with reporter molecules B2LA with (A) HER-2 antibody attached; (B) EGFR antibody attached. SERS spectra were obtained with 633 nm laser excitation; laser power 6.2 mW.

Figure 14:
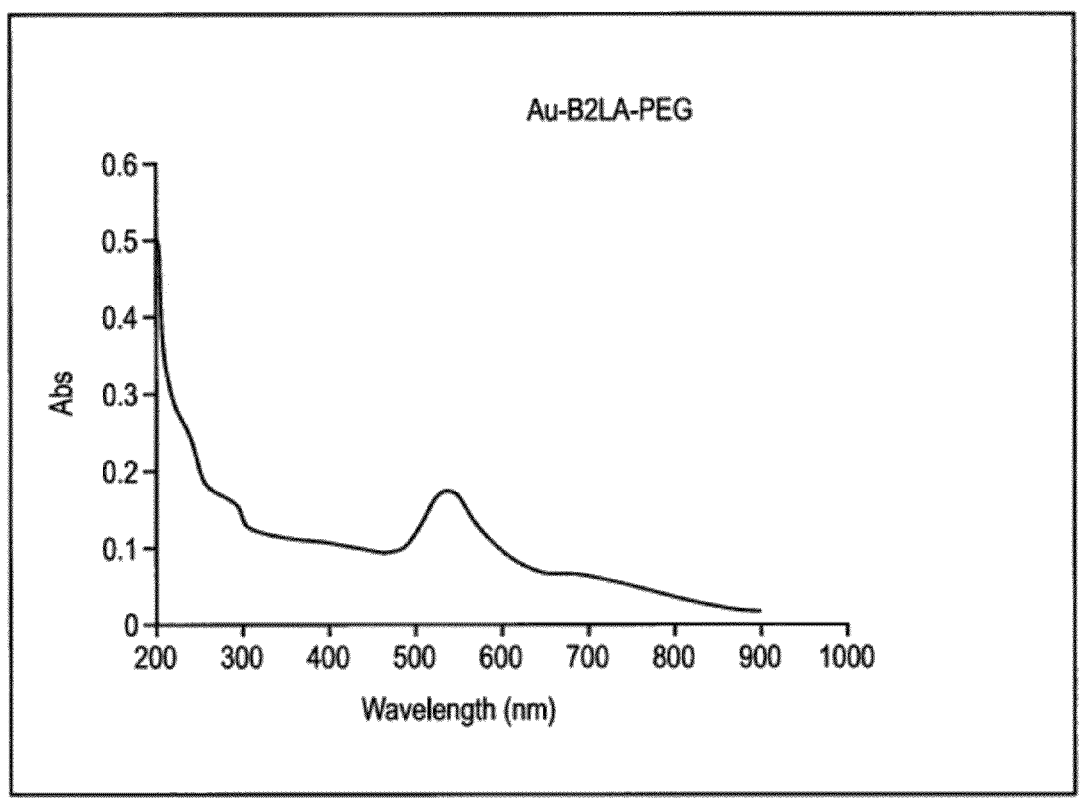
FIG. 14 are graphs showing UV spectra of nanotags (A) without antibody attached (Au-B2LA-PEG); (B) with HER2 antibody attached (Au-B2LA-PEG-HER2).
Figure 14:
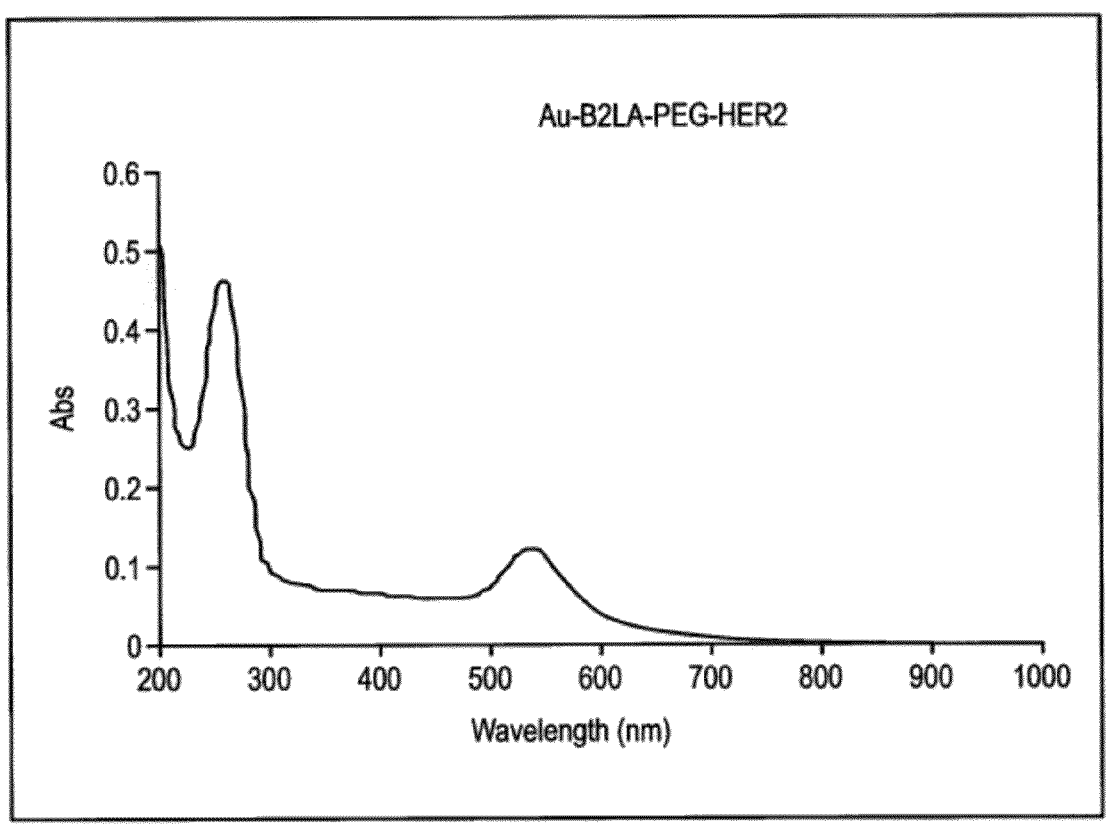

FIG. 14 are graphs showing UV spectra of nanotag attached antibody: (A) Nanotag without antibody attached; (B) HER2 antibody attached nanotag.

Figure 15:
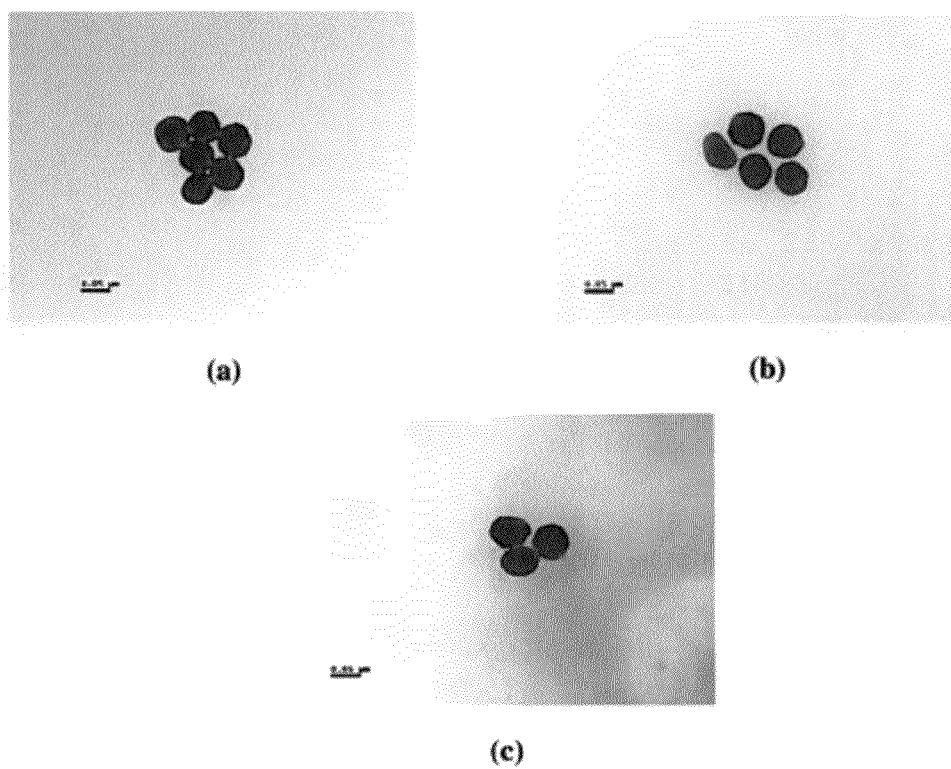
FIG. 15 shows transmission electron microscopy (TEM) images of (A) nanotag without antibody attached (Au-B2LA-PEG); (B) nanotag with HER2 antibody attached (Au-B2LA-PEG-HER2); (C) nanotag with EGFR antibody attached (Au-B2LA-PEG-EGFR).

FIG. 15 shows transmission electron microscopy (TEM) images of (A) Pure nanotag (Au-B2LA-PEG); (B) HER2 antibody attached nanotag; (C) EGFR antibody attached nanotag.

Example 19

Cell Culture

Human cancer cell lines (MCF7, MDA-MB-231, SCC-15, and SKBR-3) were grown in RPMI1640 medium supplemented with 10% (v/v) fetal bovine serum (FBS) and antibiotics (100 Uml$^{-1}$ penicillin/100 μgml$^{-1}$ streptomycin mix) in a humidified atmosphere at 37° C. with 5% (v/v) carbon dioxide (CO$_2$). Cell culture materials (FBS, antibiotics, and 0.25% (v/v) trypsin-EDTA) were purchased from Invitrogen. For live cell imaging, approximately, 5×10$^5$ cells/well were plated on 12-well plate, and antibody-staining and imaging was performed on the following day.

Example 20

Cell Culture

The cell lines for EGFR positive (SCC-15), negative (MCF7) and HER2 positive (SKBR-3), negative (MDA-MB-231) were grown to the above-mentioned procedure in 12-well plate. Antibody conjugated SERS nanotags were gently mixed with live cells and incubated for 1 hour. The cells were harvested by gentle scraping after three round of cold PBS washing and re-suspended with 100 μl of PBS. For control experiment, MCF7 and MDA-MB-231 cells were treated with antibody attached nanotags, while SCC-15 and SKBR-3 cells were incubated with pegylated SERS nanotags (without antibody attached) to assess the non-specific binding. All SERS spectra were taken in cell suspensions based on cell density of 1×10$^6$ cells/ml.

Example 21

In Vivo SERS Detection of SKBR-3 Cells Using HER2 Antibody Anchored Nanotag

SKBR-3 cells cultured in one 10-cm dish at 80% confluency was incubated with nanotag attached HER2 antibody (500 μM) for 1 hour at room temperature. After incubation, cells were washed with media and PBS (×2), gently scrapped and re-suspended in 150 μl PBS. Balb/c nude mice obtained from the Biological Resource Centre, Biomedical Sciences Institutes were anesthetized by intraperitoneal injection of ketamine (150 mg/kg)/xylazine (10 mg/kg) at the age of 8 weeks. The cell suspension containing nanotag attached HER2 antibody was injected subcutaneously in the left rear flank of the two separate mice (injection volume: 150 µl). The subcutaneous spectrum was obtained in 10 s and the control spectrum was taken in an area away from the injected site. The animal experiment procedures were performed in accordance with a protocol approved by the Institutional Animal Care and Use Committee (IACUC).

Example 22

Comparative SERS Intensity of Lipoic Acid Linked TM Compounds (B2LA, B7LA, C3LA, C7LA and C9LA)

We used the active ester of lipoic acid for making covalent linkage with TM dyes through its amine terminal. Based on our results, we chose the best five strong SERS-active reporter molecules (B2, B7, C3, C7 and C9) and linked them to lipoic acid through amide bond formation for inducing chemisorption onto Au-colloid.

Figure 16:
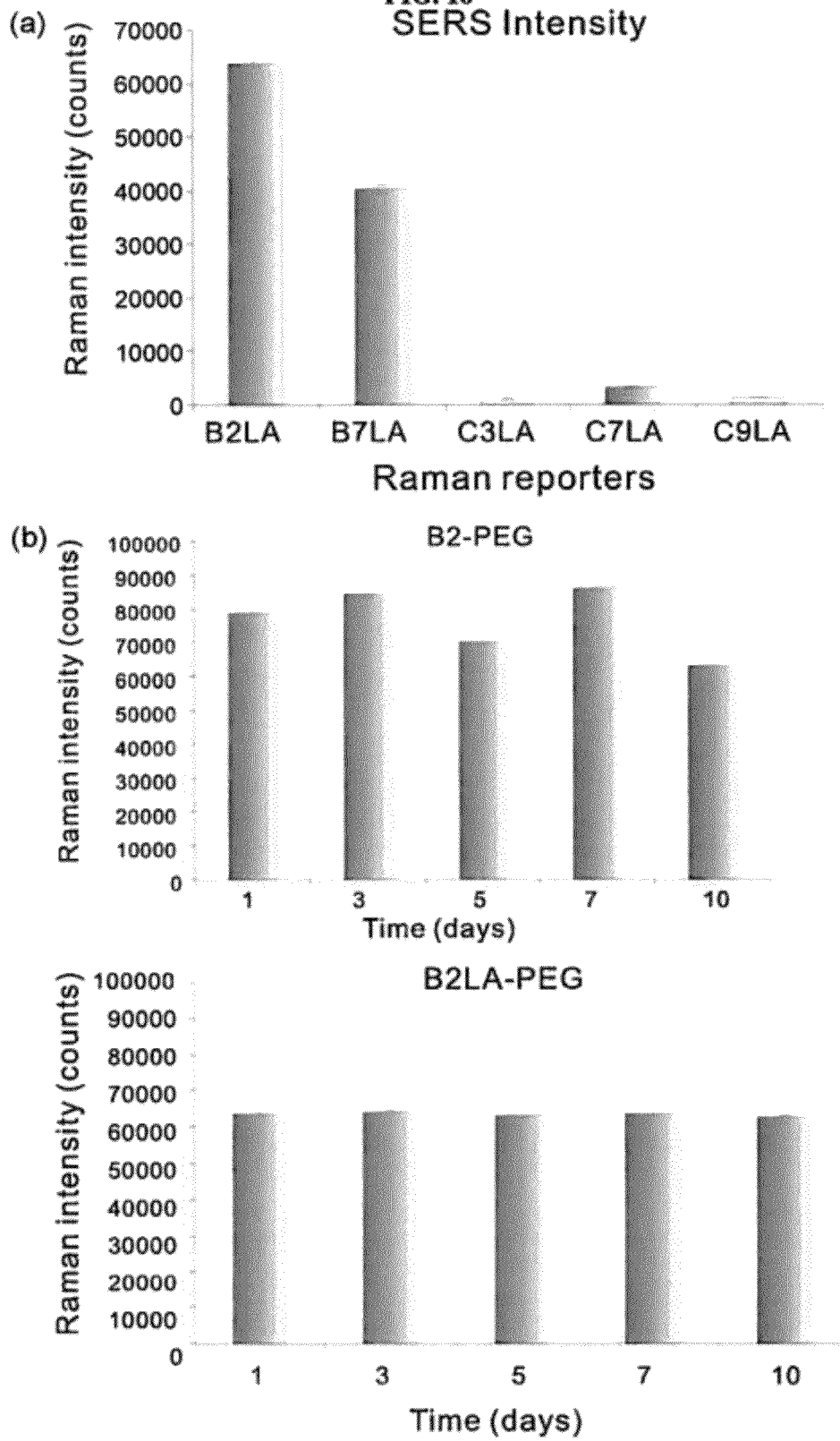
FIG. 16 are graphs showing (A) SERS intensities of lipoic acid conjugated TM compounds (B2LA, B7LA, C3LA, C7LA and C9LA) nanotags. Five individual measurements were made to obtain the average and standard deviation (shown as error bars of intensity values); (B) Time course SERS study of PEG encapsulated B2 and B2LA compounds. Five individual measurements were made to obtain the average and standard deviation (shown as error bars) of intensity values.

FIG. 16 are graphs showing (a) SERS intensities of lipoic acid conjugated TM compounds (B2LA, B7LA, C3LA, C7LA and C9LA) nanotags. Five individual measurements were made to obtain the average and standard deviation (shown as error bars of intensity values); (b) Time course SERS study of PEG encapsulated B2 and B2LA compounds. Five individual measurements were made to obtain the average and standard deviation (shown as error bars) of intensity values.

From the figure, it can be seen that B2LA and B7LA compounds showed comparatively significant SERS intensity compared to C3LA, C7LA and C9LA. It is postulated that the C-series compounds showed a low SERS signal due to the orientational changes occurred during chemisorption process that affect the proper adsorption on to the gold surface resulting in the lower SERS intensity.

Example 23

Physisorption and Chemisorption SERS Study of B2 and B2La after Peg Encapsulation: Time Course Study TM reporter molecule, B2, and its modified lipoic acid linker B2LA was chosen for comparative SERS study as they proved to be the best reporter in terms of SERS signal intensity. Thiolated PEG (PEG-SH) encapsulation of both compounds has been performed with the aforementioned procedure. As can be seen from FIG. 16(B), the time course study substantiates that the average SERS intensity value of B2 is higher than that of B2LA but exhibits poor stability. For instance, the relative standard deviation (RSD) of SERS signal measured from B2 was more than 25%. But, B2LA compound exhibits fairly consistent SERS signal up to 10 days with a low RSD of about 2 to 3%. From this comparative time course SERS study, we found that chemisorbed B2LA reporter was the most promising in terms of SERS intensity and stability.

Example 24

Comparative Time Course SERS Signal Stability of Chemisorbed Reporter Molecule B2LA and MGITC In addition, the SERS properties of B2LA compound were compared with current state of the art dye MGITC as a potential Raman reporter. These two dyes were adsorbed on to Au-colloid and followed by thiolated PEG encapsulation. The SERS spectra of these two dyes show similar spectral pattern due to their same triphenylmethine core skeleton. However, we noted minute difference in their spectra. Two non-overlapped peaks were found at 1590 $cm^{-1}$ in MGITC and at 1510 $cm^{-1}$ in B2LA containing nanotag (see FIGS. 10 (A) and (B)).

Figure 17:
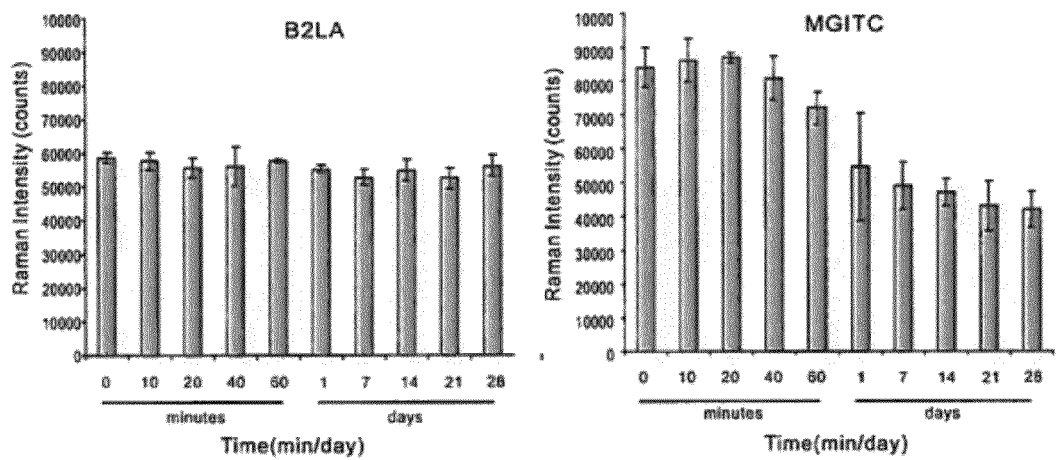
FIG. 17 are graphs showing time course study of SERS signal intensity of PEG encapsulated nanotags for (A) B2LA and (B) MGITC.

Time course SERS study was conducted to grade the stability of SERS signal intensity from B2LA and MGITC. FIG. 17 are graphs showing time course study of SERS signal intensity of PEG encapsulated nanotags for (A) B2LA and (B) MGITC.

From the figure, it can be seen that initially MGITC have shown higher SERS intensity than B2LA, but over longer time duration its intensity decreased gradually, whereas intensity from B2LA remained stable over a period of one month. It was found that the SERS signal intensity from MGITC was reduced by at least 30% over first 4 to 6 days. On the other hand, B2LA showed stable SERS signal over this time period. This may be due to the 1,2-bis thiol functionality of lipoic acid in B2LA. It is expected to exhibit a stronger bond formation occurred between Au and two S atoms, whereas in the case of MGITC chemically weak Au-SCN interaction is the main binding force. When the binding force is weak, more fluctuations can arise and this explains the unsteady SERS signals observed for MGITC compared to B2LA. Also, the orientational difference of the molecule on the surface plays a major role in SERS intensity. The orientation effect of MGITC, which is not always stable on Au surface, may cause the detachment of molecule from Au surface and resulted in its inconsistent SERS signals over time. The observed better signal stability of B2LA reporter will be a critical parameter especially when developing a SERS nanotag for in vivo applications.

Example 25

Recognition of EGFR and HER2 Cancer Proteins by Antibody Conjugated Nanotag—In Vitro Assay Next, spectroscopic detection by SERS measurement and fluorescent imaging of cancer cells with our nanotag conjugated with specific antibodies was carried out. Mouse monoclonal antibodies against epidermal growth factor receptors such as EGFR (Erb-B1) and HER2/neu (Erb-B2) were used. EGFR is over-expressed in diverse cancers and HER2 is a well-known breast cancer marker, as exemplified for example in Zhang et al. (Zhang et al., 2007, J. Clin. Invest. 117, 2051-2058). They belong to a family of membrane receptor tyrosine kinase that regulates cell cycle and therefore, their abnormal expression promotes cancer progression.

Those antibodies used to recognize the external epitope on respective antigens and are labeled with FITC. In this process, nanotag with B2LA reporter has been encapsulated with thiol-PEG (SH-PEG) and a heterofunctional PEG (SH-PEC-COOH) which imparts stability of the nanotag as well as antibody conjugation with terminal COOH group of heterofunctional PEG. For antibody conjugation, this heterofunctional PEG was covalently conjugated with the free amine functionality of antibody (Graham et al. (Graham et al., 2008, Nat. Nanotechnol. 3, 548-551); Lee et al. (Lee et al., 2009a., Mol. BioSyst. 5, 411-421 and Lee et al., 2009b, Biosens. Bioelectron, 24, 2260-2263); Yang et al., (Yang et al, 2009, Small, 5, 235-243)) which was confirmed by the observation of protein absorption peak at 280 nm using a UV-vis spectrometer. The developed nanotag were characterized by SERS measurement, UV-vis absorption and TEM images (see FIGS. 12 to 15).

To substantiate the specificity of the functionalized nanotag, the differential attachment of anti-HER2 labeled nanotag on two different cell lines, SKBR-3 cells (HER2-positive cancer cells) and MDA-MB-231 cells (HER2 negative cancer cells) was examined. Previously, Park et al. (Park et al., 2009, Phys. Chem. Chem. Phys., 11, 7444-7449.), demonstrated the recognition of HER2-expression by secondary antibody conjugated gold nanorods (GNRs) in MCF7 cell surfaces.

Figure 18:
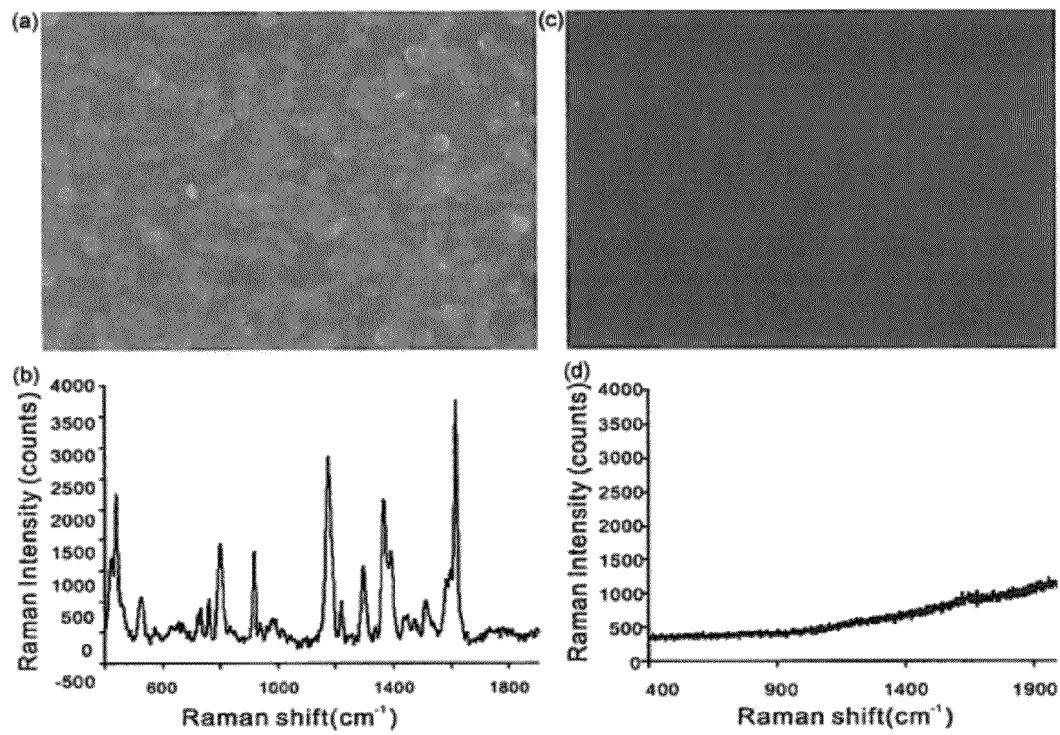
FIG. 18 (A) is a fluorescence image demonstrating recognition of HER2 (FITC labeled p185 (HER2) antibody attached Au-B2LA nanotag) over-expressed on the SKBR-3 cell surface; (B) is a SERS spectrum obtained from HER2 positive cancer cells (SKBR-3) (C) is a fluorescence image which demonstrates that there is no recognition in MDA-MB- 231 cells (HER2 negative); and (D) is a SERS spectrum from HER2 negative cancer cells (MDA-MB-231). SERS spectra were taken in cell suspension with 633 nm laser excitation at 6.2 mW.

In our case, the recognition process has been simplified by using directly primary antibody tagged nanotag recognition on the cell surface receptors. We have used our antibody attached nanotag as a duel detection probe. First, fluorescence microscopic study was carried out with the functionalized FITC labeled antibody attached SERS nanotag. FIG. 18(A) is a fluorescence image demonstrating recognition of HER2 (FITC labeled p185 (HER2) antibody attached Au-B2LA nanotag) over-expressed on the SKBR-3 cell surface; (B) is a SERS spectrum obtained from HER2 positive cancer cells (SKBR-3) (C) is a fluorescence image which demonstrates that there is no recognition in MDA-MB-231 cells (HER2 negative); and (D) is a SERS spectrum from HER2 negative cancer cells (MDA-MB-231). SERS spectra were taken in cell suspension with 633 nm laser excitation at 6.2 mW.

Figure 19:
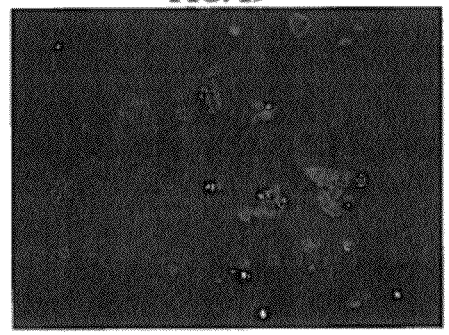
FIG. 19 (A) is a fluorescence image demonstrating recognition of EGFR (FITC labeled EGFR antibody attached Au-B2LA nanotag) overexpressed on the SCC-15 cell surface; (b) no recognition in MCF-7 cells (EGFR negative); (c) SERS spectrum obtained from EGFR-positive cancer cells (SCC-15) and (d) SERS spectrum from EGFR negative cancer cells (MCF-7). SERS spectra were taken in cell suspension with 633 nm laser excitation under confocal Raman microscope. Laser power used was 6.2 mW.
Figure 19:
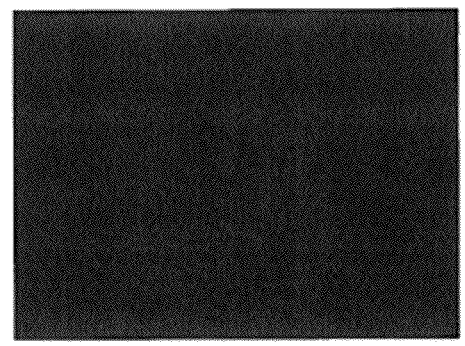
Figure 19:
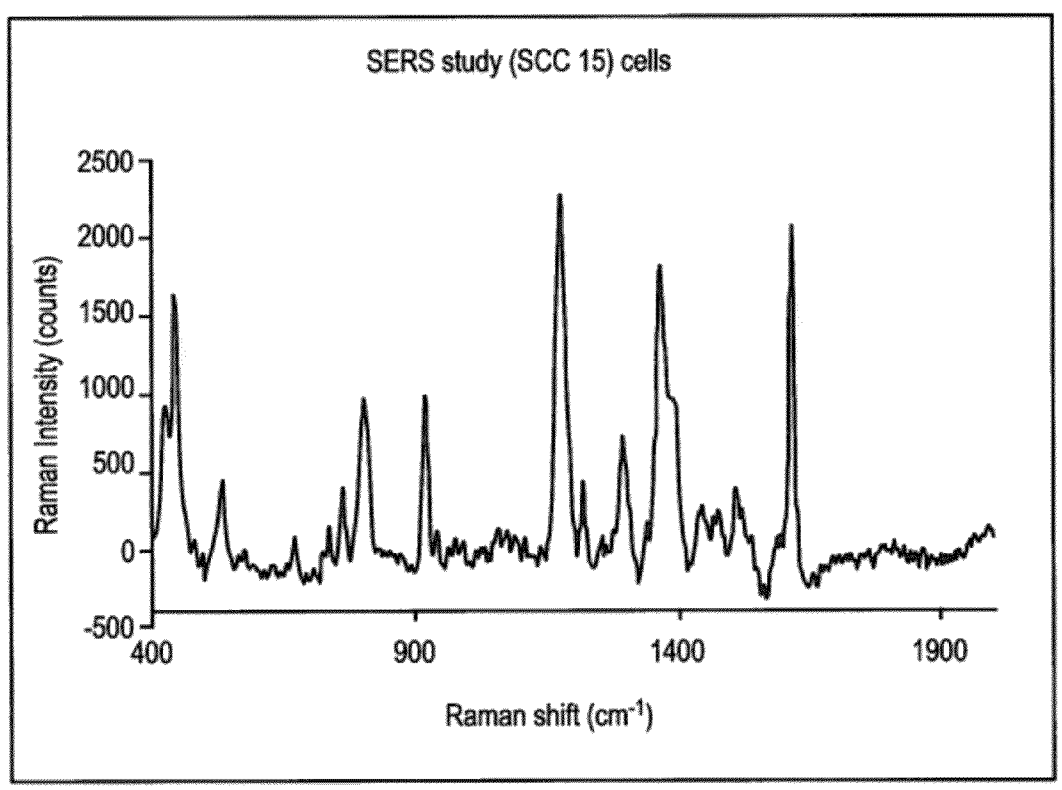
Figure 19:
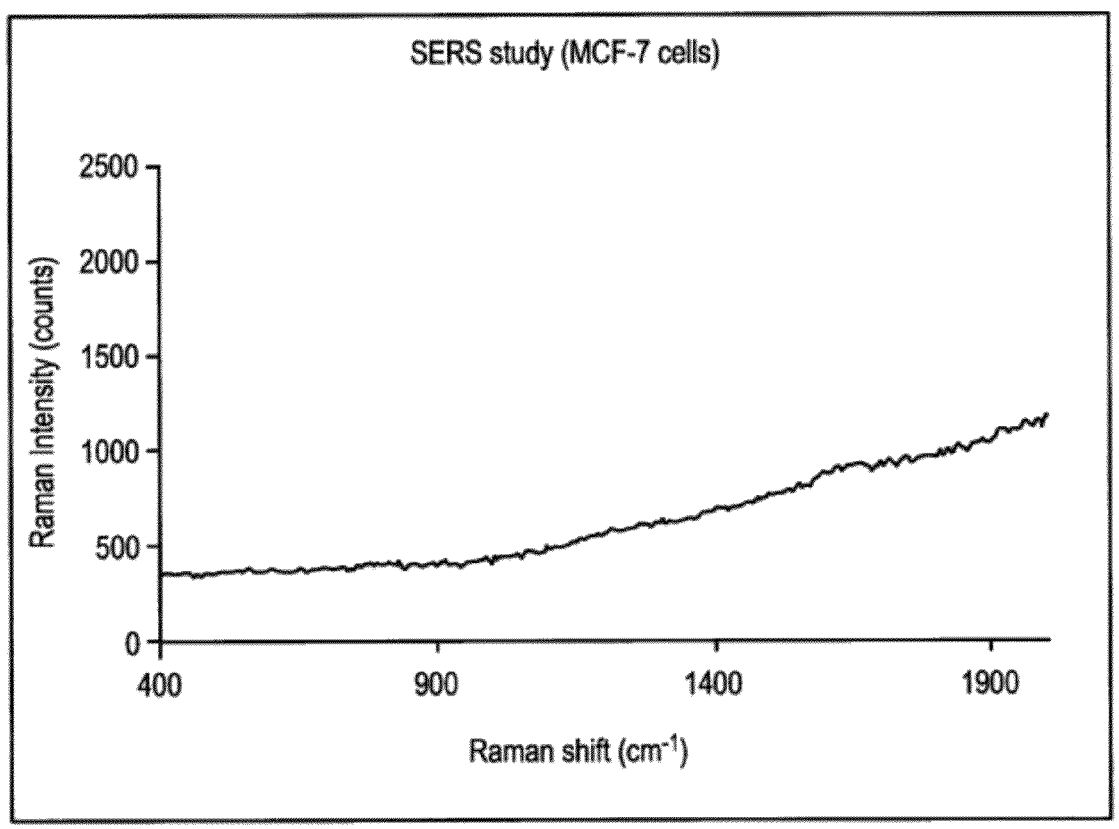

Fluorescence images (FIGS. 18(A) and (C)) clearly indicated the distinct green fluorescence from cell surface of SKBR-3 cells whereas almost no fluorescence signal was observed in MDA-MB-231 cells under same experimental condition. Further, SKBR-3 cells suspension contained antibody attached nanotag showed a strong SERS signal whereas no detectable signal was obtained from MDA-MB-231 cell suspension as shown in FIGS. 18(B) and (D). A portion of the cells were incubated with pegylated SERS nanoparticles as control experiment to confirm the signal is not from non-specific binding. A similar experiment was carried out with another cancer marker EGFR. FIG. 19(A) is a fluorescence image demonstrating recognition of EGFR (FITC labeled EGFR antibody attached Au-B2LA nanotag) overexpressed on the SCC-15 cell surface; (b) no recognition in MCF-7 cells (EGFR negative); (c) SERS spectrum obtained from EGFR-positive cancer cells (SCC-15) and (d) SERS spectrum from EGFR negative cancer cells (MCF-7). SERS spectra were taken in cell suspension with 633 nm laser excitation under confocal Raman microscope. Laser power used was 6.2 mW. As can be seen from the images, strong SERS signals and fluorescence signal was detected from SCC-15 cells, but MCF-7 cells showed no detectable signals. This result suggests that antibody conjugated nanotag selectively and efficiently binds to the cancerous cell lines with HER2 and EGFR expression on the cell surface.

Example 26

In Vivo SERS Measurement in Animal Model

Figure 20:
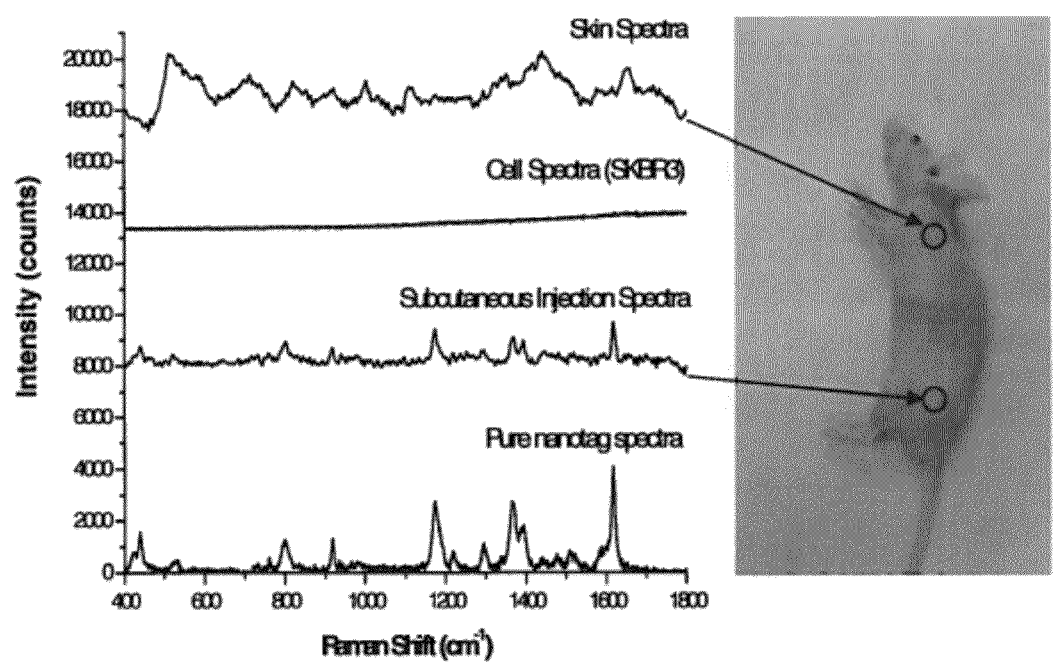
FIG. 20 is a spectral comparison of functionalized AuNP used in ex vivo and in vivo studies; pegylated gold nanotag with B2LA reporter molecule attached with HER2 antibody [sc-71667, Neu(0.N.221)]. Pure tag; SERS spectra obtained from antibody conjugated nanotag (black) in PBS suspension; subcutaneous injection of SKBR-3 cell suspension with recognized antibody attached nanotag; cell (SKBR-3) only; skin spectrum. SERS spectra were taken with 633 nm laser excitation at laser power of 6.2 mW.

Finally, the performance of the functionalized nanotag was evaluated in an in vivo SERS measurement. In this study, as a proof of concept, SERS measurement in a mouse was successfully carried out to detect the nanotag-anchored cancer cells that were subcutaneously injected to the animal. We chose SKBR-3 cell suspension with the antibody attached SERS nanotag and injected subcutaneously to an animal model. The SERS spectrum was measured through the skin which was shown in FIG. 20. FIG. 20 is a spectral comparison of functionalized AuNP used in ex vivo and in vivo studies; pegylated gold nanotag with B2LA reporter molecule attached with HER2 antibody [sc-71667, Neu(0.N.221)]. Pure tag; SERS spectra obtained from antibody conjugated nanotag (black) in PBS suspension; subcutaneous injection of SKBR-3 cell suspension with recognized antibody attached nanotag (red); cell (SKBR-3) only (green); skin spectrum (blue). 633 nm laser excitation at 6.2 mW.

The nanotag containing B2LA reporter showed spectral signatures at 1617, 1400, 1388, 1180, 910, 800, 730, and 445 cm$^{-1}$, which do not exist in the Raman signal of the animal skin. It was found that in vivo spectrum of cell suspension containing antibody conjugated SERS nanotag clearly matches with pure nanotag spectrum. This proves the high sensitivity of our SERS nanotag and its potential to use for future in vivo xenograft studies in an animal model.

In summary, a novel biocompatible SERS nanotag with enhanced stability by using the sensitive Raman reporters according to various aspects of the invention with lipoic acid linker for chemisorption treatment has been developed. Among the TM-linker dyes, B2LA compound exhibited strongest SERS signal with better signal stability compared to MGITC. The stabilized nanotags were functionalized to bind selectively to EGFR and HER2 over-expressing cancer cells, which were confirmed by SERS spectroscopic and cell-imaging studies. Lastly, the animal study substantiated that sensitivity and stability achieved from the synthesized nanotag was adequate for bioimaging and sensing experiments.

What is claimed is:
1. A compound having Formula I:

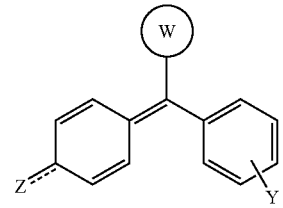

Formula I wherein
W is selected from the group consisting of

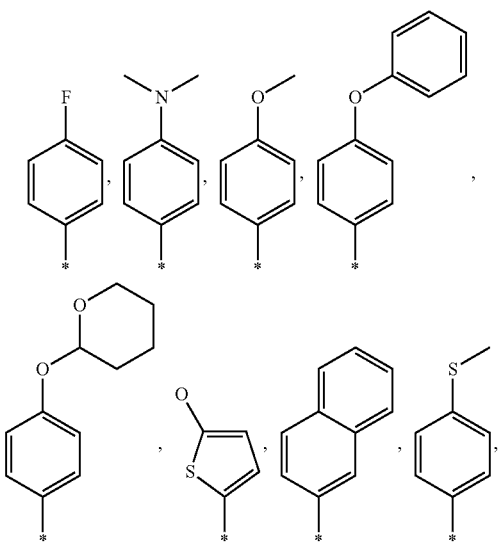

-continued

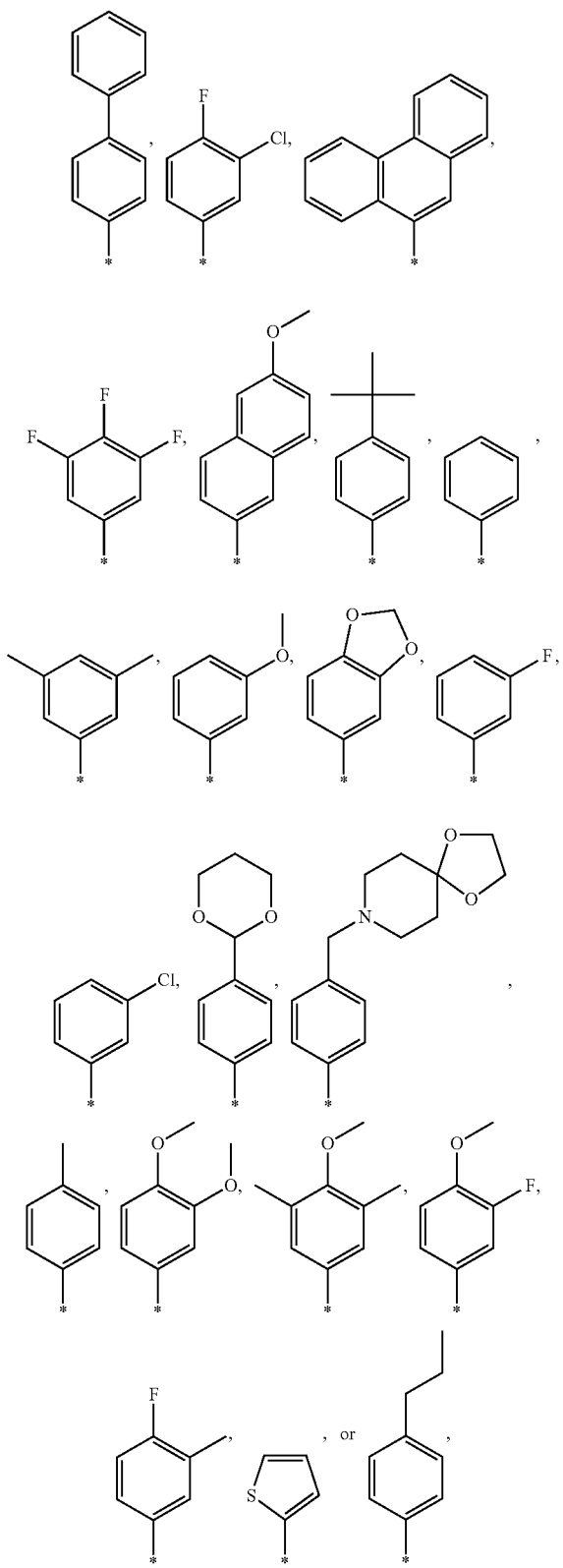

wherein the symbol "*" denotes the point at which W may be connected to the remainder of the compound of Formula I;

Y is selected from $NH_2$, $N(CH_3)_2$ or

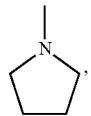

╌╌╌ is used to denote a single bond or a double bond, and Z is NH, $NH_2$, or

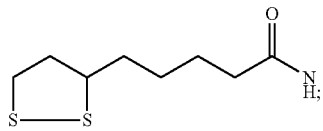

or a tautomer or stereoisomer thereof, or a salt thereof.

2. The compound according to claim 1, wherein W is selected from the group consisting of

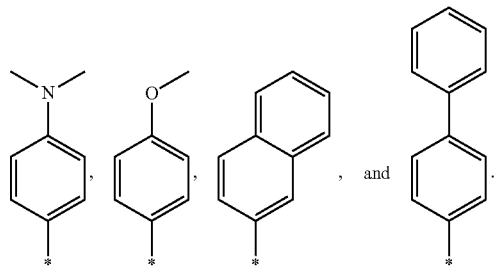

3. The compound according to claim 1, wherein Y is $N(CH_3)_2$ and W is selected from the group consisting of

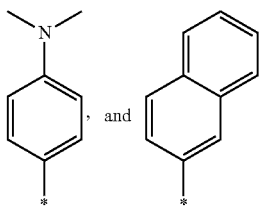

4. The compound according to claim 1, wherein Y is

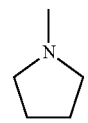

and W is selected from the group consisting of

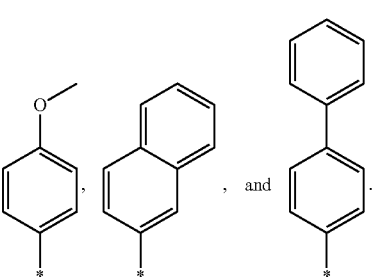

5. The compound according to claim 1, wherein the compound is selected from the group consisting of
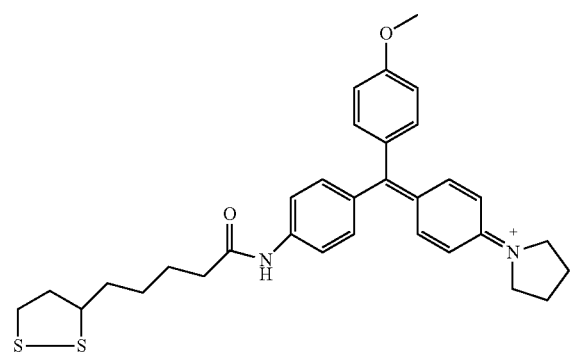
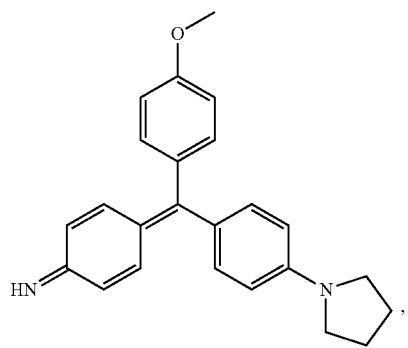
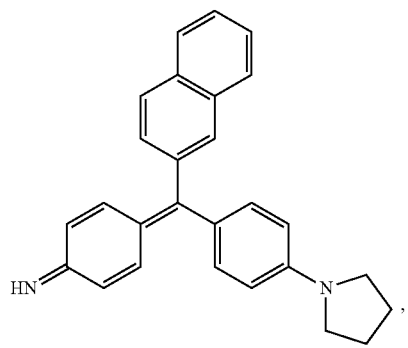
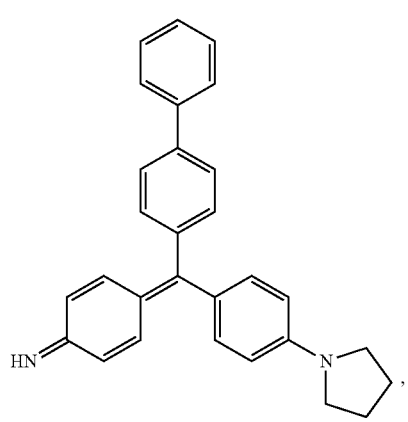
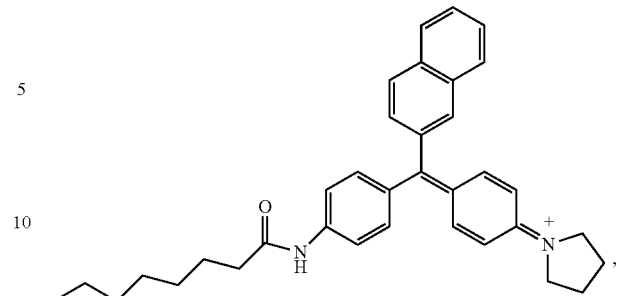
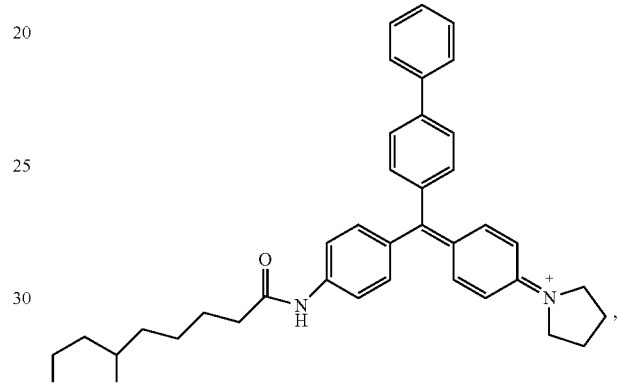
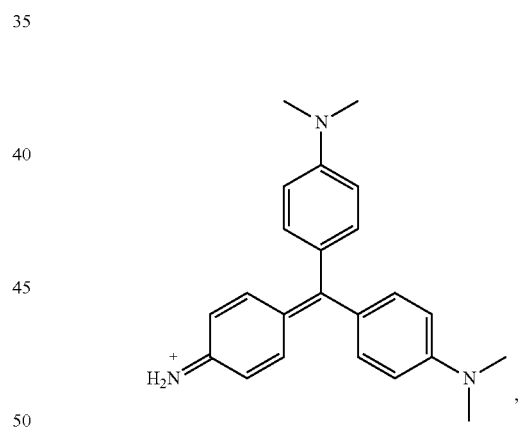
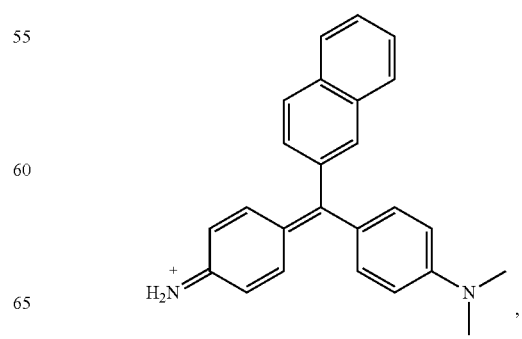

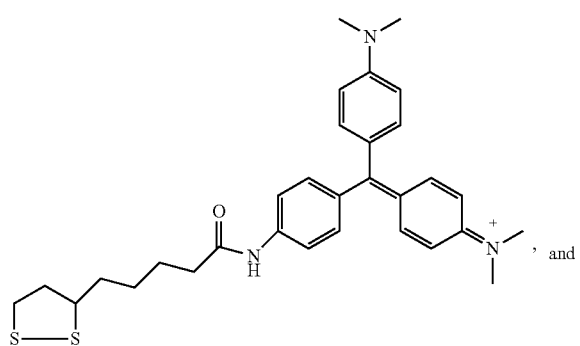
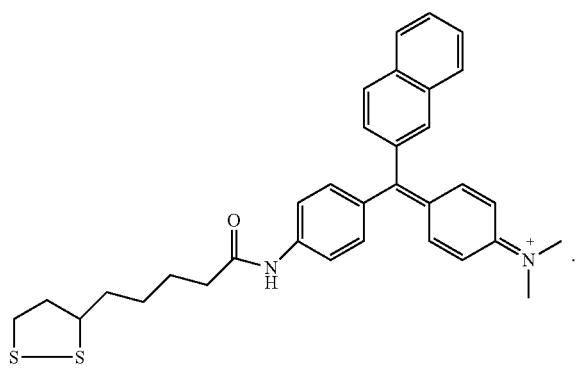
6. The compound according to claim 1, wherein the compound is selected from the group consisting of
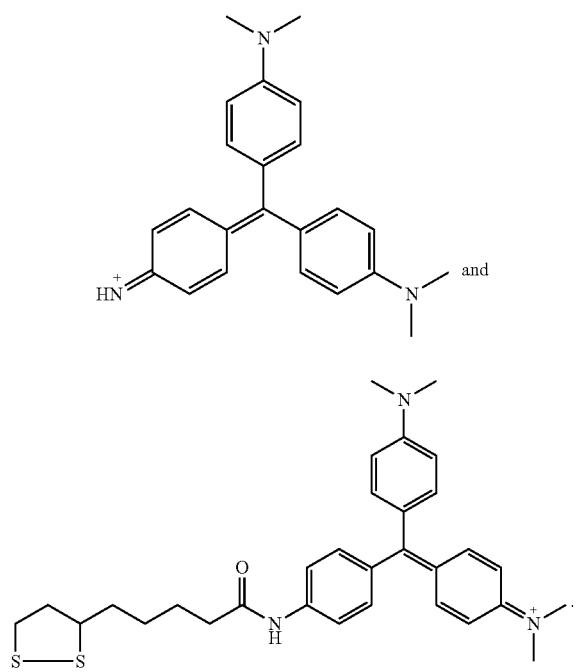
7. A SERS marker conjugate comprising a nanoparticle and a Raman-active marker compound attached to the nanoparticle surface, wherein the compound has Formula I:
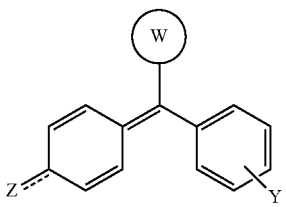
wherein
W is selected from the group consisting of
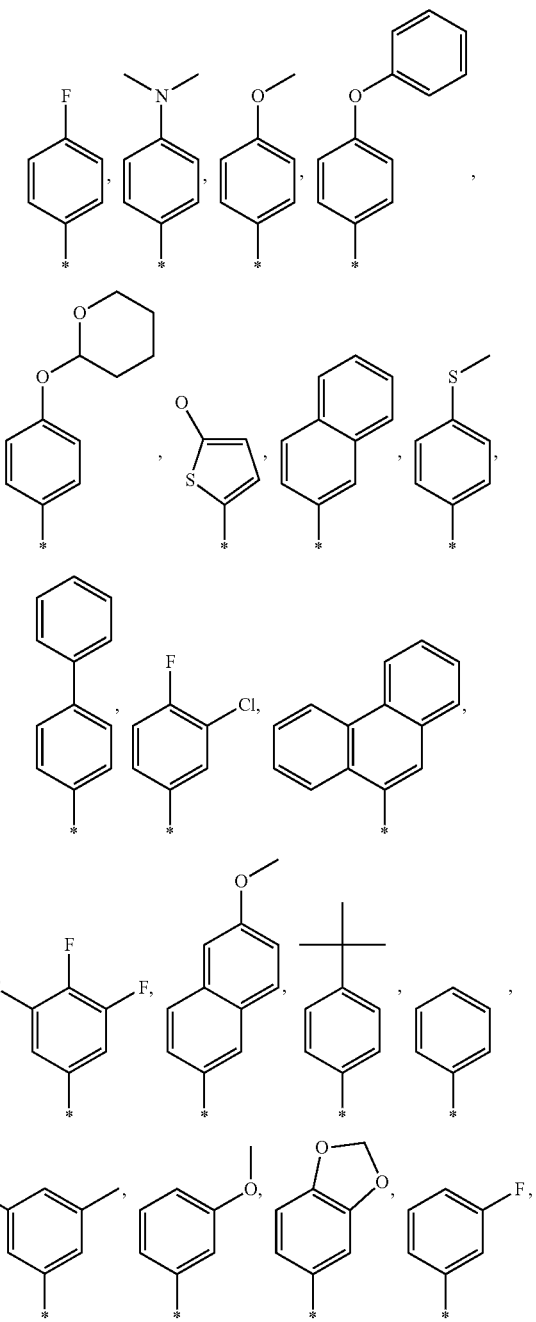

-continued

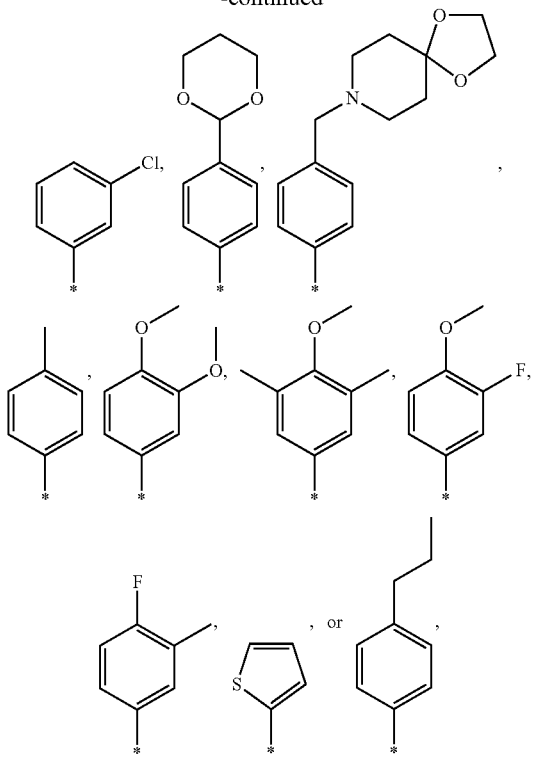

wherein the symbol "*" denotes the point at which W may be connected to the remainder of the compound of Formula I;
selected from NH₂, N(CH₃)₂ or

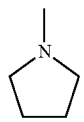

------ is used to denote a single bond or a double bond, and Z is NH, NH₂, or

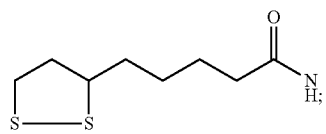

or a tautomer or stereoisomer thereof, or a salt thereof.

8. The SERS marker conjugate according to claim 7, further comprising an analyte-binding molecule coupled to the Raman-active marker compound, wherein the analyte binding molecule is an antibody.

9. The SERS marker conjugate according to claim 7, wherein the nanoparticle is coated with or consisting of a noble metal.

10. The SERS marker conjugate according to claim 9, wherein the noble metal is gold.

11. The SERS marker conjugate according to claim 7, wherein the nanoparticle is a citrate-stabilized gold nanoparticle.

12. The SERS marker conjugate according to claim 7, further comprising thiolated polyethylene glycol (PEG), wherein thiolated polyethylene glycol (PEG) forms a layer around the SERS marker conjugate.

13. A biosensor comprising a plurality of SERS marker conjugates, wherein a SERS marker conjugate comprises a nanoparticle and a Raman-active marker compound attached to the nanoparticle surface, wherein the compound has Formula I:

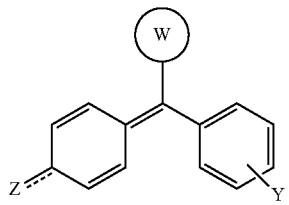

Formula I wherein
W is selected from the group consisting of

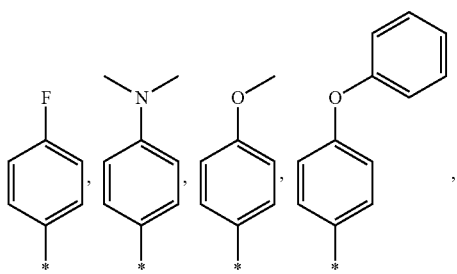

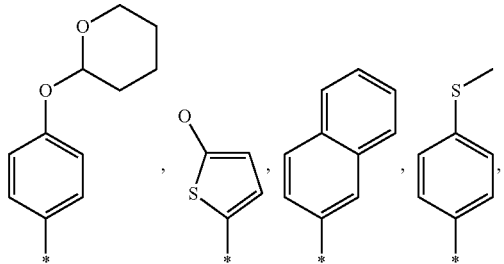

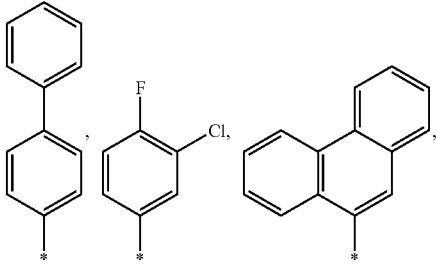

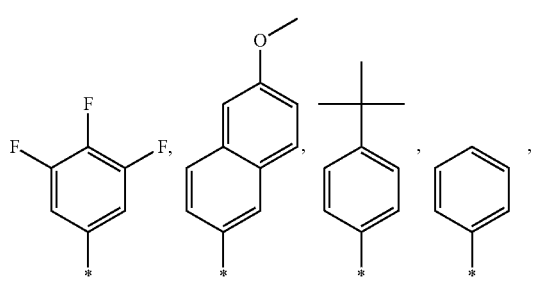

-continued

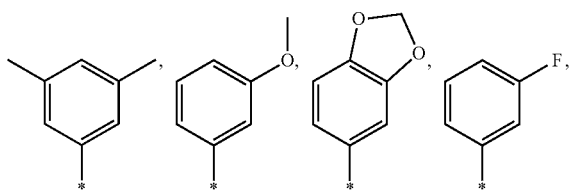

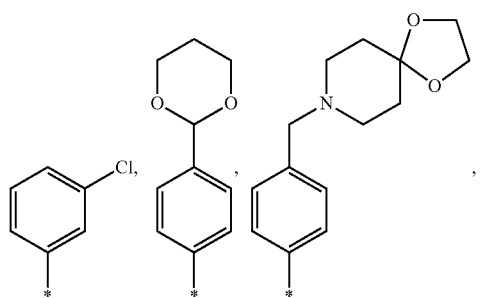

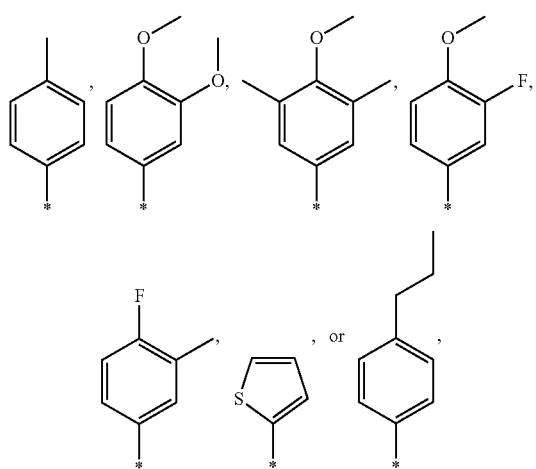

wherein the symbol "*" denotes the point at which W may be connected to the remainder of the compound of Formula I;

Y is selected from $NH_2$, $N(CH_3)_2$ or

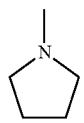

═ is used to denote a single bond or a double bond, and
Z is NH, $NH_2$, or

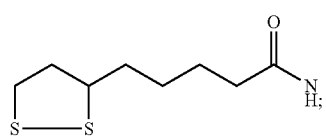

or a tautomer or stereoisomer thereof, or a salt thereof.

14. The biosensor according to claim 13, further comprising a substrate, wherein the nanoparticles are adherent to the substrate.

15. Method for the detection of any analyte using a SERS marker conjugate, wherein a SERS marker conjugate comprises a nanoparticle and a Raman-active marker compound attached to the nanoparticle surface, wherein the compound having Formula I:

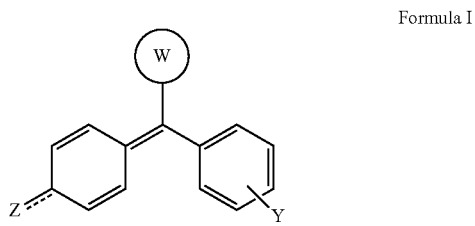

Formula I wherein
W is selected from the group consisting of

-continued

[structures]

wherein the symbol "*" denotes the point at which W may be connected to the remainder of the compound of Formula I;

Y is selected from NH₂, N(CH₃)₂ or

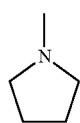

┄┄┄ is used to denote a single bond or a double bond, and Z is NH, or

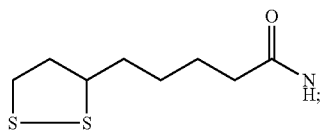

or a tautomer or stereoisomer thereof, or a salt thereof.

16. The method according to claim 15, wherein the analyte is detected in a bodily fluid comprising the analyte.

17. The method according to claim 16, wherein the bodily fluid is selected from the group consisting of plasma, serum, blood, lymph, liquor and urine.

18. The method according to claim 15, wherein the analyte is one selected from the group consisting of proteins, peptides, nucleic acids, carbohydrates, lipids, cells, viruses, small molecules, or haptens.

19. Method for the detection of any analyte using a biosensor comprising a plurality of SERS marker conjugates, wherein the SERS marker conjugate comprises a nanoparticle and a Raman-active marker compound attached to the nanoparticle surface, wherein the compound has Formula I:

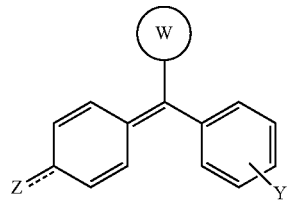

Formula I wherein
W is selected from the group consisting of

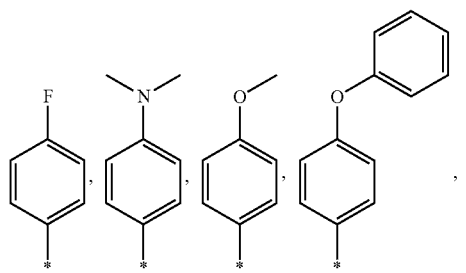

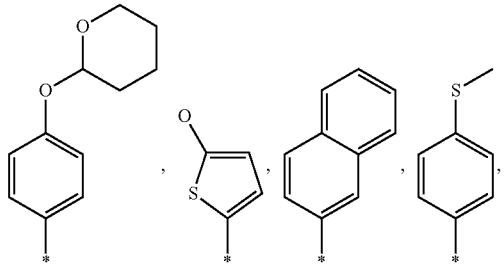

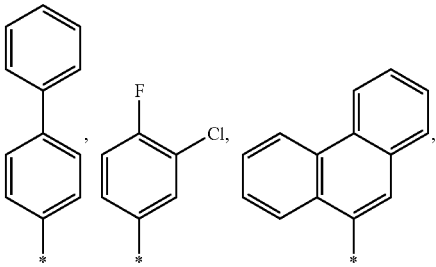

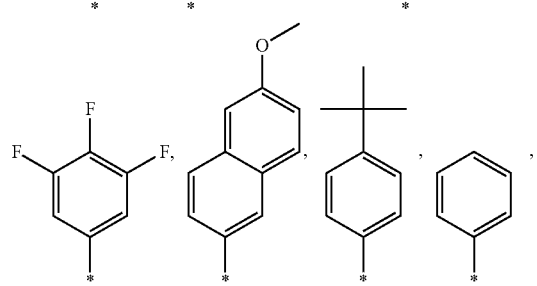

-continued

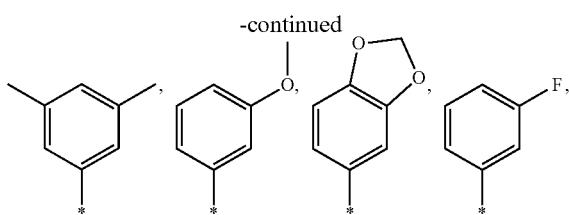

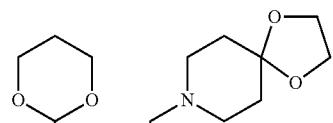

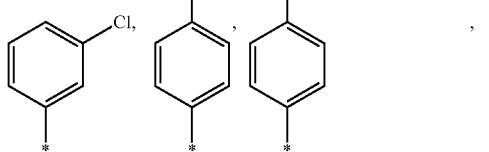

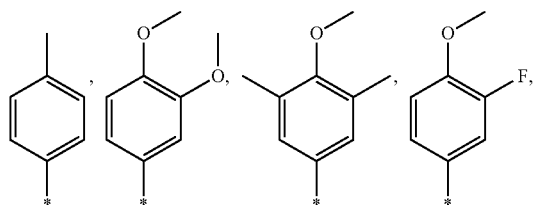

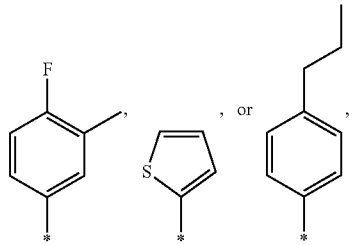

wherein the symbol "*" denotes the point at which W may be connected to the remainder of the compound of Formula I;

Y is selected from $NH_2$, $N(CH_3)_2$ or

----- is used to denote a single bond or a double bond, and

Z is NH, $NH_2$, or or a tautomer or stereoisomer thereof, or a salt thereof.

20. The method according to claim 19, wherein the analyte is detected in a bodily fluid comprising the analyte.

21. The method according to claim 20, wherein the bodily fluid is selected from the group consisting of plasma, serum, blood, lymph, liquor and urine.

22. The method according to claim 19, wherein the analyte is one selected from the group consisting of proteins, peptides, nucleic acids, carbohydrates, lipids, cells, viruses, small molecules, or haptens.

* * * * *